US010174110B2

(12) United States Patent
Meade et al.

(10) Patent No.: US 10,174,110 B2
(45) Date of Patent: Jan. 8, 2019

(54) HIGHLY GALACTOSYLATED ANTI-TNF-α ANTIBODIES AND USES THEREOF

(71) Applicant: Laboratoire Français du Fractionnement et des Biotechnologies, Les Ulis (FR)

(72) Inventors: Harry M. Meade, Newton, MA (US); Li-How Chen, Acton, MA (US)

(73) Assignee: Laboratoire Français du Fractionnement et des Biotechnologies, Les Ulis (FR)

( * ) Notice: Subject to any disclaimer, the term of this patent is extended or adjusted under 35 U.S.C. 154(b) by 77 days.

(21) Appl. No.: 14/767,117

(22) PCT Filed: Feb. 13, 2014

(86) PCT No.: PCT/IB2014/000692
§ 371 (c)(1),
(2) Date: Aug. 11, 2015

(87) PCT Pub. No.: WO2014/125374
PCT Pub. Date: Aug. 21, 2014

(65) Prior Publication Data
US 2015/0368334 A1 Dec. 24, 2015

Related U.S. Application Data

(60) Provisional application No. 61/764,475, filed on Feb. 13, 2013.

(51) Int. Cl.
*C07K 16/24* (2006.01)
*C07K 16/04* (2006.01)
*A61K 39/395* (2006.01)
*C07K 16/28* (2006.01)

(52) U.S. Cl.
CPC ........ *C07K 16/241* (2013.01); *A61K 39/3955* (2013.01); *A61K 39/39508* (2013.01); *C07K 16/04* (2013.01); *C07K 16/283* (2013.01); *C07K 2317/12* (2013.01); *C07K 2317/41* (2013.01); *C07K 2317/732* (2013.01); *C07K 2317/734* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,399,216 A | 8/1983 | Axel et al. |
| 4,816,397 A | 3/1989 | Boss et al. |
| 4,816,567 A | 3/1989 | Cabilly et al. |
| 4,873,316 A | 10/1989 | Meade et al. |
| 4,946,778 A | 8/1990 | Ladner et al. |
| 5,202,238 A | 4/1993 | Fell et al. |
| 5,304,489 A | 4/1994 | Rosen |
| 5,322,775 A | 6/1994 | Clark et al. |
| 5,545,806 A | 8/1996 | Lonberg et al. |
| 5,545,807 A | 8/1996 | Surani et al. |
| 5,576,040 A | 11/1996 | Moller et al. |
| 5,589,604 A | 12/1996 | Drohan et al. |
| 5,591,669 A | 1/1997 | Krimpenfort et al. |
| 5,633,076 A | 5/1997 | DeBoer et al. |
| 5,639,940 A | 6/1997 | Garner et al. |
| 5,648,243 A | 7/1997 | Hurwitz et al. |
| 5,648,253 A | 7/1997 | Wei |
| 5,741,957 A | 4/1998 | Deboer et al. |
| 5,750,172 A | 5/1998 | Meade et al. |
| 5,756,687 A | 5/1998 | Denman et al. |
| 5,780,009 A | 7/1998 | Karatzas et al. |
| 5,827,690 A | 10/1998 | Meade et al. |
| 5,831,141 A | 11/1998 | Lubon et al. |
| 5,843,705 A | 12/1998 | DiTullio et al. |
| 5,849,992 A | 12/1998 | Meade et al. |
| 5,892,070 A | 4/1999 | Prieto et al. |
| 5,945,577 A | 8/1999 | Stice et al. |
| 5,965,789 A | 10/1999 | Lubon et al. |
| 6,013,857 A | 1/2000 | Deboer et al. |
| 6,063,905 A | 5/2000 | Capra et al. |

(Continued)

FOREIGN PATENT DOCUMENTS

| | | |
|---|---|---|
| CA | 2 243 459 C | 9/2002 |
| CN | 1273602 A | 11/2000 |

(Continued)

OTHER PUBLICATIONS

[No Author Listed] GTC Provides Update on TG20 Monoclonal Antibody Targeting CD20. Press Release. Mar. 1, 2010. Accessed at http://www.businesswire.com/news/home/20100301006006/en/GTC-Update-TG20-Monoclonal-Antibody-Targeting-CD20.

[No Author Listed] Humira® (adalimumab) U.S. Package Insert. Jul. 30, 2004. 24 pages.

Abreu et al., Listeria infection in patients on anti-TNF treatment: report of two cases and review of the literature. J Crohns Colitis. Mar. 2013;7(2):175-82. doi: 10.1016/j.crohns.2012.04.018. Epub May 22, 2012.

Anolik et al., The relationship of FcgammaRIIIa genotype to degree of B cell depletion by rituximab in the treatment of systemic lupus erythematosus. Arthritis Rheum. Feb. 2003;48(2):455-9.

Anthony et al., Identification of a receptor required for the anti-inflammatory activity of IVIG. Proc Natl Acad Sci U S A. Dec. 16, 2008;105(50):19571-8.

(Continued)

*Primary Examiner* — Xiaozhen Xie
(74) *Attorney, Agent, or Firm* — Wolf, Greenfield & Sacks, P.C.

(57) ABSTRACT

In one aspect, the disclosure relates to highly galactosylated anti-TNF-alpha antibodies and compositions thereof. In one aspect, the disclosure relates to populations of anti-TNF-alpha antibodies with a high level of galactosylation, and compositions thereof. In one aspect, the disclosure relates to methods of production and use of highly galactosylated anti-TNF-alpha antibodies and populations of anti-TNF-alpha antibodies with a high level of galactosylation. In some embodiments, the anti-TNF-alpha antibody is adalimumab.

20 Claims, 29 Drawing Sheets
Specification includes a Sequence Listing.

(56) References Cited

U.S. PATENT DOCUMENTS

| | | | |
|---|---|---|---|
| 6,090,382 A * | 7/2000 | Salfeld | C07K 16/241 424/133.1 |
| 6,140,552 A | 10/2000 | Deboer et al. | |
| 6,150,584 A | 11/2000 | Kucherlapati et al. | |
| 6,201,167 B1 | 3/2001 | Pothier | |
| 6,204,431 B1 | 3/2001 | Prieto et al. | |
| 6,210,736 B1 | 4/2001 | Echelard et al. | |
| 6,217,866 B1 | 4/2001 | Schlessinger et al. | |
| 6,268,487 B1 | 7/2001 | Kutzko et al. | |
| 6,271,436 B1 | 8/2001 | Piedrahita et al. | |
| 6,441,145 B1 | 8/2002 | DiTullio et al. | |
| 6,448,469 B1 | 9/2002 | Smith | |
| 6,472,584 B1 | 10/2002 | Smith | |
| 6,528,699 B1 | 3/2003 | Meade et al. | |
| 6,545,198 B1 | 4/2003 | Echelard et al. | |
| 6,548,653 B1 | 4/2003 | Young et al. | |
| 6,580,017 B1 | 6/2003 | Echelard et al. | |
| 6,593,463 B1 | 7/2003 | Chen et al. | |
| 6,727,405 B1 | 4/2004 | Gordon et al. | |
| 6,743,966 B2 | 6/2004 | Smith | |
| 6,924,412 B1 | 8/2005 | de Groot et al. | |
| 6,933,368 B2 | 8/2005 | Co et al. | |
| 7,019,193 B2 | 3/2006 | Ditullio et al. | |
| 7,029,872 B2 | 4/2006 | Gerngross | |
| 7,045,676 B1 | 5/2006 | Gordon et al. | |
| 7,053,202 B2 | 5/2006 | O'Keefe et al. | |
| 7,087,719 B2 | 8/2006 | Visuri et al. | |
| 7,101,971 B2 | 9/2006 | Meade et al. | |
| 7,354,594 B2 | 4/2008 | Chen et al. | |
| 7,501,553 B2 | 3/2009 | Chen et al. | |
| 7,531,632 B2 | 5/2009 | Perreault | |
| 7,550,263 B2 | 6/2009 | Meade et al. | |
| 7,632,980 B1 | 12/2009 | Chen et al. | |
| 7,651,686 B2 | 1/2010 | Chen et al. | |
| 7,700,321 B2 | 4/2010 | McPherson et al. | |
| 7,867,491 B2 | 1/2011 | Yang et al. | |
| 7,928,064 B2 | 4/2011 | DiTullio et al. | |
| 7,931,895 B2 | 4/2011 | Beliard et al. | |
| 7,939,317 B1 | 5/2011 | Gordon et al. | |
| 8,173,860 B2 | 5/2012 | Meade et al. | |
| 9,511,087 B2 | 12/2016 | Frieling et al. | |
| 2002/0131957 A1 | 9/2002 | Gavin et al. | |
| 2002/0144299 A1 | 10/2002 | Chen et al. | |
| 2002/0155998 A1 | 10/2002 | Young et al. | |
| 2003/0005468 A1 | 1/2003 | Meade et al. | |
| 2003/0033618 A1 | 2/2003 | Smith | |
| 2003/0036637 A1 | 2/2003 | Fulton | |
| 2003/0046716 A1 | 3/2003 | Echelard et al. | |
| 2003/0096974 A1 | 5/2003 | Ditullio et al. | |
| 2003/0140358 A1 | 7/2003 | Nuijens et al. | |
| 2003/0175884 A1 | 9/2003 | Umana et al. | |
| 2003/0177513 A1 | 9/2003 | Echelard et al. | |
| 2003/0204860 A1 | 10/2003 | Melican et al. | |
| 2003/0213003 A1 | 11/2003 | Meade et al. | |
| 2004/0006776 A1 | 1/2004 | Meade et al. | |
| 2004/0025193 A1 | 2/2004 | Echelard et al. | |
| 2004/0033561 A1 | 2/2004 | O'Keefe et al. | |
| 2004/0068760 A1 | 4/2004 | Robl et al. | |
| 2004/0092719 A1 | 5/2004 | Birck-Wilson et al. | |
| 2004/0097710 A1 | 5/2004 | Visuri et al. | |
| 2004/0098755 A1 | 5/2004 | Mulroy et al. | |
| 2004/0102380 A1 | 5/2004 | Fulton et al. | |
| 2004/0109847 A1 | 6/2004 | Chen et al. | |
| 2004/0117863 A1 | 6/2004 | Edge et al. | |
| 2004/0121303 A1 | 6/2004 | Gavin et al. | |
| 2004/0132101 A1 | 7/2004 | Lazar et al. | |
| 2004/0133931 A1 | 7/2004 | Gavin et al. | |
| 2004/0143857 A1 | 7/2004 | Young et al. | |
| 2004/0148648 A1 | 7/2004 | Behboodi et al. | |
| 2004/0167320 A1 | 8/2004 | Couto et al. | |
| 2004/0192595 A1 | 9/2004 | Murakami et al. | |
| 2004/0205832 A1 | 10/2004 | Meade et al. | |
| 2004/0226052 A1 | 11/2004 | Meade et al. | |
| 2004/0226053 A1 | 11/2004 | Meade et al. | |
| 2005/0013811 A1 | 1/2005 | Chen et al. | |
| 2005/0037000 A1 | 2/2005 | Stavenhagen et al. | |
| 2005/0060766 A1 | 3/2005 | Chen | |
| 2005/0071890 A1 | 3/2005 | Chen et al. | |
| 2005/0097625 A1 | 5/2005 | Meade et al. | |
| 2005/0123546 A1 | 6/2005 | Umana et al. | |
| 2005/0158832 A1 | 7/2005 | Young et al. | |
| 2005/0160483 A1 | 7/2005 | Meade et al. | |
| 2005/0169908 A1 | 8/2005 | Murakami et al. | |
| 2005/0177882 A1 | 8/2005 | Gavin et al. | |
| 2005/0181482 A1 | 8/2005 | Meade et al. | |
| 2005/0186608 A1 | 8/2005 | Olsen | |
| 2005/0192226 A1 | 9/2005 | Enkhbaatar et al. | |
| 2005/0193431 A1 | 9/2005 | Echelard et al. | |
| 2005/0197496 A1 | 9/2005 | Perreault | |
| 2005/0208000 A1 | 9/2005 | Bernstein et al. | |
| 2005/0229261 A1 | 10/2005 | Cheng et al. | |
| 2005/0235371 A1 | 10/2005 | Chen et al. | |
| 2005/0245444 A1 | 11/2005 | Echelard et al. | |
| 2005/0260672 A1 | 11/2005 | Couto et al. | |
| 2006/0026695 A1 | 2/2006 | Edge et al. | |
| 2006/0057638 A1 | 3/2006 | Bosques et al. | |
| 2006/0105347 A1 | 5/2006 | Meade et al. | |
| 2006/0121004 A1 | 6/2006 | Echelard et al. | |
| 2006/0123500 A1 | 6/2006 | Echelard et al. | |
| 2006/0127950 A1 | 6/2006 | Bosques et al. | |
| 2006/0130159 A1 | 6/2006 | Masiello et al. | |
| 2006/0168671 A1 | 7/2006 | Gavin et al. | |
| 2006/0174359 A1 | 8/2006 | Melican et al. | |
| 2006/0178309 A1 | 8/2006 | Visuri et al. | |
| 2006/0179493 A1 | 8/2006 | Meade et al. | |
| 2006/0179500 A1 | 8/2006 | Meade et al. | |
| 2006/0182744 A1 | 8/2006 | Strome et al. | |
| 2006/0188439 A1 | 8/2006 | Strome et al. | |
| 2006/0191025 A1 | 8/2006 | Echelard et al. | |
| 2006/0191029 A1 | 8/2006 | Gavin et al. | |
| 2006/0253913 A1 | 11/2006 | Huang et al. | |
| 2006/0272036 A1 | 11/2006 | Hammarstrom et al. | |
| 2006/0286548 A1 | 12/2006 | Liposky et al. | |
| 2007/0015239 A1 | 1/2007 | Bihoreau et al. | |
| 2007/0037192 A1 | 2/2007 | Ziomek et al. | |
| 2007/0048300 A1 | 3/2007 | Taylor et al. | |
| 2007/0092521 A1 | 4/2007 | McPherson et al. | |
| 2007/0192878 A1 | 8/2007 | Perreault | |
| 2008/0004212 A1 | 1/2008 | Echelard et al. | |
| 2008/0019905 A9 | 1/2008 | Strome et al. | |
| 2008/0063780 A1 | 3/2008 | Meade et al. | |
| 2008/0118501 A1 | 5/2008 | Schindler et al. | |
| 2008/0176786 A1 | 7/2008 | Ditullio et al. | |
| 2008/0269123 A1 | 10/2008 | Li et al. | |
| 2009/0068193 A1 | 3/2009 | Chen et al. | |
| 2009/0178147 A1 | 7/2009 | Harvey | |
| 2009/0239788 A1 | 9/2009 | Chtourou et al. | |
| 2009/0246194 A1 | 10/2009 | Meade et al. | |
| 2009/0252724 A1 | 10/2009 | Loetscher et al. | |
| 2010/0021612 A1 | 1/2010 | Meade et al. | |
| 2010/0056757 A1 | 3/2010 | Perreault | |
| 2010/0081794 A1 | 4/2010 | Liu et al. | |
| 2010/0173323 A1 | 7/2010 | Strome et al. | |
| 2010/0178292 A1 | 7/2010 | Wang et al. | |
| 2010/0266611 A1 | 10/2010 | Chen et al. | |
| 2011/0070167 A1 | 3/2011 | Enkhbaatar et al. | |
| 2011/0082083 A1 | 4/2011 | Magneson et al. | |
| 2011/0104049 A1 | 5/2011 | Strome et al. | |
| 2011/0229460 A1 | 9/2011 | Meade et al. | |
| 2012/0058047 A9 | 5/2012 | Strome et al. | |
| 2013/0149301 A1 | 6/2013 | Meade | |
| 2013/0302274 A1 | 11/2013 | Klein et al. | |
| 2013/0324619 A1 | 12/2013 | Chtourou | |
| 2014/0046033 A1 | 2/2014 | Schindler et al. | |
| 2014/0194360 A1 | 7/2014 | Frieling et al. | |
| 2014/0206617 A1 | 7/2014 | Frieling et al. | |
| 2014/0228301 A1 | 8/2014 | Meade et al. | |
| 2014/0242182 A1 | 8/2014 | Evans et al. | |
| 2014/0296490 A1 | 10/2014 | Faid et al. | |
| 2015/0175678 A1 | 6/2015 | Cavacini et al. | |
| 2015/0368334 A1 | 12/2015 | Meade et al. | |
| 2015/0368357 A1 | 12/2015 | Meade et al. | |
| 2015/0374801 A1 | 12/2015 | Chen et al. | |
| 2016/0002330 A1 | 1/2016 | Meade | |

(56) References Cited

U.S. PATENT DOCUMENTS

| | | |
|---|---|---|
| 2016/0039913 A1 | 2/2016 | Meade et al. |
| 2016/0089422 A1 | 3/2016 | Chtourou et al. |
| 2016/0129115 A1 | 5/2016 | Magneson et al. |
| 2016/0158676 A1 | 6/2016 | Hawkins et al. |
| 2016/0168229 A1 | 6/2016 | Paolantonacci et al. |
| 2016/0326547 A1 | 11/2016 | Meade et al. |
| 2017/0121402 A1 | 5/2017 | Chtourou |
| 2017/0129966 A1 | 5/2017 | Masiello |
| 2017/0190753 A1 | 7/2017 | Abache |

FOREIGN PATENT DOCUMENTS

| | | | |
|---|---|---|---|
| CN | 1387399 A | 12/2002 | |
| CN | 1607960 A | 4/2005 | |
| CN | 101460522 A | 6/2009 | |
| CN | 101588817 A | 11/2009 | |
| CN | 101802210 A | 8/2010 | |
| DE | 4000939 A1 | 7/1991 | |
| EP | 0 264 166 A1 | 4/1988 | |
| EP | 0 279 582 A2 | 8/1988 | |
| EP | 475354 A2 | 3/1992 | |
| EP | 0 791 652 A1 | 8/1997 | |
| EP | 1 400 171 A1 | 3/2004 | |
| EP | 1 985 633 A1 | 10/2008 | |
| EP | 2 292 273 A2 | 3/2011 | |
| EP | 1 945 665 B1 | 12/2011 | |
| FR | 2 861 080 A1 | 4/2005 | |
| JP | 9-506719 A | 7/1997 | |
| JP | 2002-512014 A | 4/2002 | |
| JP | 2003-521915 A | 7/2003 | |
| JP | 2006-507839 A | 3/2006 | |
| JP | 2007-533299 A | 11/2007 | |
| JP | 2008-515772 A | 5/2008 | |
| JP | 2009-507482 A | 2/2009 | |
| JP | 2009-512694 A | 3/2009 | |
| JP | 2009/538885 A | 11/2009 | |
| JP | 2010-502204 A | 1/2010 | |
| JP | 2003-534781 A5 | 8/2012 | |
| JP | 2012-528112 A | 11/2012 | |
| WO | WO 88/01648 A1 | 3/1988 | |
| WO | WO 90/04036 A1 | 4/1990 | |
| WO | WO 90/05188 A1 | 5/1990 | |
| WO | WO 91/08216 A1 | 6/1991 | |
| WO | WO 92/03918 A1 | 3/1992 | |
| WO | WO 93/12227 A1 | 6/1993 | |
| WO | WO 95/17085 A1 | 6/1995 | |
| WO | WO 95/24488 A1 | 9/1995 | |
| WO | WO 95/24494 A1 | 9/1995 | |
| WO | WO 95/24495 A1 | 9/1995 | |
| WO | WO 97/05771 A2 | 2/1997 | |
| WO | WO 97/07669 A1 | 3/1997 | |
| WO | WO 98/13378 A1 | 4/1998 | |
| WO | WO 98/54226 A1 | 12/1998 | |
| WO | WO 99/11773 A1 | 3/1999 | |
| WO | WO 99/54342 A1 | 10/1999 | |
| WO | WO 00/30436 A1 | 6/2000 | |
| WO | WO 01/00855 A1 | 1/2001 | |
| WO | WO 01/26455 A1 | 4/2001 | |
| WO | WO 01/57088 A1 | 8/2001 | |
| WO | WO 01/77181 A2 | 10/2001 | |
| WO | WO 02/30954 A1 | 4/2002 | |
| WO | WO 02/072636 A2 | 9/2002 | |
| WO | WO 03/035835 A2 | 5/2003 | |
| WO | WO 2004/048517 A2 | 6/2004 | |
| WO | WO 2004/050847 A2 | 6/2004 | |
| WO | WO 2006/014683 A2 | 2/2006 | |
| WO | WO 2006/088447 A1 | 8/2006 | |
| WO | WO 2006/088464 A2 | 8/2006 | |
| WO | WO 2007/005786 A2 | 1/2007 | |
| WO | WO 2007/029054 A1 | 3/2007 | |
| WO | WO-2007/048077 * | 4/2007 | ............ C07K 16/04 |
| WO | WO 2007/048077 A2 | 4/2007 | |
| WO | WO 2007/048122 A2 | 4/2007 | |
| WO | WO 2007/115813 A1 | 10/2007 | |
| WO | WO 2008/028686 A2 | 3/2008 | |
| WO | WO 2008/063982 A2 | 5/2008 | |
| WO | WO 2008/083150 A2 | 7/2008 | |
| WO | WO 2008/101177 A2 | 8/2008 | |
| WO | WO 2009/046168 A1 | 4/2009 | |
| WO | WO 2010/136492 A2 | 12/2010 | |
| WO | WO 2012/105699 A1 | 8/2012 | |
| WO | WO 2013/021279 A2 | 2/2013 | |
| WO | WO 2013/025079 A1 | 2/2013 | |
| WO | WO 2014/125374 A1 | 8/2014 | |
| WO | WO 2014/125377 A2 | 8/2014 | |

OTHER PUBLICATIONS

Awwad et al., Modification of monoclonal antibody carbohydrates by oxidation, conjugation, or deoxymannojirimycin does not interfere with antibody effector functions. Cancer Immunol Immunother. Jan. 1994;38(1):23-30.

Axford et al., Changes in normal glycosylation mechanisms in autoimmune rheumatic disease. J Clin Invest. Mar. 1992;89(3):1021-31.

Ayala et al., Production of plantibodies in Nicotiana plants. Methods Mol Biol. 2009;483:103-34. doi: 10.1007/978-1-59745-407-0_7.

Beck et al., Trends in glycosylation, glycoanalysis and glycoengineering of therapeutic antibodies and Fc-fusion proteins. Curr Pharm Biotechnol. Dec. 2008;9(6):482-501.

Bhol et al., AVX-470: a novel oral anti-TNF antibody with therapeutic potential in inflammatory bowel disease. Inflamm Bowel Dis. Oct. 2013;19(11):2273-81. doi: 10.1097/MIB.0b013e3182a11958.

Black et al., Serum and secretory IgA from HIV-infected individuals mediate antibody-dependent cellular cytotoxicity. Clin Immunol Immunopathol. Nov. 1996;81(2):182-90.

Boyd et al., The effect of the removal of sialic acid, galactose and total carbohydrate on the functional activity of Campath-1H. Mol Immunol. Dec. 1995;32(17-18):1311-8.

Bremel et al., Alteration of milk composition using molecular genetics. J Dairy Sci. Oct. 1989;72(10):2826-33.

Brunt, Molecular Farming: Transgenic Animals as Bioreactors. Bio/Technology. 1988;6(10):1149-54.

Cammuso et al., Hormonal induced lactation in transgenic goats. Anim Biotechnol. 2000;11(1):1-17.

Canfield et al., The binding affinity of human IgG for its high affinity Fc receptor is determined by multiple amino acids in the CH2 domain and is modulated by the hinge region. J Exp Med. 1991;173(6):1483-91.

Cartron et al., Therapeutic activity of humanized anti-CD20 monoclonal antibody and polymorphism in IgG Fc receptor FcgammaRIIIa gene. Blood. Feb. 1, 2002;99(3):754-8.

Chitlaru et al., Overloading and removal of N-glycosylation targets on human acetylcholinesterase: effects on glycan composition and circulatory residence time. Biochem J. May 1, 2002;363(Pt 3):619-31.

Chiu et al., In vivo targeting function of N-linked oligosaccharides with terminating galactose and N-acetylgalactosamine residues. J Biol Chem. Jun. 10, 1994;269(23):16195-202.

Chuang et al., Elimination of N-linked glycosylation sites from the human IgA1 constant region: effects on structure and function. J Immunol. Jan. 15, 1997;158(2):724-32.

Clark et al., Expression of Human Anti-Hemophilic Factor IX in the Milk of Transgenic Sheep. Biotechnology (N Y). 1989 (7):487-92.

Clark et al., Pharmaceuticals from Transgenic Livestock. Trends Bio Tech. 1987;5:20-4.

Clynes et al., Inhibitory Fc receptors modulate in vivo cytotoxicity against tumor targets. Nat Med. Apr. 2000;6(4):443-6.

Clynes et al., Fc receptors are required in passive and active immunity to melanoma. Proc Natl Acad Sci U S A. Jan. 20, 1998;95(2):652-6.

Dall'Ozzo et al., Rituximab-dependent cytotoxicity by natural killer cells: influence of FCGR3A polymorphism on the concentration-effect relationship. Cancer Res. Jul. 1, 2004;64(13):4664-9.

Davies et al., Expression of GnTIII in a recombinant anti-CD20 CHO production cell line: Expression of antibodies with altered glycoforms leads to an increase in ADCC through higher affinity for FC gamma RIII. Biotechnol Bioeng. Aug. 20, 2001;74(4):288-94.

(56) References Cited

OTHER PUBLICATIONS

Ditullio et al., Production of cystic fibrosis transmembrane conductance regulator in the milk of transgenic mice. Biotechnology (N Y). Jan. 1992;10(1):74-7.

Dorai et al., Aglycosylated chimeric mouse/human IgG1 antibody retains some effector function. Hybridoma. Apr. 1991;10(2):211-7.

Echelard et al., Production in the Milk of Transgenic Animals. A Validated, Cost-Effective Approach for the. Manufacturing of Complex Recombinant Protein. EuroBio 2009; 1-34.

Edmunds et al., Transgenically produced human antithrombin: Structural and functional comparison to human plasma-derived antithrombin. Blood. Jun. 15, 1998;91(12):4561-71.

Engelmann et al., Antibodies to a soluble form of a tumor necrosis factor (TNF) receptor have TNF-like activity. J Biol Chem. 1990;265(24):14497-504.

Fujii et al., Structural heterogeneity of sugar chains in immunoglobulin G. Conformation of immunoglobulin G molecule and substrate specificities of glycosyltransferases. J Biol Chem. Apr. 15, 1990;265(11):6009-18.

Gordon et al., Production of Human Tissue Plasminogen Activator in Transgenic Mouse Milk. Biotechnology (N Y). 1987 (5):1183-7.

Gottlieb et al., Deficient uridine diphosphate-N-acetylglucosamine:glycoprotein N-acetylglucosaminyltransferase activity in a clone of Chinese hamster ovary cells with altered surface glycoproteins. J Biol Chem. May 10, 1975;250(9):3303-9.

Hand et al., Comparative biological properties of a recombinant chimeric anti-carcinoma mAb and a recombinant aglycosylated variant. Cancer Immunol Immunother. 1992;35(3):165-74.

Hellström et al., T cell immunity to tumor antigens. Crit Rev Immunol. 1998;18(1-2):1-6.

Hishii et al., Studies of the mechanism of cytolysis by tumour-infiltrating lymphocytes. Clin Exp Immunol. Jun. 1999;116(3):388-94.

Hong et al., A humanized anti--4-1BB monoclonal antibody suppresses antigen-induced humoral immune response in nonhuman primates. J Immunother. Nov.-Dec. 2000;23(6):613-21.

Horiuchi et al., Transmembrane TNF-alpha: structure, function and interaction with anti-TNF agents. Rheumatology (Oxford). Jul. 2010;49(7):1215-28.

Horwitz et al., Secretion of functional antibody and Fab fragment from yeast cells. Proc Natl Acad Sci U S A. Nov. 1988;85(22):8678-82.

Houdebine, Production of pharmaceutical proteins from transgenic animals. J Biotechnol. May 31, 1994;34(3):269-87.

Houot et al., Boosting antibody-dependant cellular cytotoxicity against tumor cells with a CD137 stimulatory antibody. Oncoimmunology. Sep. 1, 2012;1(6):957-958.

Humphreys et al., Therapeutic antibody production technologies: molecules, applications, expression and purification. Curr Opin Drug Discov Devel. Mar. 2001;4(2):172-85.

James et al., N-glycosylation of recombinant human interferon-gamma produced in different animal expression systems. Biotechnology (N Y). Jun. 1995;13(6):592-6.

Jefferis et al., Recognition sites on human IgG for Fc gamma receptors: the role of glycosylation. Immunol Lett. 1995;44(2-3):111-7.

Jung et al., Aglycosylated IgG variants expressed in bacteria that selectively bind FcgammaRI potentate tumor cell killing by monocyte-dendritic cells. Proc Natl Acad Sci U S A. Jan. 12, 2010;107(2):604-9. Epub Dec. 18, 2009.

Koene et al., Fc gammaRIIIa-158V/F polymorphism influences the binding of IgG by natural killer cell Fc gammaRIIIa, independently of the Fc gammaRIIIa-48L/R/H phenotype. Blood. Aug. 1, 1997;90(3):1109-14.

Kumpel et al., Galactosylation of human IgG monoclonal anti-D produced by EBV-transformed B-lymphoblastoid cell lines is dependent on culture method and affects Fc receptor-mediated functional activity. Hum Antibodies Hybridomas. 1994;5(3-4): 143-51.

Lang et al., Chimeric CD19 antibody mediates cytotoxic activity against leukemic blasts with effector cells from pediatric patients who received T-cell-depleted allografts. Blood. May 15, 2004;103(10):3982-5. Epub Feb. 5, 2004.

Leatherbarrow et al., Effector functions of a monoclonal aglycosylated mouse IgG2a: binding and activation of complement component C1 and interaction with human monocyte Fc receptor. Mol Immunol. 1985;22(4):407-15.

Li et al., Structure of the altered oligosaccharide present in glycoproteins from a clone of Chinese hamster ovary cells deficient in N-acetylglucosaminyltransferase activity. J Biol Chem. Sep. 25, 1978;253(18):6426-31.

Limonta et al., Production of active anti-CD6 mouse/human chimeric antibodies in the milk of transgenic mice. Immunotechnology. Aug. 1995;1(2):107-13.

Lin et al., Fc-dependent expression of CD137 on human NK cells: insights into "agonistic" effects of anti-CD137 monoclonal antibodies. Blood. Aug. 1, 2008;112(3):699-707. Epub Jun. 2, 2008.

Lobuglio et al., Mouse/human chimeric monoclonal antibody in man: kinetics and immune response. Proc Natl Acad Sci U S A. Jun. 1989;86(11):4220-4.

Logan, Transgenic animals: beyond 'funny milk'. Curr Opin Biotechnol. Oct. 1993;4(5):591-5.

Louis et al., Association between polymorphism in IgG Fc receptor IIIa coding gene and biological response to infliximab in Crohn's disease. Aliment Pharmacol Ther. Mar. 1, 2004;19(5):511-9.

Lund et al., Control of IgG/Fc glycosylation: a comparison of oligosaccharides from chimeric human/mouse and mouse subclass immunoglobulin Gs. Mol Immunol. 1993;30(8):741-8.

Lund et al., Multiple interactions of IgG with its core oligosaccharide can modulate recognition by complement and human Fc gamma receptor I and influence the synthesis of its oligosaccharide chains. J Immunol. 1996;157(11):4963-9.

Lund et al., Oligosaccharide-protein interactions in IgG can modulate recognition by Fc gamma receptors. FASEB J. Jan. 1995;9(1):115-9.

Malaise et al., Evidence for a role of accessible galactosyl or mannosyl residues of Fc domain in the in vivo clearance of IgG antibody-coated autologous erythrocytes in the rat. Clin Immunol Immunopathol. 1990;54(3):469-83.

Malhotra et al., Glycosylation changes of IgG associated with rheumatoid arthritis can activate complement via the mannose-binding protein. Nat Med. 1995;1(3):237-43.

Mattu et al., The glycosylation and structure of human serum IgA1, Fab, and Fc regions and the role of N-glycosylation on Fc alpha receptor interactions. J Biol Chem. Jan. 23, 1998;273(4):2260-72.

Maynard et al., Antibody engineering. Annu Rev Biomed Eng. 2000;2:339-76.

Meade et al., Expression of recombinant proteins in milk of transgenic animals. Gene Expression Systems. Jan. 1, 1999:399-427.

Mimura et al., Role of Oligosaccharide residues of IgG1-Fc in Fc gamma RIIb binding. J Biol Chem 2001; 276(49): 45539-47.

Mimura et al., The influence of glycosylation on the thermal stability and effector function expression of human IgG1-Fc: properties of a series of truncated glycoforms. Mol Immunol. 2000;37(12-13):697-706.

Mizuochi et al., Structural and numerical variations of the carbohydrate moiety of immunoglobulin G. J Immunol. Nov. 1982;129(5):2016-20.

Mullins et al., Perspectives Series: Molecular Medicine in Genetically engineered Animals. J Clin Invest. Sep. 1996;98(11):S37-40.

Niwa et al., Enhanced natural killer cell binding and activation by low-fucose IgG1 antibody results in potent antibody-dependent cellular cytotoxicity induction at lower antigen density. Clin Cancer Res. Mar. 15, 2005;11(6):2327-36.

Niwa et al., Enhancement of the antibody-dependent cellular cytotoxicity of low-fucose IgG1 Is independent of FcgammaRIIIa functional polymorphism. Clin Cancer Res. Sep. 15, 2004;10(18 Pt 1):6248-55.

Niwa et al., Defucosylated chimeric anti-CC chemokine receptor 4 IgG1 with enhanced antibody-dependent cellular cytotoxicity shows potent therapeutic activity to T-cell leukemia and lymphoma. Cancer Res. Mar. 15, 2004;64(6):2127-33.

(56) References Cited

OTHER PUBLICATIONS

Nose et al., Biological significance of carbohydrate chains on monoclonal antibodies. Proc Natl Acad Sci USA. 1983;80(21):6632-6.
Okazaki et al., Fucose depletion from human IgG1 oligosaccharide enhances binding enthalpy and association rate between IgG1 and FcgammaRIIIa. J Mol Biol. Mar. 5, 2004;336(5):1239-49.
Parekh et al., Association of rheumatoid arthritis and primary osteoarthritis with changes in the glycosylation pattern of total serum IgG. Nature. 1985;316(6027):452-7.
Pollock et al. Transgenic milk as a method for the production of recombinant antibodies. J Immunol Methods. Dec. 10, 1999;231(1-2):147-57.
Pound et al., Aglycosylated chimaeric human IgG3 can trigger the human phagocyte respiratory burst. Mol Immunol. Feb. 1993;30(3):233-41.
Pursel et al., Status of research with transgenic farm animals. J Anim Sci. 1993;71 Suppl 3:10-19.
Rademacher et al., Glycobiology. Annu Rev Biochem. 1988;57:785-838.
Rademacher et al., Immunoglobulin G as a glycoprotein. Biochem Soc Symp. 1986;51:131-48.
Rademacher, Glycosylation as a factor affecting product consistency. Biologicals. Jun. 1993;21(2):103-4.
Rademacher et al., The role of IgG glycoforms in the pathogenesis of rheumatoid arthritis. Springer Semin Immunopathol. 1988;10(2-3):231-49.
Raju et al., Species-specific variation in glycosylation of IgG: evidence for the species-specific sialylation and branch-specific galactosylation and importance for engineering recombinant glycoprotein therapeutics. Glycobiology. May 2000;10(5):477-86.
Raju, Glycosylation Variations with Expression Systems and Their Impact on Biological Activity of Therapeutic Immunoglobulins. BioProcess International. 2003;1(4):44-53.
Raju, Terminal sugars of Fc glycans influence antibody effector functions of IgGs. Curr Opin Immunol. Aug. 2008;20(4):471-8. Epub Jul. 17, 2008.
Reff et al., Depletion of B cells in vivo by a chimeric mouse human monoclonal antibody to CD20. Blood. Jan. 15, 1994;83(2):435-45.
Rothman et al., Antibody-dependent cytotoxicity mediated by natural killer cells is enhanced by castanospermine-induced alterations of IgG glycosylation. Mol Immunol. Dec. 1989;26(12):1113-23.
Rudd et al., Diversification of the IgG molecule by oligosaccharides. Mol Immunol. Dec. 1991;28(12):1369-78.
Sazinsky et al., Aglycosylated immunoglobulin G1 variants productively engage activating Fc receptors. Proc Natl Acad Sci U S A. Dec. 23, 2008;105(51):20167-72. Epub Dec. 12, 2008.
Schneider, Texas Researchers Develop 4 Gene-Altered Calves. The New York Times National. Jun. 8, 1990.
Schnieke et al., Human factor IX transgenic sheep produced by transfer of nuclei from transfected fetal fibroblasts. Science. 1997;278:2130-3.
Schuurman et al., The inter-heavy chain disulfide bonds of IgG4 are in equilibrium with intra-chain disulfide bonds. Mol Immunol. Jan. 2001;38(1):1-8.
Seamark, Progress and emerging problems in livestock transgenesis: a summary perspective. Reprod Fertil Dev. 1994;6(5):653-7.
Selgrath et al., Collection and transfer of microinjectable embryos from dairy goats. Theriogenology. 1990;34(6):1195-205.
Shields et al., High resolution mapping of the binding site on human IgG1 for Fc gamma RI, Fc gamma RII, Fc gamma RIII, and FcRn and design of IgG1 variants with improved binding to the Fc gamma R. J Biol Chem. Mar. 2, 2001;276(9):6591-604. Epub Nov. 28, 2000.
Shields et al., Lack of fucose on human IgG1 N-linked oligosaccharide improves binding to human Fcgamma RIII and antibody-dependent cellular toxicity. J Biol Chem. Jul. 26, 2002;277(30):26733-40. Epub May 1, 2002.

Shim et al., One target, different effects: a comparison of distinct therapeutic antibodies against the same targets. Exp Mol Med. Oct. 31, 2011;43(10):539-49.
Simmons et al., Expression of full-length immunoglobulins in *Escherichia coli*: rapid and efficient production of aglycosylated antibodies. J Immunol Methods. May 1, 2002;263(1-2):133-47.
Simons et al., Gene Transfer into Sheep. Bio/Technology. 1998;6:179-83.
Sola et al., Transgenic mice secreting coronavirus neutralizing antibodies into the milk. J Virol. May 1998;72(5):3762-72.
Soulier et al., Expression analysis of ruminant alpha-lactalbumin in transgenic mice: developmental regulation and general location of important cis-regulatory elements. FEBS Lett. Feb. 3, 1992;297(1-2):13-8.
Stanley et al., Chinese hamster ovary cells selected for resistance to the cytotoxicity of phytohemagglutinin are deficient in a UDP-N-acetylglucosamine--glycoprotein N-acetylglucosaminyltransferase activity. Proc Natl Acad Sci U S A. Sep. 1975;72(9):3323-7.
Stanley, Glycosylation mutants of animal cells. Annu Rev Genet. 1984;18:525-52.
Stockwin et al., The role of therapeutic antibodies in drug discovery. Biochem Sac Trans. 2003;31(2):433-6.
Sumar et al., Analysis of glycosylation changes in IgG using lectins. J Immunol Methods. Jul. 20, 1990;131(1):127-36.
Takeuchi et al., A novel mutation in the FcgammaRIIIA gene (CD16) results in active natural killer cells lacking CD16. Autoimmunity. 1999;31(4):265-71.
Tamada et al., Renewed interest in cancer immunotherapy with the tumor necrosis factor superfamily molecules. Cancer Immunol Immunother. Apr. 2006;55(4):355-62. Epub Sep. 27, 2005.
Tamamori et al., Granulocyte-colony stimulating factor enhances chimeric antibody Nd2 dependent cytotoxicity against pancreatic cancer mediated by polymorphonuclear neutrophils. Int J Oncol. Sep. 2002;21(3):649-54.
Tan et al., Influence of the hinge region on complement activation, C1q binding, and segmental flexibility in chimeric human immunoglobulins. Proc Natl Acad Sci USA. Jan. 1990;87(1):162-6.
Tandai et al., Structural study of the sugar moieties of monoclonal antibodies secreted by human-mouse hybridoma. Arch Biochem Biophys. 1991;291(2):339-48.
Tao et al., Studies of aglycosylated chimeric mouse-human IgG. Role of carbohydrate in the structure and effector functions mediated by the human IgG constant region. J Immunol. Oct. 15, 1989;143(8):2595-601.
Tarentino et al., The release of intact oligosaccharides from specific glycoproteins by endo-beta-N-acetylglucosaminidase H. J Biol Chem. Feb. 10, 1974;249(3):818-24.
Theofilopoulos et al., Tumour necrosis factor and other cytokines in murine lupus. Ann Rheum Dis. Nov. 1999;58 Suppl 1:I49-55.
Thornburg et al., Carbohydrate-mediated clearance of immune complexes from the circulation. A role for galactose residues in the hepatic uptake of IgG-antigen complexes. J Biol Chem. Jul. 25, 1980;255(14):6820-5.
Topalian et al., Tumor-specific cytolysis by lymphocytes infiltrating human melanomas. J Immunol. May 15, 1989;142(10):3714-25.
Treon et al., Polymorphisms in FcgammaRIIIA (CD16) receptor expression are associated with clinical response to rituximab in Waldenström's macroglobulinemia. J Clin Oncol. Jan. 20, 2005;23(3):474-81.
Tsuchiya et al., Effects of galactose depletion from oligosaccharide chains on immunological activities of human IgG. J Rheumatol. 1989;16(3):285-90.
Van Kuik-Romeijn et al., Expression of a functional mouse-human chimeric anti-CD19 antibody in the milk of transgenic mice. Transgenic Res. Apr. 2000;9(2):155-9.
Walker et al., Aglycosylation of human IgG1 and IgG3 monoclonal antibodies can eliminate recognition by human cells expressing Fc gamma RI and/or Fc gamma RII receptors. Biochem J. Apr. 15, 1989;259(2):347-53.
Wall, Transgenic Livestock: Progress and Prospects for the Future. Theriogenology. 1996;45:57-68.

(56) References Cited

OTHER PUBLICATIONS

Ward et al., Characterization of humanized antibodies secreted by Aspergillus niger. Appl Environ Microbiol. May 2004;70(5):2567-76.
Weidle et al., Genes encoding a mouse monoclonal antibody are expressed in transgenic mice, rabbits and pigs. Gene. Feb. 15, 1991;98(2):185-91.
Wolff et al., Monoclonal antibody homodimers: enhanced antitumor activity in nude mice. Cancer Res. Jun. 1, 1993;53(11):2560-5.
Wright et al., Effect of altered CH2-associated carbohydrate structure on the functional properties and in vivo fate of chimeric mouse-human immunoglobulin G1. J Exp Med. Sep. 1, 1994;180(3):1087-96.
Wright et al., Effect of C2-associated carbohydrate structure on Ig effector function: studies with chimeric mouse-human IgG1 antibodies in glycosylation mutants of Chinese hamster ovary cells. J Immunol. Apr. 1, 1998;160(7):3393-402.
Wu et al., A novel polymorphism of FcgammaRIIIa (CD16) alters receptor function and predisposes to autoimmune disease. J Clin Invest. Sep. 1, 1997;100(5):1059-70.
Yamane-Ohnuki et al., Establishment of FUT8 knockout Chinese hamster ovary cells: an ideal host cell line for producing completely defucosylated antibodies with enhanced antibody-dependent cellular cytotoxicity. Biotechnol Bioeng. Sep. 5, 2004;87(5):614-22.
Yom et al., Genetic engineering of milk composition: modification of milk components in lactating transgenic animals. Am J Clin Nutr. Aug. 1993;58(2 Suppl):299S-306S.
Zhou et al., Effect of genetic background on glycosylation heterogeneity in human antithrombin produced in the mammary gland of transgenic goats. J Biotechnol. Apr. 20, 2005;117(1):57-72.
[No Author Listed] GTC Biotherapeutics and LFB Biotechnologies Enter Strategic Collaboration for Recombinant Plasma Proteins and Monoclonal Antibodies. Press Release; Oct. 2, 2006. Last accessed from <https://www.businesswire.com/news/home/20061002005515/en/GTC-Biotherapeutics-LFB-Biotechnologies-Enter-Strategic-Collaboration> on Jan. 19, 2018.
[No Author Listed] HERCEPTIN® Trastuzumab. Genentech, Inc.; US Package Insert. Sep. 1998.
[No Author Listed] Trastuzumab. Wikipedia. Oct. 30, 2012.
Alzari, P.M. et al., Three-Dimensional Structure of Antibodies. Ann. Rev. Immunol. 1988 6: 555-580.
Arora et al., Differences in binding and effector functions between classes of TNF antagonists. Cytokine. 2009;45:124-131.
Baguisi et al., Production of goats by somatic cell nuclear transfer. Nat Biotechnol. May 1999;17(5):456-61.
Bendig, Humanization of Rodent Monoclonal Antibodies by CDR Grafting. Companion to Methods in Enzymology. 1995;8:83-93.
Bertolini et al., The transgenic animal platform for biopharmaceutical production. Transgenic Res. Jun. 2016;25(3):329-43. doi: 10.1007/s11248-016-9933-9. Epub Jan. 28, 2016.
Bird et al,. Single-chain antigen-binding proteins. (1988) Science. 242: 423-426. Abstract only.
Blanchard et al., N-glycosylation and biological activity of recombinant human alpha1-antitrypsin expressed in a novel human neuronal cell line. Biotechnol Bioeng. Sep. 2011;108(9):2118-28. doi: 10.1002/bit.23158. Epub Apr. 20, 2011.
Bookman et al., Evaluation of monoclonal humanized anti-HER2 antibody, trastuzumab, in patients with recurrent or refractory ovarian or primary peritoneal carcinoma with overexpression of HER2: a phase II trial of the Gynecologic Oncology Group. J Clin Oncol. Jan. 15, 2003;21(2):283-90.
Borsig et al., Heparin and cancer revisited: mechanistic connections involving platelets, P-selectin, carcinoma mucins, and tumor metastasis. Proc Natl Acad Sci U S A. Mar. 13, 2001;98(6):3352-7.
Bosques et al., Chinese hamster ovary cells can produce galactose-α-1,3-galactose antigens on proteins. Nat Biotechnol. Nov. 2010;28(11):1153-6. doi: 10.1038/nbt1110-1153. Author manuscript.

Brink et al., Developing Efficient Strategies for the Generation of Transgenic Cattle Which Produce Biopharmaceuticals in Milk. Theriogenology. 2000;53:139-48.
Brinster et al., Introduction of genes into the germ line of animals. Harvey Lect. 1984-1985;80:1-38. Author manuscript.
Bühler et al., Rabbit beta-casein promoter directs secretion of human interleukin-2 into the milk of transgenic rabbits. Biotechnology (N Y). Feb. 1990;8(2):140-3.
Cabanes-Macheteau et al., N-Glycosylation of a mouse IgG expressed in transgenic tobacco plants. Glycobiology. Apr. 1999;9(4):365-72.
Campbell et al., Nuclear-cytoplasmic interactions during the first cell cycle of nuclear transfer reconstructed bovine embryos: implications for deoxyribonucleic acid replication and development. Biology of Reproduction. 1993;49(5):933-42.
Carter, Introduction to current and future protein therapeutics: a protein engineering perspective. Exp Cell Res. May 15, 2011;317(9):1261-9. Doi: 10.1016/j.yexcr.2011.02.013. Epub Mar. 1, 2011.
Carton et al., Codon engineering for improved antibody expression in mammalian cells. Protein Expr Purif. Oct. 2007;55(2):279-86. Epub Jun. 16, 2007.
Cassinotti et al., Adalimumab for the treatment of Crohn's disease. Biologics. Dec. 2008;2(4):763-77.
Castro et al., Transgenic rabbits for the production of biologically-active recombinant proteins in the milk Genet Anal. Nov. 1999;15(3-5):179-87.
Church et al., Embryo manipulation and gene transfer in livestock. Can J Anim Schi Sep. 1985;65:527-538.
Cianga et al. Identification and function of neonatal Fc receptor in mammary gland of lactating mice. Eur. J. Immunol. 1999; 29:2515-23.
Clark et al., Assessing unintended effects of a mammary-specific transgene at the whole animal level in host and non-target animals. Transgenic Research. 2014;23:245-256.
Clark et al., Protein Purification of Bio-Synthetic Spider Silk. Utah State University. Apr. 2012. Available online at https://works.bepress.com/candace_clark/2/. Last accessed on Jan. 30, 2018. 2 pages.
Clark, The mammary gland as a bioreactor: expression, processing, and production of recombinant proteins. J Mammary Gland Biol Neoplasia. Jul. 1998;3(3):337-50. Review.
Colcher et al., Effects of Genetic Engineering on the Pharmacokinetics of Antibodies. QJ Nucl Med 1999; 43:132-9.
Cole et al., Glycosylation Patterns of Human Proteins Expressed in Transgenic Goat Milk. Journal of Cellular Biochemistry. 1994, Suppl. 18D, p. 265, Ab. U100, published online Feb. 19, 1994.
Colman, Dolly, Polly and other 'ollys': likely impact of cloning technology on biomedical uses of livestock. Genet Anal. Nov. 1999;15(3-5):167-73.
Commins et al., Anaphylaxis syndromes related to a new mammalian cross-reactive carbohydrate determinant. J Allergy Clin Immunol. Oct. 2009;124(4):652-7.
Commins et al., Delayed anaphylaxis, angioedema, or urticaria after consumption of red meat in patients with IgE antibodies specific for galactose-alpha-1,3-galactose. J Allergy Clin Immunol. Feb. 2009;123(2):426-33.
Crowe et al., Humanized Monoclonal Antibody CAMPATH-1H: Myeloma Cell Expression of Genomic Constructs, Nucleotide Sequence of cDNA Constructs and Comparison of Effector Mechanisms of Myeloma and Chinese Hamster Ovary Cell Derived Material. Clin Exp Immunol. Jan. 1992;87(1):105-10.
Dai et al., Targeted Disruption of the α1,3-Galactosyltransferase Gene in Cloned Pigs. Nature Biotechnology. Mar. 2002;20:251-5.
Dalrymple et al., Genetically modified livestock for the production of human proteins in milk. Biotechnol Genet Eng Rev. 1998;15:33-49. Review.
Davis et al., Single Chain Antibody (SCA) Encoding Genes: One-Step Construction and Expression in Eukaryotic Cells. Bio/Technol. 1991;9:165-69.
Defazio-Eli et al., Quantitative assays for the measurement of HER1-HER2 heterodimerization and phosphorylation in cell lines and breast tumors: applications for diagnostics and targeted drug mechanism of action. Breast Cancer Res. Apr. 15, 2011;13(2):R44.

(56) References Cited

OTHER PUBLICATIONS

Drohan, The past, present and future of transgenic bioreactors. Thromb Haemost. Jul. 1997;78(1):543-7.
Ebert et al., Transgenic production of a variant of human tissue-type plasminogen activator in goat milk: generation of transgenic goats and analysis of expression. Biotechnology (N Y). Sep. 1991;9(9):835-8.
Echelard et al., Chapter 11. The First Biopharmaceutical from Transgenic Animals: ATryn®. In Modern Biopharmaceuticals: Design, Development and Optimization, eds. J. Knablein and R. H. Miler. 2005;1-26.
Echelard et al., Chapter 24: Protein production in transgenic animals. S.C. Makrides, ed., Gene Transfer and Expression in Mammalian Cells. 2003:625-639.
Echelard, Recombinant protein production in transgenic animals. Curr Opin Biotechnol. Oct. 1996;7(5):536-40. Review.
Edmunds et al., Tissue Specific and Species Differences in the Glycosylation Pattern of Antithrombin III, Journal of Cellular Biochemistry, Abstract U102, pp. 265 (1994).
Fan et al., Heterogeneity of recombinant human antithrombin III expressed in baby hamster kidney cells. Effect of glycosylation differences on heparin binding and structure. J Biol Chem. Aug. 15, 1993;268(23):17588-96.
Federspiel et al., Hybridoma Antibody Production In Vitro In Type II SerumFree Medium Using Nutridoma-SP Supplements: Comparisons With In Vivo Methods. J Immunol Methods. 1991;145(1-2):213-221.
Fernandes, Demonstrating Comparability of Antibody Glycosylation during Biomanufacturing. European Biopharmaceutical Review. Summer 2005: 106-10.
Forthal et al., Recombinant gp120 vaccine-induced antibodies inhibit clinical strains of HIV-1 in the presence of Fc receptor-bearing effector cells and correlate inversely with HIV infection rate. J Immunol. May 15, 2007;178(10):6596-603.
Gee et al., Human breast cancer tumor models: molecular imaging of drug susceptibility and dosing during HER2/neu-targeted therapy. Radiology. Sep. 2008;248(3):925-35.
Ghetie et al., FcRn: the MHC class I-related receptor that is more than an IgG transporter. Immunol Today. Dec. 1997;18(12):592-8.
Gil et al., Analysis of the N-glycans of recombinant human Factor IX purified from transgenic pig milk. Glycobiology. Jul. 2008;18(7):526-39.
Goeddel, Systems for Heterologous Gene Expression. Methods in Enzymology. 1990;185:3-7.
Goodarzi et al., Decreased branching, increased fucosylation and changed sialylation of alpha-1-proteinase inhibitor in breast and ovarian cancer. Clin Chim Acta. May 15, 1995;236(2):161-71.
Gordon et al., Gene transfer into mouse embryos. Dev Biol (N Y 1985). 1986;4:1-36. Review.
Gramer et al., Modulation of antibody galactosylation through feeding of uridine, manganese chloride, and galactose. Biotechnol Bioeng. Jul. 2011;108(7):1591-602. doi: 10.1002/bit.23075. Epub Feb. 18, 2011.
Grönlund et al., The carbohydrate galactose-alpha-1,3-galactose is a major IgE-binding epitope on cat IgA. J Allergy Clin Immunol. May 2009;123(5):1189-91.
Guile et al., A rapid high-resolution high-performance liquid chromatographic method for separating glycan mixtures and analyzing oligosaccharide profiles. Anal Biochem. Sep. 5, 1996;240(2):210-26.
Hauschild et al., Efficient Generation of a Biallelic Knockout in Pigs Using Zinc-Finger Nucleases. PNAS. Jul. 19, 2011;108(29):12013-12017.
Heavey, U.S. Approves First Drug from DNA-Altered Animals. Reuters Science News. Http://reuters.com/article/us-gtc-atryn-idUSTRE51540E20090206. [dated Feb. 6, 2009; last accessed May 16, 2017].
Hernandez-Ilizaliturri et al., Neutrophils contribute to the biological antitumor activity of rituximab in a non-Hodgkin's lymphoma severe combined immunodeficiency mouse model. Clin Cancer Res. Dec. 1, 2003;9(16 Pt 1):5866-73.
Hobbs et al., Complex Hormonal Regulation of Rat Casein Gene Expression. Journal of Biological Chemistry. Apr. 10, 1982;257(7):3598-605.
Hodoniczky et al., Control of recombinant monoclonal antibody effector functions by Fc N-glycan remodeling in vitro. Biotechnol Prog. Nov.-Dec. 2005;21(6):1644-52.
Holl et al., Antibody-Mediated Fcγ Receptor-Based Mechanisms of HIV Inhibition: Recent Findings and New Vaccination Strategies. Viruses. Dec. 2009;1(3):1265-94. doi: 10.3390/v1031265. Epub Dec. 15, 2009.
Holliger et al., Diabodies: small bivalent and bispecific antibody fragments. Proc. Natl. Acad. Sci. USA. 1993;90:6444-6448.
Hong et al., Substitution of glutamine by glutamate enhances production and galactosylation of recombinant IgG in Chinese hamster ovary cells. Appl Microbiol Biotechnol. Oct. 2010;88(4):869-76. doi: 10.1007/s00253-010-2790-1. Epub Aug. 3, 2010.
Houde et al., Post-translational modifications differentially affect IgG1 conformation and receptor binding. Molecular & Cellular Proteomics. Aug. 2010;9(8):1716-28.
Houdebine, The production of pharmaceutical proteins from the milk of transgenic animals. Reprod Nutr Dev. 1995;35(6):609-17.
Houdebine, Transgenic animal bioreactors. Transgenic Res. 2000;9(4-5):305-20.
Huston et al., Protein engineering of antibody binding sites: recovery of specific activity in an anti-digoxin single-chain Fv analogue produced in *Escherichia coli*. Proc Natl Acad Sci U S A. Aug. 1988;85(16):5879-83.
Jacquenet et al., Mammalian meat-induced anaphylaxis: clinical relevance of anti-galactose-alpha-1,3-galactose IgE confirmed by means of skin tests to cetuximab. J Allergy Clin Immunol. Sep. 2009;124(3):603-5.
Jain et al., Targeted inactivation of Gα1 does not alter cardiac function or β-adrenergic sensitivity. Am J Physiol Heart Circ Physiol. 2001;280:H569-H575.
Jänne et al., Transgenic animals as bioproducers of therapeutic proteins. Ann Med. Aug. 1992;24(4):273-80.
Jänne et al., Transgenic bioreactors. Int J Biochem. Jul. 1994;26(7):859-70.
Jones et al., Ectopic Correction of Ornithine Transcarbamylase Deficiency in Sparse Fur Mice. Journal of Biological Chemistry. Aug. 25, 1990;265(24):14684-14690.
Junghans et al., The protection receptor for IgG catabolism is the β2-microglobulin-containing neonatal intestinal transport receptor. Proc. Natl. Acad. Sci. USA. 1996;93(11):5512-6.
Junghans, Finally! The Brambell Receptor (FcRB): Mediator of Transmission of Immunity and Protection from Catabolism for IgG, Immunol Res. Feb. 1997;16(1):29-57.
Kacskovics, Fc receptors in livestock species. Vet Immunol Immunopathol. Dec. 28, 2004;102(4):351-62.
Kasinathan et al., Effect of Fibroblast Donor Cell Age and Cell Cycle on Development of Bovine Nuclear Transfer Embryos in Vitro. Biology of Reproduction. 2001;64:1487-1493.
Kerr et al., The bladder as a bioreactor: Urothelium production and secretion of growth hormone into urine. Nature Biotechnology. Jan. 1998;16(1):75-9.
Khodarovich et al., Expression of Eukaryotic Recombinant Proteins and Deriving Them from the Milk of Transgenic Animals. Applied Biology and Microbiology. 2013;49(9);711-22.
Kim et al., Catabolism of the murine IgG1 molecule: evidence that both CH2—CH3 domain interfaces are required for persistence of IgG1 in the circulation of mice. Scand J Immunol. 1994;40(4):457-65.
Kipps et al., Importance of immunoglobulin isotype in human antibody-dependent, cell-mediated cytotoxicity directed by murine monoclonal antibodies. J Exp Med. Jan. 1, 1985;161(1):1-17.
Köhler et al., Continuous cultures of fused cells secreting antibody of predefined specificity. Nature. Aug. 7, 1975;256(5517):495-7.
Lanteri et al., Designing a HER2/neu Promotor to Drive α1,3Galactosyltransferase Expression for Targeted Anti-αGalantibody-Mediated Tumor Cell Killing. Breast Cancer Research. 2005;7:R487-94.

(56) References Cited

OTHER PUBLICATIONS

Lantto et al., Chain Shuffling to Modify Properties of Recombinant Immunoglobulins. Methods Mol. Biol. (2002) 178: 303-316.

Lathe et al., Novel products from livestock. Exploiting New Technologies in animal breeding: Genetic developments. 1986:91-102.

Leach et al., Isolation from Human Placenta of the IgG Transporter, FcRn, and Localization to the Syncytiotrophoblast: Implications for Maternal-Fetal Antibody Transport, J. Immunology, (1996) 157(8): 3317-3322.

Lee et al., Production of biomedical proteins in the milk of transgenic dairy cows: the state of the art. Journal of Controlled Release. 1994;29:213-231.

Lee et al., Production of Recombinant Human Von Zillebrand Factor in the Milk of Transgenic Pigs. J of Reprod. Dev. 2009;55(5):484-490.

Liao et al., Design of Transgenes for Efficient Expression of Active Chimeric Proteins on Mammalian Cells. Biotechnology and Bioengineering. May 20, 2001;73(4):313-23.

Lifely et al., Glycosylation and biological activity of CAMPATH-1H expressed in different cell lines and grown under different culture conditions. Glycobiology. Dec. 1995;5(8):813-22.

Listinsky et al., P2-18-06: Conventional Trastuzumab Is an Antagonist of Natural Killer Cells: Making the Case for Fucose-Depleted Trastuzumab. Cancer Res. 2011;71(24 Suppl):Abstract nr P2-18-06.

Liu et al., A comparison of herpes simplex virus specific antibodies found in human milk and serum. Pediatr Res. Jun. 1992;31(6):591-5.

Loveil-Badge et al., Transgenic animals: new advances in the field. Nature. Jun. 20, 1985;315:628-29.

Lu et al., Over-expression of the bovine FcRn in the mammary gland results in increased IgG levels in both milk and serum of transgenic mice. Immunology. 2007;122(3):401-408.

Lusch et al., Development and Analysis of Alpha 1-Antitrypsin Neoglycoproteins: The Impact of Additional N-Glycosylation Sites on Serum Half-Life. Molecular Pharmaceutics. Jul. 1, 2013;10(7)2616-29.

Maga et al., Mammary Gland Expression of Transgenes and the Potential for Altering the Properties of Milk. Nature Biotechnology. 1995;(13):1452-7.

Magdelaine-Beuzelin et al., Structure-function relationships of the variable domains of monoclonal antibodies approved for cancer treatment. Crit Rev Oncol Hematol. Dec. 2007;64(3):210-25.

Mayer et al., Redistribution of the sheep neonatal Fc receptor in the mammary gland around the time of parturition in ewes and its localization in the small intestine of neonatal lambs. Immunology. Nov. 2002;107(3):288-96.

McGrane et al., Matebolic control of gene expression: in vivo studies with transgenic mice. Trands Biochem Sci. Jan. 1992;17(1):40-44.

Meade et al., Bovine alpha S1-casein gene sequences direct high level expression of active human urokinase in mouse milk. Biotechnology (N Y). May 1990;8(5):443-6.

Melican et al., Effect of serum concentration, method of trypsinization and fusion/activation utilizing transfected fetal cells to generate transgenic dairy goats by somatic cell nuclear transfer. Theriogenology. Apr. 1, 2005;63(6):1549-63.

Mitoma et al., Mechanisms for cytotoxic effects of anti-tumor necrosis factor agents on transmembrane tumor necrosis factor alpha-expressing cells: comparison among infliximab, etanercept, and adalimumab. Arthritis and Rheumatism. May 2008;58(5):1248-1257.

Morgan et al., Designing Biobetter Monoclonal Antibody Therapeutics by Glycoengineering. International Pharmaceutical Industry. 2009. 5 pages.

Morisset et al., Anaphylaxis to pork kidney is related to IgE antibodies specific for galactose-alpha-1,3-galactose. Allergy. May 2012;67(5):699-704.

Moura et al., Production of Recombinant Proteins in Milk of Transgenic and Non-Transgenic Goats. Brazilian Archives of Biology and Technology. Sep. 2011;54(5):927-38.

Nagy et al., Targeted mutagenesis: analysis of phenotype without germ line transmission. J Clin Invest. Mar. 15, 1996;97(6):1360-1365.

Niemann et al., Transgenic Livestock: premises and promises. Animal Reproduction Science. 2000;60-61:277-293.

Ober et al., Exocytosis of IgG as mediated by the receptor, FcRn: an analysis at the single-molecule level. Proc Natl Acad Sci USA. Jul. 27, 2004;101(30):11076-11081.

Ober et al., Differences in promiscuity for antibody-FcRn interactions across species: implications for therapeutic antibodies. Int Immunol. Dec. 2001;13(12):1551-9.

Okayama et al., A cDNA Cloning Vector That Permits Expression of cDNA Inserts in Mammalian Cells. Molecular and Cellular Biology. Feb. 1983;3(2):280-289.

Ongeri et al., Development of Goat Embryos after in Vitro Fertilization and Parthenogenetic Activation by Different Methods. Theriogenology. 2001;55:1933-1945.

Packer et al., A general approach to desalting oligosaccharides released from glycoproteins. Glycoconj J. Aug. 1998;15(8):737-47.

Padlan, Anatomy of the Antibody Molecule. Mol. Immunol. 1994;31(3):169-217.

Palmiter et al., Germ-line transformation of mice. Annu Rev Genet. 1986;20:465-99. Review.

Pantschenko et al., Establishment and characterization of a caprine mammary epithelial cell line (CMEC). In Vitro Cell Dev Biol Anim. Jan. 2000;36(1):26-37. Abstract only.

Papac et al., A high-throughput microscale method to release N-linked oligosaccharides from glycoproteins for matrix-assisted laser desorption/ionization time-of-flight mass spectrometric analysis. Glycobiology. 1998;8(5):445-454.

Park et al., Recombinant Human Erythropoietin Produced in Milk of Transgenic Pigs. Journal of Biotechnology. Apr. 10, 2006;122(3):362-71.

Patton et al., Intramammary infusion technique for genetic engineering of the mammary gland. Journal of dairy science. 1984;(67):1323-6.

Paul, Fundamental Immunology. 3rd edition. Chapter 9: Structure and Function of Immunoglobulins. 1993:292-295.

Poljak et al., Production and structure of diabodies. Structure. 1994;2:1121-1123.

Praetor et al., beta(2)-Microglobulin is important for cell surface expression and pH-dependent IgG binding of human FcRn. J Cell Sci. Jun. 1, 2002;115(Pt 11):2389-97.

Qian et al., Structural characterization of N-linked oligosaccharides on monoclonal antibody cetuximab by the combination of orthogonal matrix-assisted laser desorption/ionization hybrid quadrupole-quadrupole time-of-flight tandem mass spectrometry and sequential enzymatic digestion. Anal Biochem. May 1, 2007;364(1):8-18.

Rafiq et al., Immune complex-mediated antigen presentation induces tumor immunity. J Clin.Invest. Jul. 2002;110(1):71-9.

Regalado, Building a Better Goat. MIT Technology Review. Oct. 20, 2010. Available online at https://www.technologyreview.com/s/421268/building-a-better-goat/. Last accessed on Mar. 19, 2014. 2 pages.

Robak et al., New anti-CD20 monoclonal antibodies for the treatment of B-cell lymphoid malignancies. BioDrugs. Feb. 1, 2011;25(1):13-25. doi: 10.2165/11539590-000000000-00000.

Robak, GA-101, a third generation, humanized and glycoengineered ant-CD20 mAb for the treatment of B-cell lymphoid malignancies. Current Opinion in Investigational Drugs. Jun. 2009;10(6):588-596.

Sakai et al., Recombination and transcription of the endogenous Ig heavy chain locus is effected by the Ig heavy chain itronic enhancer core region in the absence of the matrix attachment regions. Proc. Natl. Acad. Sci. USA. Feb. 1999;96:1526-1531.

Salamone et al., High level expression of bioactive recombinant human growth hormone in the milk of a cloned transgenic cow. J Biotechnol. Jul. 13, 2006;124(2):469-72. Epub May 23, 2006.

Samiec et al., Transgenic Mammalian Species, Generated by Somatic Cell Cloning, in Biomedicine, Biopharmaceutical Industry and Human Nutrition/Dietetics—Recent Acheivements. Polish Journal of Veterinary Sciences. 2011;14(2):317-28.

(56) References Cited

OTHER PUBLICATIONS

Samuelsson et al., Anti-inflammatory activity of IVIG mediated through the inhibitory Fc receptor. Science. Jan. 19, 2001;291(5503):484-6.
Sendai et al., α1,3-Galactosyltransferase-Gene Knockout in Cattle Using a Single Targeting Vector with loxP Sequences and Cre-Expressing Adenovirus. Transplantation. Mar. 16, 2006;81(5):760-6.
Shen et al., Tissue-Specific Regulation of Human α1-Antitrypsin Gene Expression in Transgenic Mice. DNA. 1989;8(2):101-108.
Shimada et al., Correction of ornithine transcarbamylase (OTC) deficiency in spf-ash mice by introduction of rat OTC gene. FEBS letters. Feb. 1991;279(1):198-200.
Smith, Commercial exploitation of transgenics. Biotechnol Adv. 1994;12(4):679-86.
Suen et al., Transient expression of an IL-23R extracellular domain Fc fusion protein in CHO vs. HEK cells results in improved plasma exposure. Protein Expr Purif. May 2010;71(1):96-102. doi: 10.1016/j.pep.2009.12.015. Epub Jan. 4, 2010.
Tan, Liver-Specific and Position-Effect Expression of a Retinol-Binding Protein-lacZ Fusion Gene (RBP-lacZ) in Transgenic Mice. Developmental Biology. 1991;146:24-37.
Thomann et al., Fc-galactosylation modulates antibody-dependent cellular cytotoxicity of therapeutic antibodies. Molecular Immunology. 2016;73:69-75.
Todorovska et al., Design and application of diabodies, triabodies and tetrabodies for cancer targeting. J Immunol Methods. Feb. 1, 2001;248(1-2):47-66.
Toyama et al., Quantitative structural characterization of local N-glycan microheterogeneity in therapeutic antibodies by energy-resolved oxonium ion monitoring. Analytical Chem. Nov. 20, 2012;84(22):9655-62.
Varchetta et al., Elements related to heterogeneity of antibody-dependent cell cytotoxicity in patients under trastuzumab therapy for primary operable breast cancer overexpressing Her2. Cancer Research. Dec. 15, 2007;67(24):1191-9.
Wall et al., High-level synthesis of a heterologous milk protein in the mammary glands of transgenic swine. Proc Natl Acad Sci U S A. Mar. 1, 1991;88(5):1696-700.
Ward et al., The commercial and agricultural applications of animal transgenesis. Mol Biotechnol. Oct. 1995;4(2):167-78. Review.
Watson et al., Molecular Biology of the Gene. 4th edition. Chapter 19: Recombinant DNA at Work. The Benjamin/Cummings Publishing Company, Inc. Menlo Park, California. 1987:595-618.
Wells et al., Production of Cloned Calves Following Nuclear Transfer with Cultured Adult Mural Granulosa Cells. Biology of Reproduction. 1999;60:996-1005.
Werner et al., Glycosylation of therapeutic proteins in different production systems. Acta Paediatr. Apr. 2007;96(455):17-22.
Wilkins et al., Isolation of Recombinant Proteins From Milk. Journal of Cellular Biochemistry. 1992;49:333-338.
Wilmut et al., Strategies for production of pharmaceutical proteins in milk. Reprod Fertil Dev. 1994;6(5):625-30. Review.
Wold, In vivo chemical modification of proteins (post-translational modification). Ann Rev Biochem. 1981;50:783-814.
Wolfgang et al., Efficient Method for Expressing Transgenes in Nonhuman Primate Embryos Using a Stable Episomal Vector. Molecular Reproduction and Development. 2002;62:69-73.
Wright et al., High Level Expression of Active Human Alpha-1-Antitrypsin in the Milk of Transgenic Sheep. Biotechnology. 1991;9:830-834.
Yong et al., Nuclear-Cytoplasmic Interaction and Development of Goat Embryos Reconstructed by Nuclear Transplantation: Production of Goats by Serially Cloning Embryos. Biology of Reproduction. 1998;58:266-269.
Yu et al., Functional Human CD4 Protein Produced in Milk of Transgenic Mice. Mol Biol Med. 1989;6:255-261.
Zbikowska et al., The use of uromodulin promoter to target production of recombinant proteins into urine of transgenic animals. Transgenic Research. 2002;11:425-435.
Zbikowska et al., Uromodulin promoter directs high-level expression of biologically active human α1-antitrypsin into mouse urine. Biochem J. 2002;365:7-11.
Zhang et al., Functional Recombinant Human Anti-HBV Antibody Expressed in Milk of Transgenic Mice. Transgenic Res. 2012;21:1085-91.
Zhou et al., Development of a simple and rapid method for producing non-fucosylated oligomannose containing antibodies with increased effector function. Biotechnol Bioeng. Feb. 15, 2008;99(3):652-65.
Ziomek, Commercialization of Proteins Produced in the Mammary Gland. Theriogenology. 1998;49:139-44.

\* cited by examiner

FIG. 5-1 adalimumab produced in goat #1

| RT | day 7 | | | day 17 | | | day 32 | | | Theor | Notes | Structure |
|---|---|---|---|---|---|---|---|---|---|---|---|---|
| | Peak | Mass | % | Peak | Mass | % | Peak | Mass | % | | | |
| 7.4 | 1 | 1233.3 | 2.8 | 1 | 1233.3 | 0.8 | 1 | 1233.5 | 0.5 | 1233.5 | | |
| 8.3 | 2 | 1379.4 | 2.2 | 2 | 1379.4 | 2.3 | 2 | 1379.4 | 1.6 | 1379.5 | | |
| 9.3 | 3 | 1395.3 | 2.2 | 3 | 1395.5 | 0.8 | 3 | 1395.5 | 0.5 | 1395.5 | | |
| 10.1 | 4 | 1354.3 | 9.2 | 4 | 1354.3 | 6.4 | 4 | 1354.3 | 4.6 | 1354.5 | | |
| 11 | 5 | | | 5 | 1557.6 | 0.8 | 5 | 1557.5 | trace | 1557.6 | | |
| | | 1744.3 | 2.0 | | 1744.5 | 1.4 | | 1744.5 | 2.6 | 1744.6 | | |
| 11.6 | 6' | 1686.3 | 1.8 | | | | | | | 1686.6 | | |
| 12.3 | 6 | 1760.5 | 6.0 | 6 | 1760.5 | 3.7 | 6 | 1703.4 | 1.5 | 1703.6 | | |
| | | | | | | | | 1760.5 | 1.9 | 1760.6 | | |
| 12.7 | | | | 7' | 1832.5 | 3.0 | | | | 1832.7 | | |
| 13.2 | 7 | 1906.6 | 27.5 | 7 | 1906.2 | 25.9 | 7 | 1906.5 | 26.5 | 1906.7 | | |
| 14.3 | 8 | 1864.5 | 3.7 | 8 | 1864.5 | 1.1 | 8 | 1864.5 | 1.3 | 1864.6 | | |

FIG. 5-2

| | | | | | | | | |
|---|---|---|---|---|---|---|---|---|
| | 1994.5 | 2.2 | 1994.5 | 9.0 | 1994.5 | 10.9 | 1994.7 | |
| | 2051.5 | 1.5 | 2051.6 | 0.5 | 2051.6 | 0.6 | 2051.7 | |
| 15.4 | 2010.5 | 3.9 | 2010.5 | 5.3 | 2010.5 | 5.5 | 2010.7 | 9 |
| | | 3.9 | | 6.5 | | 5.5 | | |
| | 2197.5 | 11.6 | 2197.5 | 9.6 | 2197.5 | 11.0 | 2197.7 | |
| 16.3 | 2026.5 | 5.7 | 2026.5 | 4.5 | 2026.3 | 3.0 | 2026.7 | 10 |
| | 2156.5 | 4.0 | 2156.6 | 7.2 | 2156.6 | 10.0 | 2156.8 | |
| | 2213.5 | 6.5 | 2213.5 | 6.3 | 2213.5 | 7.0 | 2213.8 | |
| 17.3 | 2172.5 | 3.6 | 2172.5 | 4.9 | 2172.5 | 5.3 | 2172.8 | 11 | mono-Gal (%):      30.8   42.9   44.1   av: 39.2
bi-Gal (%):        53.1   46.0   47.0   av: 48.7
mono-Gal + bi-Gal (%)  83.9   88.9   91.1   av: 88.0
Gal* (%)           82.9   88.2   89.8   av: 87.0
Fuc* (%)           63.5   74.9   81.9   av: 73.4
Ratio Gal/Fuc      1.30   1.17   1.10   av: 1.18
Sialylation (%)    50.4   59.3   62.7   av: 57.5

* calculated according to formulas in specification

FIG. 9-1 adalimumab produced in goat #2

| RT | Peak | day 3 Mass | % | Peak | day 11 Mass | % | Peak | day 21 Mass | % | Theor | Notes | Structure |
|---|---|---|---|---|---|---|---|---|---|---|---|---|
| 7.4 | 1 | 1233.3 | 0.8 | 1 | 1233.8 | 0.7 | 1 | 1233.4 | 0.9 | 1233.5 | | |
| 8.3 | 2 | 1379.8 | 0.6 | 2 | 1379.2 | 0.5 | 2 | 1379.2 | 0.6 | 1379.5 | | |
| 9.2 | 3 | 1395.4 | 0.8 | 3 | 1395.4 | 0.6 | 3 | 1395.7 | 0.7 | 1395.5 | | |
| 10.2 | 4 | 1354.4 | 13.0 | 4 | 1354.3 | 14.2 | 4 | 1354.4 | 14.1 | 1354.5 | | |
| 11.2 | 5 | 1557.5 | 1.4 | 5 | 1557.4 | 0.8 | 5 | 1557.4 | 1.1 | 1557.6 | | |
|  |  | 1744.5 | 3.3 |  | 1744.6 | 1.5 |  | 1744.5 | 2.1 | 1744.6 | | |
| 11.7 |  |  |  | 6' | 1516.5 | 6.9 |  |  |  | 1516.5 | isomers | |
| 12.2 | 6 | 1516.4 | 7.0 | 6 | 1516.4 | 2.9 | 6 | 1516.5 | 7.6 | 1516.5 | | |
|  |  | 1760.5 | 3.0 |  | 1760.5 | 3.6 |  | 1760.5 | 1.9 | 1760.6 | | |
| 13.2 | 7 | 1906.5 | 21.0 | 7 | 1906.5 | 17.6 | 7 | 1906.6 | 15.6 | 1906.7 | | |
| 13.8 | 8 | 1678.3 | 1.8 | 8 | 1678.5 | 0.9 | 8 | 1678.5 | 3.5 | 1678.8 | 2x | |
|  |  | 1848.6 | 1.2 |  | 1848.5 | 1.8 |  | 1848.6 | 1.2 | 1848.7 | | |
| 14.3 | 9 | 1678.5 | 2.8 | 9 | 1678.5 | 1.8 | 9 | 1678.4 | 3.6 | 1678.8 | isomers 2x | |
|  |  | 1864.5 | 1.6 |  | 1864.5 | 1.4 |  | 1864.5 | 1.1 | 1864.6 | | |
|  |  | 1994.6 | 2.8 |  | 1994.6 | 2.5 |  | 1994.6 | 1.8 | 1994.7 | | |
|  |  | 2051.7 | 0.8 |  | 2051.7 | 1.5 |  | 2051.4 | 0.7 | 2051.7 | | |

FIG. 13-1

Adalimumab relative % glycan forms

| Goat | Goat #3 | Goat #4 | Goat #5 | Goat #6 | Goat #7 |
|---|---|---|---|---|---|
| Expression | 5 g/L | 4 g/L | 4 g/L | 4 g/L | 5 g/L |
| Lactation | NL1 d29 | NL1 d29 | NL1 d29 | NL1 d29 | NL1 d29 |
| total asialo | 81 | 97 | 93 | 94 | 95 |
| total sialylated | 19 | 3 | 7 | 6 | 5 |
| high mann | 43 | 60 | 56 | 46 | 49 |
| hybrid | 30 | 23 | 25 | 30 | 28 |
| complex | 28 | 17 | 19 | 24 | 23 |
| sial'd hybrid | 16 | 2 | 5 | 6 | 5 |
| sial'd complex | 4 | 1 | 2 | 0 | 0 |
| sialyation substrates | 37 | 32 | 33 | 41 | 38 |

| Goat #1 | Goat #8 | Goat #9 | Goat #2 |
|---|---|---|---|
| 29 g/L | 14 g/L | 35 g/L | 34 g/L |
| NL1 d32 | NL1 d29 | NL1 d29 | NL1 d29 |
| 40 | 80 | 50 | 96 |
| 60 | 20 | 50 | 4 |
| 5 | 15 | 16 | 80 |
| 46 | 16 | 37 | 7 |
| 50 | 68 | 47 | 13 |
| 42 | 10 | 36 | 3 |
| 19 | 10 | 15 | 1 |
| 50 | 73 | 44 | 16 |

Goat #10

| Peak | RT | MS | % | Putative Structure |
|---|---|---|---|---|
| 1 | 9.5 | 790.8 | 2% | |
| 2 | 10.2 | 1354.6 | 12% | |
| 3 | 11.4 | 871.9 | 6% | |
| 4 | 12.0 | 1516.4 | 13% | |
| 5 | 12.8 | 915.8 | 1% | |
| 6 | 13.3 | 952.9 | 11% | |
| 7 | 14.2 | 838.9 | 13% | 2x |

Goat #1

| Peak | RT | MS | % | Putative Structure |
|---|---|---|---|---|
| 1 | 10.2 | 1354.5 | 11% | |
| 2 | 11.4 | 871.9 | 2% | |
| 3 | 12.5 | 1516.5 | 2% | |
|  |  | 879.9 | 3% | |
| 4 | 13.1 | 915.8 | 2% | |
| 5 | 13.5 | 952.9 | 24% | |

FIG. 15-1

| mass | Goat #2 | Goat #4 | Goat #7 | Goat #6 | Goat #3 | Goat #9 | Goat #5 | Goat #8 | Structure |
|---|---|---|---|---|---|---|---|---|---|
| 1432.7 | 0.6% | 0.3% | 0.0% | 0.0% | 0.0% | 0.0% | 0.0% | 0.0% | 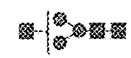 |
| 1595.8 | 16.9% | 17.9% | 6.1% | 5.5% | 12.8% | 11.1% | 8.7% | 6.7% | 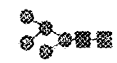 |
| 1799.9 | 25.3% | 26.1% | 21.5% | 22.2% | 14.0% | 2.1% | 20.0% | 4.8% | 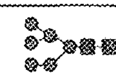 |
| 1840.9 | 1.1% | 0.0% | 1.0% | 0.0% | 1.2% | 1.4% | 1.5% | 0.5% | 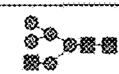 |
| 1852.0 | 0.0% | 5.1% | 7.6% | 7.1% | 3.2% | 0.7% | 5.3% | 0.0% | 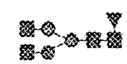 |
| 1882.0 | 1.5% | 1.0% | 1.0% | 1.5% | 1.0% | 0.0% | 2.3% | 1.4% | 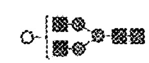 |
| 2004.0 | 18.4% | 8.4% | 9.4% | 10.1% | 8.0% | 0.0% | 12.5% | 2.9% | 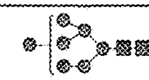 |
| 2056.1 | 2.4% | 19.9% | 22.5% | 24.1% | 12.8% | 0.0% | 18.5% | 5.8% | 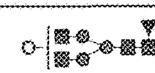 |
| 2086.1 | 3.0% | 0.0% | 1.2% | 3.0% | 1.2% | 0.0% | 0.8% | 5.8% | 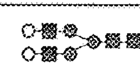 |
| 2208.1 | 15.7% | 6.9% | 10.2% | 7.1% | 7.2% | 3.1% | 12.5% | 1.0% | 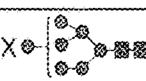 |
| 2232.1 | 0.0% | 0.0% | 0.0% | 0.0% | 0.0% | 2.1% | 0.0% | 1.4% | 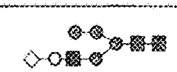 |

FIG. 15-2

| m/z | | | | | | | | | structures |
|---|---|---|---|---|---|---|---|---|---|
| 2260.2 | 7.5% | 10.5% | 13.1% | 12.1% | 18.8% | 29.3% | 9.4% | 50.0% | |
| 2376.2 | 0.5% | 0.5% | 0.6% | 1.5% | 3.6% | 10.5% | 1.1% | 1.4% | |
| 2406.2 | 0.9% | 0.5% | 1.6% | 2.0% | 4.8% | 11.1% | 1.9% | 4.8% | and |
| 2412.2 | 3.3% | 0.8% | 1.6% | 1.4% | 0.6% | 0.0% | 1.9% | 0.0% | |
| 2436.2 | 0.6% | 0.2% | 0.8% | 0.0% | 1.2% | 2.1% | 0.8% | 1.4% | |
| 2580.3 | 0.5% | 0.8% | 0.6% | 1.5% | 3.2% | 8.4% | 0.8% | 1.4% | |
| 2610.3 | 0.5% | 0.3% | 1.0% | 1.3% | 2.8% | 3.5% | 0.8% | 1.4% | |
| 2621.3 | 0.9% | 0.8% | 0.0% | 0.0% | 2.0% | 7.7% | 0.8% | 1.9% | |
| 2651.3 | 0.5% | 0.0% | 0.0% | 0.0% | 1.6% | 7.0% | 0.8% | 7.7% | |
| total | 100% | 100% | 100% | 100% | 100% | 100% | 100% | 100% | | quantification was performed using MALDI-TOF-MS of permethylated glycans (sodium adducted).

HIGHLY GALACTOSYLATED ANTI-TNF-α ANTIBODIES AND USES THEREOF

RELATED APPLICATIONS

This application is a national stage filing under 35 U.S.C. § 371 of International Application No. PCT/IB2014/000692, entitled "Highly Galactosylated Anti-TNF-Alpha Antibodies and Uses Thereof," filed Feb. 13, 2014, which was published under PCT Article 21(2) in English and which claims the benefit under 35 U.S.C. § 119(e) of U.S. Provisional Application Ser. No. 61/764,475, entitled "Highly Galactosylated Anti-TNF-Alpha Antibodies and Uses Thereof," filed on Feb. 13, 2013, the entire contents of each of which is incorporated by reference herein in its entirety.

FIELD OF THE INVENTION

The present invention relates in part to anti-TNF-alpha antibodies.

BACKGROUND OF THE INVENTION

TNF-alpha is a pro-inflammatory cytokine, which plays a protective role against infection and injury in normal immune responses. However, chronically elevated levels of TNF-alpha have been associated with pathogenesis of many autoimmune and inflammatory diseases. A number of TNF-alpha binding therapeutics have been approved for treatment of autoimmune and inflammatory diseases including rheumatoid arthritis, psoriasis, Crohn's disease, ankylating spondylitis and ulcerative colitis. Available therapeutic TNF-alpha binders include antibodies such as infliximab/Remicade (Centocor) a mouse-human chimeric monoclonal anti TNF-antibody, adalimumab/Humira (Abbott) a fully human anti-TNF antibody, and golimumab/Simponi (Centocor) a fully human anti-TNF antibody. Therapeutic TNF-alpha binders that are antibody-based include Etanercept/Enbrel (Amgen) a fusion protein of the extracellular domain of TNF-receptor fused to the Fc region of Ig1, and certolizumab pegol/Cimzia (UCB) a Pegylated Fab' fragment of humanized monoclonal anti-TNF antibody. The therapeutic efficacy of the antibodies and antibody-based TNF-alpha binders varies based on the targeted pathology. In addition, many of the anti-TNF-alpha therapeutics show undesired side effects. Anti-TNF alpha antibodies with improved therapeutic properties are desired therefore.

SUMMARY OF INVENTION

In one aspect, the disclosure relates to highly galactosylated anti-TNF-alpha antibodies and compositions thereof. In one aspect, the disclosure relates to populations of anti-TNF-alpha antibodies with a high level of galactosylation, and compositions thereof. In one aspect, the disclosure relates to methods of production and use of highly galactosylated anti-TNF-alpha antibodies and populations of anti-TNF-alpha antibodies with a high level of galactosylation.

In one aspect the disclosure provides an anti-TNF-alpha antibody, wherein the antibody is highly galactosylated. In some embodiments, the antibody is highly fucosylated. In some embodiments, the antibody comprises mono-galactosylated N-glycans. In some embodiments, the antibody comprises bi-galactosylated N-glycans. In some embodiments, the heavy chain of the antibody comprises SEQ ID NO:1, and the light chain of the antibody comprises SEQ ID NO:2. In some embodiments, the antibody is adalimumab.

In some embodiments, the antibody is produced in mammary epithelial cells of a non-human mammal. In some embodiments, the antibody is produced in a transgenic non-human mammal. In some embodiments, the non-human mammal is a goat, sheep, bison, camel, cow, pig, rabbit, buffalo, horse, rat, mouse or llama. In some embodiments, the non-human mammal is a goat.

In one aspect the disclosure provides compositions of any of the antibodies disclosed herein, wherein the composition further comprises milk. In some embodiments, the composition further comprises a pharmaceutically-acceptable carrier.

In one aspect the disclosure provides a composition, comprising a population of antibodies, wherein the antibody is an anti-TNF-alpha antibody, and wherein the level of galactosylation of the antibodies in the population is at least 60%. In some embodiments, the level of galactosylation of the antibodies in the population is at least 70%. In some embodiments, the level of galactosylation of the antibodies in the population is at least 80%. In some embodiments, the level of fucosylation of the antibodies in the population is at least 50%.

In some embodiments, the level of fucosylation of the antibodies in the population is at least 60%. In some embodiments of any of the compositions provided herein, the population comprises antibodies that comprise mono-galactosylated N-glycans. In some embodiments of any of the compositions provided herein, the population comprises antibodies that comprise bi-galactosylated N-glycans. In some embodiments of any of the compositions provided herein, the ratio of the level of galactosylation of the antibodies in the population to the level of fucosylation of the antibodies in the population is between 1.0 and 1.4. In some embodiments of any of the compositions provided herein, at least 35% of the antibodies in the population comprise bi-galactosylated N-glycans and at least 25% of the antibodies in the population comprise mono-galactosylated N-glycans. In some embodiments of any of the compositions provided herein, the heavy chain of the antibody comprises SEQ ID NO:1, and the light chain of the antibody comprises SEQ ID NO:2. In some embodiments of any of the compositions provided herein, the antibody is adalimumab. In some embodiments of any of the compositions provided herein, the antibody is produced in mammary epithelial cells of a non-human mammal. In some embodiments of any of the compositions provided herein, the antibody is produced in a transgenic non-human mammal. In some embodiments, the non-human mammal is a goat, sheep, bison, camel, cow, pig, rabbit, buffalo, horse, rat, mouse or llama. In some embodiments, the non-human mammal is a goat. In some embodiments, the composition further comprises milk. In some embodiments, the composition further comprises a pharmaceutically-acceptable carrier.

In some embodiments of any of the compositions provided herein, the population of antibodies has an increased level of complement dependent cytotoxicity (CDC) activity when compared to a population of antibodies not produced in mammary gland epithelial cells.

In some embodiments of any of the compositions provided herein, the population of antibodies has an increased level of antibody-dependent cellular cytotoxicity (ADCC) activity when compared to a population of antibodies not produced in mammary gland epithelial cells.

In some embodiments of any of the compositions provided herein, the population of antibodies has an increased ability to suppress TNF-alpha activity in a subject when compared to a population of antibodies not produced in mammary gland epithelial cells.

In some embodiments of any of the compositions provided herein, the population of antibodies has an increased ability to bind soluble TNF-alpha when compared to a population of antibodies not produced in mammary gland epithelial cells.

In some embodiments of any of the compositions provided herein, the population of antibodies has an increased ability to bind transmembrane TNF-alpha when compared to a population of antibodies not produced in mammary gland epithelial cells.

In some embodiments of any of the compositions provided herein, the population of antibodies not produced in mammary gland epithelial cells is produced in cell culture.

In some embodiments of any of the compositions provided herein, the level of galactosylation of the antibodies not produced in mammary gland epithelial cells is 50% or lower when compared to the level of galactosylation of the antibodies produced in mammary gland epithelial cells. In some embodiments of any of the compositions provided herein, the level of galactosylation of the antibodies not produced in mammary gland epithelial cells is 30% or lower when compared to the level of galactosylation of the antibodies produced in mammary gland epithelial cells. In some embodiments of any of the compositions provided herein, the level of galactosylation of the antibodies not produced in mammary gland epithelial cells is 10% or lower when compared to the level of galactosylation of the antibodies produced in mammary gland epithelial cells.

In one aspect, the disclosure provides a method for producing a population of antibodies, comprising: expressing the population of antibodies in mammary gland epithelial cells of a non-human mammal such that a population of antibodies is produced, wherein the antibody is an anti-TNF-alpha antibody, wherein the level of galactosylation of the antibodies in the population is at least 60%. In some embodiments, the mammary gland epithelial cells are in culture and are transfected with a nucleic acid that comprises a sequence that encodes the antibody. In some embodiments, the mammary gland epithelial cells are in a non-human mammal engineered to express a nucleic acid that comprises a sequence that encodes the antibody in its mammary gland. In some embodiments, the nucleic acid comprises SEQ ID NO:3 and SEQ ID NO:4. In some embodiments, the mammary gland epithelial cells are goat, sheep, bison, camel, cow, pig, rabbit, buffalo, horse, rat, mouse or llama mammary gland epithelial cells. In some embodiments, the mammary gland epithelial cells are goat mammary gland epithelial cells.

In one aspect, the disclosure provides mammary gland epithelial cells that produce any of the antibodies, population of antibodies, or compositions disclosed herein.

In one aspect, the disclosure provides a transgenic non-human mammal comprising any of the mammary gland epithelial cells disclosed herein.

In one aspect, the disclosure provides a method comprising administering any of the antibodies, population of antibodies, or compositions disclosed herein to a subject in need thereof. In some embodiments, the subject has an inflammatory disorder or autoimmune disorder. In some embodiments, the inflammatory disorder or autoimmune disorder is rheumatoid arthritis, psoriasis, Crohn's disease, juvenile idiopathic arthritis, ankylozing spondylitis, ulcerative colitis, chronic inflammation, hepatitis, Behcet's disease, Wegener's granulomatosis, or sarcoidosis.

In one aspect, the disclosure provides a monoclonal anti-TNF antibody composition comprising monoclonal anti-TNF antibodies having glycan structures on the Fc glycosylation sites (Asn297, EU numbering), wherein said glycan structures have a galactose content of more than 60%.

In one aspect, the disclosure relates to an anti-TNF-alpha antibody, wherein the antibody contains an oligomannose. In some embodiments, the heavy chain of the antibody comprises SEQ ID NO:1, and the light chain of the antibody comprises SEQ ID NO:2. In some embodiments, the antibody is adalimumab.

In some embodiments, the antibody is produced in mammary epithelial cells of a non-human mammal. In some embodiments, the antibody is produced in a transgenic non-human mammal. In certain embodiments, the non-human mammal is a goat, sheep, bison, camel, cow, pig, rabbit, buffalo, horse, rat, mouse or llama. In certain embodiments, the non-human mammal is a goat.

In some embodiments, an anti-TNF-alpha antibody that contains an oligomannose further comprising milk.

In one aspect, the disclosure relates to a composition comprising an anti-TNF-alpha antibody that contains an oligomannose, further comprising a pharmaceutically-acceptable carrier.

In one aspect, the disclosure relates to a composition, comprising: a population of antibodies, wherein the antibody is an anti-TNF-alpha antibody, and wherein the at least 30% of the antibodies contain at least one oligomannose. In some embodiments, the antibodies exhibit a high mannose glycosylation pattern. In some embodiments, at least one chain of the milk-derived antibodies contains an oligomannose and is non-fucosylated. In some embodiments, the major carbohydrate of the milk-derived antibodies is non-fucosylated.

In some embodiments, the heavy chain of the antibody within the composition comprises SEQ ID NO:1, and the light chain of the antibody comprises SEQ ID NO:2. In some embodiments, the antibody is adalimumab. In some embodiments, the antibody is produced in mammary epithelial cells of a non-human mammal. In some embodiments, the antibody is produced in a transgenic non-human mammal. In some embodiments, the non-human mammal is a goat, sheep, bison, camel, cow, pig, rabbit, buffalo, horse, rat, mouse or llama. In certain embodiments, the non-human mammal is a goat.

In some embodiments, the composition further comprises milk. In some embodiments, the composition further comprises a pharmaceutically-acceptable carrier.

In some embodiments, the population of antibodies within the composition has an increased level of complement dependent cytotoxicity (CDC) activity when compared to a population of antibodies not produced in mammary gland epithelial cells.

In some embodiments, the population of antibodies within the composition has an increased level of antibody-dependent cellular cytotoxicity (ADCC) activity when compared to a population of antibodies not produced in mammary gland epithelial cells. In some embodiments, the population of antibodies not produced in mammary gland epithelial cells is produced in cell culture.

In some embodiments wherein an antibody contains an oligomannose, the oligomannose is Man5. In some embodiments wherein an antibody contains an oligomannose, the oligomannose is Man6. In some embodiments wherein an antibody contains an oligomannose, the oligomannose is Man7. In some embodiments wherein a composition comprises an antibody that contains an oligomannose, the oligomannose is Man5. In some embodiments wherein a composition comprises an antibody that contains an oligomannose, the oligomannose is Man6. In some embodiments wherein a composition comprises an antibody that contains an oligomannose, the oligomannose is Man7.

BRIEF DESCRIPTION OF THE DRAWINGS

The drawings are first described. It is to be understood that the drawings are exemplary and not required for enablement of the invention.

FIG. 5 shows a summary of the percentages of N-glycan oligosaccharides of populations of a highly galactosylated adalimumab antibodies from goat #1 at various days of lactation.

FIG. 15 shows a summary of N-glycan oligosaccharides of populations of transgenically produced adalimumab antibodies from eight different goats, goats #2-9.

DETAILED DESCRIPTION OF INVENTION

Figure 1:
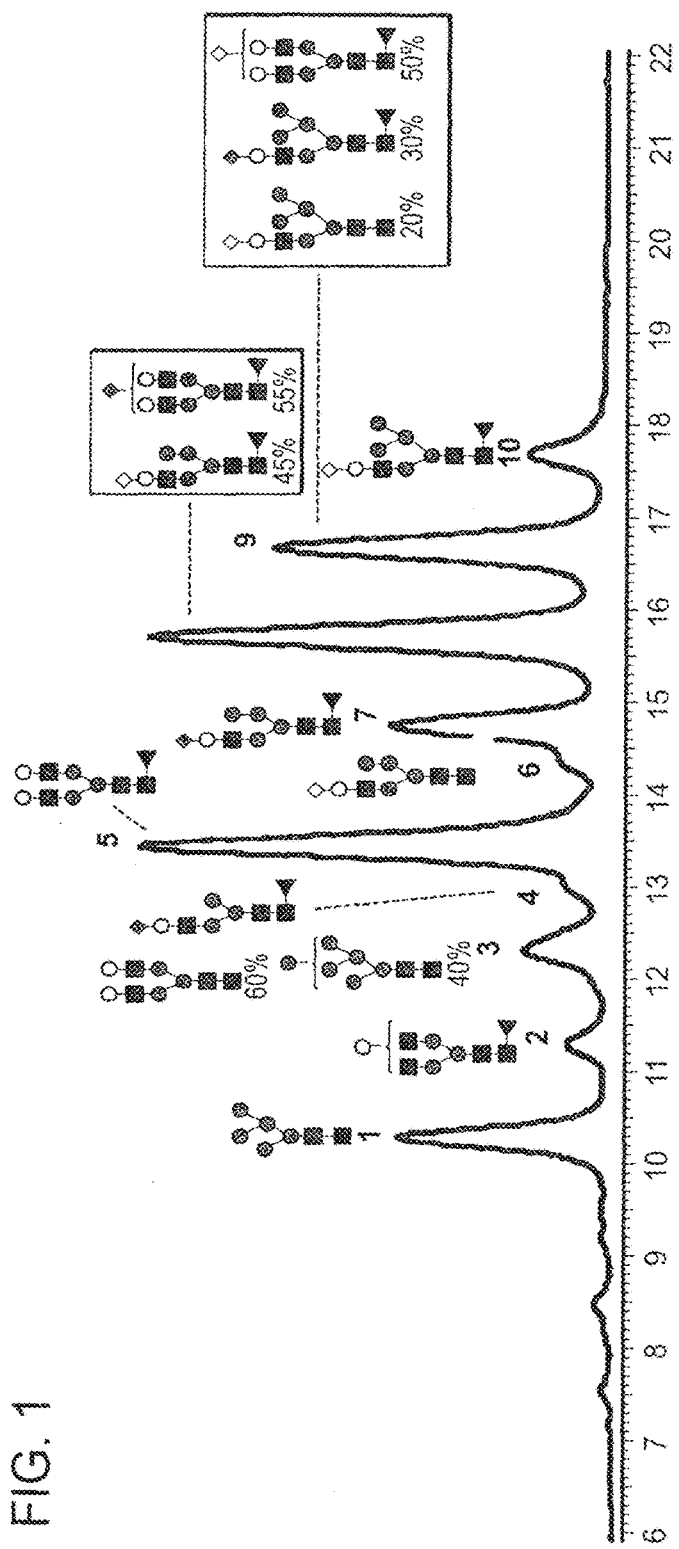
FIG. 1 shows a representative oligosaccharide signature of N-glycans of a population of highly galactosylated adalimumab antibodies from goat #1.

In one aspect, the disclosure provides anti-TNF-alpha antibodies wherein the antibody is highly galactosylated. Anti-TNF-alpha antibodies bind TNF-alpha and have been used as a therapeutic in a variety of diseases characterized by dysregulation of TNF-alpha, including inflammatory disorders. In some embodiments, the anti-TNF-alpha antibody that is highly galactosylated is infliximab/Remicade (Centocor), adalimumab/Humira (Abbott), or golimumab/Simponi (Centocor). In some embodiments, the anti-TNF-alpha antibody that is highly galactosylated is adalimumab.

In some embodiments, the anti-TNF-alpha antibody that is highly galactosylated includes a heavy chain which comprises SEQ ID NO:1. In some embodiments, the anti-TNF-alpha antibody that is highly galactosylated includes a light chain which comprises SEQ ID NO:2. In some embodiments, the anti-TNF-alpha antibody that is highly galactosylated includes a heavy chain which comprises SEQ ID NO:1 and a light chain which comprises SEQ ID NO:2. In some embodiments, the anti-TNF-alpha antibody that is highly galactosylated includes a heavy chain which consists of SEQ ID NO:1. In some embodiments, the anti-TNF-alpha antibody that is highly galactosylated includes a light chain that consists of SEQ ID NO:2. In some embodiments, the anti-TNF-alpha antibody that is highly galactosylated includes a heavy chain which consists of SEQ ID NO:1 and a light chain that consists of SEQ ID NO:2. In some embodiments, the anti-TNF-alpha antibody that is highly galactosylated is adalimumab.

The heavy chain of adalimumab is provided in SEQ ID NO:1:

MEFGLSWLFLVAILKGVQCEVQLVESGGGLVQPGRSLRLSCAASGFTFDD

YAMHWVRQAPGKGLEWVSAITWNSGHIDYADSVEGRFTISRDNAKNSLYL

QMNSLRAEDTAVYYCAKVSYLSTASSLDYWGQGTLVTVSSASTKGPSVFP

LAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCP

PCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDI

AVEWESNGQPENNYKTTPPVLDSDGSFFLYSKLTVDKSRWQQGNVFSCSV

MHEALHNHYTQKSLSLSPGK

The light chain of adalimumab is provided in SEQ ID NO:2:

MDMRVPAQLLGLLLLWLRGARCDIQMTQSPSSLSASVGDRVTITCRASQ

GIRNYLAWYQQKPGKAPKLLIYAASTLQSGVPSRFSGSGSGTDFTLTIS

SLQPEDVATYYCQRYNRAPYTFGQGTKVEIKRTVAAPSVFIFPPSDEQL

KSGTASVVCLLNNFYPREAKVQWKVDNALQSGNSQESVTEQDSKDSTYS

LSSTLTLSKADYEKHKVYACEVTHQGLSSPVTKSFNRGEC

The sequences are based on the sequences of adalimumab published in U.S. Pat. No. 6,090,382. In some embodiments, the sequences of adalimumab are those as published in U.S. Pat. No. 6,090,382.

It should further be appreciated that in some embodiments, the disclosure also includes antibodies that are based on the sequence of adalimumab but that include mutations that provide the antibodies with additional beneficial desired properties related to bioavailability, stability etc.

In one aspect, the disclosure provides highly galactosylated anti-TNF-alpha antibodies that can be used in anti-inflammatory treatment. In some embodiments, the anti-TNF-alpha antibody that is highly galactosylated is infliximab/Remicade (Centocor), adalimumab/Humira (Abbott), or golimumab/Simponi (Centocor). In some embodiments, the anti-TNF-alpha antibody is adalimumab. In some embodiments, the anti-TNF-alpha antibodies can be used in the treatment of inflammatory disorders and the treatment of autoimmune diseases. As shown herein, the highly galactosylated anti-TNF-alpha antibodies are surprisingly effective in their anti-inflammatory activity because of their enhanced ADCC and CDC activities (as compared to non-highly galactosylated antibodies). However, it should appreciated that the highly galactosylated antibodies anti-TNF-alpha disclosed herein may include additional modifications to further increase their anti-inflammatory activity.

Anti-inflammatory activity of intravenous administered Ig can result from a subset of the IgG molecules that have terminal alpha-2,6-sialic acid linkages on their Fc-linked glycans. The anti-inflammatory activity of a population of the intravenous administered Ig was increased by introducing a terminal alpha-2,6-sialic acid linkage on all Fc-linked glycans (See e.g., Anthony et al., Identification of a receptor required for the anti-inflammatory activity of IVIG, PNAS 105: 19571-19578, 2008).

In one aspect, the disclosure provides highly galactosylated anti-TNF-alpha antibodies that also have 2,6 sialylated Fc glycans. The sialylation of the galactosylated anti-TNF alpha antibodies is believed to synergistically increase the anti-inflammatory action of the highly galactosylated anti-TNF-alpha antibodies.

In one aspect, the highly galactosylated anti-TNF-alpha antibodies disclosed herein are generated by producing the antibody in a transgenic mammal or mammary epithelial cells. As shown herein, highly galactosylated anti-TNF-alpha antibodies generated by in a transgenic mammal or mammary epithelial cells are not fully sialylated. The sialylation levels of such antibodies can be increased for instance by subjecting the antibodies to sialyl transferases. The antibodies can be subjected to sialyl transferases in vitro or in vivo. Highly galactosylated anti-TNF-alpha antibodies can be sialylated in vitro by subjecting the purified or partially antibody to a sialyl transferase and the appropriate saccharide based substrate. Highly galactosylated anti-TNF-alpha antibodies can be sialylated in vivo by producing a sialyl transferase in the mammary gland or mammary epithelial cells.

In one aspect, the disclosure provides methods for the production in the mammary gland of transgenic animals and mammary epithelial cells of highly galactosylated anti-TNF-alpha antibodies, with increased levels of alpha-2,6-sialylation. Thus, the methods provided herein allow for the production in the mammary gland of transgenic animals and mammary epithelial cells of highly galactosylated anti-TNF-alpha antibodies with increased anti-inflammatory properties. It should be appreciated that the methods provided herein to increase the anti-inflammatory properties of highly galactosylated anti-TNF-alpha antibodies can be applied to any anti-TNF-alpha antibody, thereby providing anti-inflammatory highly galactosylated anti-TNF-alpha antibodies with synergistic mode of actions.

In one aspect, the disclosure provides transgenic animals (and mammary epithelial cells) that are transgenic for the production in the mammary gland of anti-TNF-alpha antibodies and that are transgenic for the production of sialyl transferase. The therapeutic antibodies produced by such animals and cells are expected to be highly galactosylated and have increased levels of terminal alpha-2,6-sialic acid linkages on their Fc-linked glycans. In some embodiments, the transgenic animals (and mammary epithelial cells) are transgenic for the production in the mammary gland of an exogenous anti-TNF-alpha antibody and are transgenic for the production of sialyl transferase. In some embodiments, the anti-TNF-alpha antibody is adalimumab.

In one aspect, the disclosure provides methods of treating inflammation or autoimmune disease in a subject comprising administering to a subject the highly galactosylated anti-TNF-alpha antibodies that have increased levels of terminal alpha-2,6-sialic acid linkages on their Fc-linked glycans.

In one aspect, the disclosure provides anti-TNF-alpha antibodies wherein the antibody is highly galactosylated. In some embodiments, the disclosure provides anti-TNF-alpha antibodies, wherein the antibody is highly fucosylated. In some embodiments, the disclosure provides anti-TNF-alpha antibodies, wherein the antibody is highly galactosylated and highly fucosylated. In some embodiments, the disclosure provides anti-TNF-alpha antibodies, wherein the antibody is highly galactosylated and highly fucosylated and has terminal sialic acid moieties on the Fc glycans. In some embodiments, the highly galactosylated antibody comprises one or more mono-galactosylated N-glycans. In some embodiments, the highly galactosylated antibody comprises bi-galactosylated N-glycans.

In one aspect, the disclosure provides a monoclonal anti-TNF antibody composition comprising monoclonal antibodies having on the Fc glycosylation sites (Asn 297, EU numbering) glycan structures, wherein said glycan structures have a galactose content more than 60%. In one embodiment the anti-TNF monoclonal antibodies are purified. The "EU numbering system" or "EU index" is generally used when referring to a residue in an immunoglobulin heavy chain constant region (e.g., the EU index reported in Kabat et al., Sequences of Proteins of Immunological Interest, 5th ed., Public Health Service, National Institutes of Health, Bethesda, Md. (1991) expressly incorporated herein by reference). The typical glycosylated residue position in an antibody is the asparagine at position 297 according to the EU numbering system ("Asn297").

It should be appreciated that any of the anti-TNF monoclonal antibodies disclosed herein may be partially or completely purified.

Antibodies can be glycosylated with an N-glycan at the Fc-gamma glycosylation site in the heavy chain (Asn297) of the Fc region. Generally, antibodies include two heavy chains and each antibody therefore can have two Fc-gamma N-glycans. A variety of glycosylation patterns have been observed at the Fc gamma glycosylation site and the oligosaccharides found at this site include galactose, N-acetylglucosamine (GlcNac), mannose, sialic acid, N-acetylneuraminic acid (NeuAc or NANA), N-glycolylneuraminic (NGNA) and fucose. N-glycans found at the Fc gamma glycosylation site generally have a common core structure consisting of an unbranched chain of a first N-acetylglucosamine (GlcNAc), which is attached to the asparagine of the antibody, a second GlcNAc that is attached to the first GlcNac and a first mannose that is attached to the second GlcNac. Two additional mannoses are attached to the first mannose of the GlcNAc-GlcNAc-mannose chain to complete the core structure and providing two "arms" for additional glycosylation. In addition, fucose residues may be attached to the N-linked first GlcNAc.

The two arm core structure is also referred to as the "antenna". The most common type of glycosylation of the "arms" of the N-glycan motifs found in plasma antibodies is of the complex type, i.e., consisting of more than one type of monosaccharide. In the biosynthetic route to this N-glycan motif, several GlcNAc transferases attach GlcNAc residues to the mannoses of the glycan core, which can be further extended by galactose, sialic acid and fucose residues. This glycosylation motif is called "complex" structure.

A second glycosylation motif found on the "arms" of the N-glycan core structure is a "high-mannose" motif, which is characterized by additional mannoses (attached either as branched or unbranded chains).

A third glycosylation motif is a hybrid structures in which one of the arms is mannose substituted while the other arm is complex.

A "galactosylated" antibody, as used herein, refers to any antibody that has at least one galactose monosaccharide in one of its N-glycans. Galactosylated antibodies include antibodies where the two N-glycans each have complex type motifs on each of the arms of the N-glycan motifs, antibodies where the two N-glycans have a complex type motif on only one of the arms of the N-glycan motifs, antibodies that have one N-glycan with complex type motifs on each of the arms of the N-glycan, and antibodies that have one N-glycan with a complex type motif on only one of the arms of the N-glycan motifs. Antibodies that include at least one galactose monosaccharide include antibodies with N-glycans such as G1 (one galactose), G1F (one galactose, one fucose), G2 (two galactoses) and G2F (two galactoses, one fucose). In addition, the N-glycan that includes at least one galactose monosaccharide can be sialylated or not sialylated. It should further be appreciated that the N-glycans may also contain additional galactose residues, such as alpha-Gal, in one or more arms of the complex glycan motif, potentially resulting in an N-glycan with four galactose moieties.

A "highly galactosylated" antibody, as used herein, refers to an antibody that includes at least two galactose monosaccharides in the N-glycan motifs. Highly galactosylated antibodies include antibodies where the two N-glycans each have complex type motifs on each of the arms of the N-glycan motifs, antibodies where the two N-glycans have a complex type motif on only one of the arms of the N-glycan motifs, and antibodies that have one N-glycan with a complex type motif on each of the arms of the N-glycan. Thus, highly galactosylated antibodies include antibodies in which both N-glycans each include one galactose in the glycan motif (e.g., G1 or G1F), antibodies that include at least one N-glycan with two galactoses in the glycan motif (e.g., G2 or G2F), and antibodies with 3 or 4 galactoses in the glycan motif (e.g., (i) one N-glycan with a G1 glycan motif and one N-glycan with a G2 or G2F glycan motif or (ii) two N-glycan with G2 or G2F). In some embodiments, the highly galactosylated antibody includes at least three galactose monosaccharides in the glycan motifs. In some embodiments, the highly galactosylated antibody includes at least four galactose monosaccharides in the glycan motifs.

In some embodiments the glycosylation exhibits a high mannose glycosylation pattern. As used herein, a "high mannose glycosylation pattern" is intended to refer to an antibody that contains at least one oligomannose or a composition of antibodies wherein at least 30% of the antibodies contain at least one oligomannose. In some embodiments at least 30%, 40%, 50%, 60%, 70%, 80%, 90% or more of the carbohydrates of the antibodies are oligomannose. In some embodiments at least 30%, 40%, 50%, 60%, 70%, 80%, 90% or more of the carbohydrates of the antibodies are non-fucosylated oligomannose. In other embodiments less than 50%, 40%, 30%, 20%, 10%, 5% or fewer of the carbohydrates of the antibodies are fucose-containing. In still other embodiments the antibodies are low in fucose and high in oligomannose. Therefore, in further embodiments at least 30%, 40%, 50%, 60%, 70%, 80% or 90% or more of the carbohydrates of the antibodies are oligomannose and less than 50%, 40%, 30%, 20%, 10% or 5% of the carbohydrates of the antibodies are fucose-containing. Therefore, in yet a further embodiment at least 30%, 40%, 50%, 60%, 70%, 80% or 90% or more of the carbohydrates of the antibodies are non-fucosylated oligomannose and less than 50%, 40%, 30%, 20%, 10% or 5% of the carbohydrates of the antibodies are fucose-containing.

In some aspects, the mannose-containing oligosaccharides range from Man5 to Man9, with the number indicating the number of mannose residues. For example, mannose-containing oligosaccharides can include Man5, Man6, Man7, Man8 and Man9. In certain embodiments, transgenically produced adalimumab exhibits a high Man6 content, as revealed by goats 2, 4 and 5 described herein. In some embodiments, the major carbohydrate in transgenically produced adalimumab is Man5. In some embodiments, at least 10%, 15%, or more of the carbohydrates in transgenically produced adalimumab are Man5. Advantageously, at least 20% of the carbohydrates in transgenically produced adalimumab are Man5. In other embodiments, the major carbohydrate in transgenically produced adalimumab is Man6. In some embodiments, at least 10%, 15%, or more of the carbohydrates in transgenically produced adalimumab are Man6. Advantageously, at least 20% of the carbohydrates in transgenically produced adalimumab are Man6 In other embodiments, the major carbohydrate in transgenically produced adalimumab is Man7. In some embodiments, at least 10%, 15%, or more of the carbohydrates in transgenically produced adalimumab are Man7. Advantageously, at least 20% of the carbohydrates in transgenically produced adalimumab are Man7.

The glycosylation pattern of the N-glycans can be determined by a variety of methods known in the art. For example, methods of analyzing carbohydrates on proteins have been described in U.S. Patent Applications US 2006/0057638 and US 2006/0127950. The methods of analyzing carbohydrates on proteins are incorporated herein by reference.

In some embodiments, the highly galactosylated antibody is produced in mammary epithelial cells of a non-human mammal. In some embodiments, the antibody is produced in a transgenic non-human mammal. In some embodiments, the non-human mammal is a goat, sheep, bison, camel, cow, pig, rabbit, buffalo, horse, rat, mouse or llama. In some embodiments, the non-human mammal is a goat.

In some embodiments, the highly glycosylated antibody is produced in cells other than in mammary epithelial cells of a non-human mammal. In some embodiments, the antibody is produced in cells other than in mammary epithelial cells of a non-human mammal and modified after production to increase the number of galactose groups on the N-glycan (e.g., through the action of enzymes such as transferases).

In one aspect, the disclosure provides compositions comprising highly galactosylated antibodies. In some embodiments, the composition comprising highly galactosylated antibodies further comprises milk. In some embodiments, the composition comprising highly galactosylated antibodies further comprises a pharmaceutically-acceptable carrier.

In one aspect, the disclosure provides compositions comprising monoclonal anti-TNF antibody compositions having on the Fc glycosylation sites (Asn 297, EU numbering) glycan structures, wherein said glycan structures of the monoclonal antibodies have a galactose content more than 60%. In some embodiments, the composition comprising monoclonal anti-TNF antibody compositions further comprises milk. In some embodiments, the composition comprising monoclonal anti-TNF antibody compositions further comprises a pharmaceutically-acceptable carrier.

Populations of Antibodies

In one aspect, the disclosure provides a composition comprising a population of antibodies, wherein the antibody is an anti-TNF-alpha antibody, and wherein the level of galactosylation of the antibodies in the population is at least 60%. In some embodiments, the level of galactosylation of the antibodies in the population is at least 70%. In some embodiments, the level of galactosylation of the antibodies in the population is at least 80%. In some embodiments, the level of fucosylation of the antibodies in the population is at least 50%. In some embodiments, the level of fucosylation of the antibodies in the population is at least 60%. In some embodiments, the population comprises antibodies that comprise mono-galactosylated N-glycans. In some embodiments, the population comprises antibodies that comprise bi-galactosylated N-glycans. In some embodiments, the ratio of the level of galactosylation of the antibodies in the population to the level of fucosylation of the antibodies in the population is between 1.0 and 1.4. In some embodiments, at least 35% of the antibodies in the population comprise bi-galactosylated N-glycans and at least 25% of the antibodies in the population comprise mono-galactosylated N-glycans. In some embodiments, the level of sialylation in the antibodies is at least 50%. In some embodiments, the level of sialylation in the antibodies is at least 70%. In some embodiments, the level of sialylation in the antibodies is at least 90%. In some embodiments, the antibodies are fully sialylated.

In some embodiments, the anti-TNF-alpha antibody of the populations of antibodies with a high level of galactosylation is infliximab/Remicade (Centocor), adalimumab/Humira (Abbott), or golimumab/Simponi (Centocor). In some embodiments, the anti-TNF-alpha antibody of the populations of antibodies with a high level of galactosylation is adalimumab. In some embodiments, the anti-TNF-alpha antibody of the populations of antibodies with a high level of galactosylation comprises a heavy chain which comprises SEQ ID NO:1. In some embodiments, the anti-TNF-alpha antibody of the populations of antibodies with a high level of galactosylation comprises a light chain which comprises SEQ ID NO:2. In some embodiments, the anti-TNF-alpha antibody of the populations of antibodies with a high level of galactosylation comprises a heavy chain which comprises SEQ ID NO:1 and a light chain which comprises SEQ ID NO:2. In some embodiments, the anti-TNF-alpha antibody of the populations of antibodies with a high level of galactosylation comprises a heavy chain which consists of SEQ ID NO:1. In some embodiments, the anti-TNF-alpha antibody of the populations of antibodies with a high level of galactosylation comprises a light chain that consists of SEQ ID NO:2. In some embodiments, the anti-TNF-alpha antibody of the populations of antibodies with a high level of galactosylation comprises a heavy chain which consists of SEQ ID NO:1 and a light chain that consists of SEQ ID NO:2. In some embodiments, the anti-TNF-alpha antibody of the populations of antibodies with a high level of galactosylation is adalimumab.

The biosynthesis of N-glycans is not regulated by a template, as is the case with proteins, but is mainly dependent on the expression and activity of specific glycosyltransferases in a cell. Therefore, a glycoprotein, such as an antibody Fc domain, normally exists as a heterogeneous population of glycoforms which carry different glycans on the same protein backbone.

A population of anti-TNF-alpha antibodies that is highly galactosylated is a population of antibodies wherein the level of galactosylation of the antibodies in the population is at least 50%, at least 60%, at least 70%, at least 80%, at least 90%, up to 100% of galactosylation. In some embodiments of the population of antibodies that is highly galactosylated, the level of galactosylation of the antibodies in the population is at least 60%.

The level of galactosylation as used herein is determined by the following formula:

$$\sum_{i=1}^{n} \left( \frac{\text{(number of Gal)}}{\text{(number of A)}} * (\% \text{ relative Area}) \right)$$

wherein:
n represents the number of analyzed N-glycan peaks of a chromatogram, such as a Normal-Phase High Performance Liquid Chromatography (NP HPLC) spectrum "number of Gal" represents the number of Galactose motifs on the antennae of the glycan corresponding to the peak, and "number of A" corresponds to the number of N-acetylglucosamine motifs on the antennae of the glycan form corresponding to the peak (excluding the two N-acetylglucosamine motifs of the core structure), and "% relative Area" corresponds to % of the Area under the corresponding peak The level of galactosylation of antibodies in a population of antibodies can be determined, for instance, by releasing the N-glycans from the antibodies, resolving the N-glycans on a chromatogram, identifying the oligosaccharide motif of the N-glycan that corresponds to a specific peak, determining the peak intensity and applying the data to the formula provided above.

Anti-TNF-alpha antibodies that are galactosylated include antibodies that are mono-galactosylated N-glycans and bi-galactosylated N-glycans.

In some embodiments of the population of antibodies that are highly galactosylated, the population comprises antibodies that comprise mono-galactosylated N-glycans, which may or may not be sialylated. In some embodiments of the population of antibodies that is highly galactosylated, at least 1%, at least 5%, at least 10%, at least 15%, at least 20%, at least 25%, at least 30%, at least 40%, at least 50%, at least 60%, at least 70%, at least 80%, at least 90%, up to 100% of the antibody N-glycans comprise mono-galactosylated N-glycans. In some embodiments of the population of antibodies that is highly galactosylated, at least 25% of the antibodies comprise mono-galactosylated N-glycans.

In some embodiments of the population of antibodies that are highly galactosylated, the population comprises antibodies that comprise bi-galactosylated N-glycans, which may or may not be sialylated. In some embodiments of the population of antibodies that is highly galactosylated, at least 1%, at least 5%, at least 10%, at least 15%, at least 20%, at least 25%, at least 30%, at least 40%, at least 50%, at least 60%, at least 70%, at least 80%, at least 90%, up to 100% of the antibody N-glycans comprise bi-galactosylated N-glycans. In some embodiments of the population of antibodies that is highly galactosylated, at least 35% of the antibodies comprise bi-galactosylated N-glycans.

In some embodiments of the population of antibodies that is highly galactosylated, the population comprises antibodies that comprise mono-galactosylated N-glycans, which may or may not be sialylated, and antibodies that comprise bi-galactosylated N-glycans, which may or may not be sialylated. In some embodiments of the population of antibodies that is highly galactosylated, at least 1%, at least 5%, at least 10%, at least 15%, at least 20%, at least 25%, at least 30%, at least 40%, at least 50%, at least 60%, at least 70%, at least 80%, at least 90%, up to 99% of the antibody N-glycans comprise mono-galactosylated N-glycans, and at least 1%, at least 5%, at least 10%, at least 15%, at least 20%, at least 25%, at least 30%, at least 40%, at least 50%, at least 60%, at least 70%, at least 80%, at least 90%, up to 99% of the antibody N-glycans comprise bi-galactosylated N-glycans. In some embodiments of the population of antibody N-glycans that is highly galactosylated, at least 25% of the antibody N-glycans comprise mono-galactosylated N-glycans and at least 35% of the antibodies comprise bi-galactosylated N-glycans.

In some embodiments of the population of antibodies that is highly galactosylated, the population comprises antibodies that are highly fucosylated. A population of antibodies that is highly fucosylated is a population of antibodies wherein the level of fucosylation of the antibody N-glycans in the population is at least 40%, at least 50%, at least 60%, at least 70%, at least 80%, at least 90%, up to 100% of fucosylation. In some embodiments in the population of antibodies that is highly galactosylated, the level of fucosylation of the antibody N-glycans is at least 50%.

The level of fucosylation as used herein is determined by the following formula:

$$\sum_{i=1}^{n} (\text{number of Fucose}) * (\% \text{ relative Area})$$

wherein:

n represents the number of analyzed N-glycan peaks of a chromatogram, such as a Normal-Phase High Performance Liquid Chromatography (NP HPLC) spectrum, and "number of Fucose" represents the number of Fucose motifs on the glycan corresponding to the peak, and "% relative Area" corresponds to % of the Area under the corresponding peak containing the Fucose motif.

Antibodies that are fucosylated include antibodies that have at least one fucose monosaccharide in one of its N-glycans. Antibodies that are fucosylated include antibodies that have a fucose monosaccharide in each of its N-glycans.

In some embodiments, the population of anti-TNF-alpha antibodies disclosed herein relates to a population wherein the level of galactosylation of the antibody N-glycans in the population is at least 60% and the level of fucosylation of the antibodies in the population is at least 50%. In some embodiments, the population of antibodies disclosed herein relates to a population wherein the level of galactosylation of the antibody N-glycans in the population is at least 50%, and the level of fucosylation of the antibody N-glycans in the population is at least 50%, at least 60%, at least 70%, at least 80%, at least 90%, up to 100%. In some embodiments, the population of antibodies disclosed herein relates to a population wherein the level of galactosylation of the antibody N-glycans in the population is at least 60%, and the level of fucosylation of the antibody N-glycans in the population is at least 50%, at least 60%, at least 70%, at least 80%, at least 90%, up to 100%. In some embodiments, the population of antibodies disclosed herein relates to a population wherein the level of galactosylation of the antibody N-glycans in the population is at least 70%, and the level of fucosylation of the antibody N-glycans in the population is at least 50%, at least 60%, at least 70%, at least 80%, at least 90%, up to 100%. In some embodiments, the population of antibodies disclosed herein relates to a population wherein the level of galactosylation of the antibody N-glycans in the population is at least 80%, and the level of fucosylation of the antibody N-glycans in the population is at least 60%, at least 70%, at least 80%, at least 90%, up to 100%. In some embodiments, the population of antibodies disclosed herein relates to a population wherein the level of galactosylation of the antibody N-glycans in the population is at least 90%, and the level of fucosylation of the antibody N-glycans in the population is at least 60%, at least 70%, at least 80%, at least 90%, up to 100%. In some embodiments, the population of antibodies disclosed herein relates to a population wherein the level of galactosylation of the antibody N-glycans in the population is up to 100% and the level of fucosylation of the antibody N-glycans in the population is at least 60%, at least 70%, at least 80%, at least 90%, up to 100%.

In one aspect, the disclosure relates to a composition comprising a population of anti-TNF-alpha antibodies with a specific ratio of the percentage of antibody N-glycans in the population that are galactosylated at the Fc-gamma-glycosylation site to the percentage of antibody N-glycans in the population that are fucosylated at the Fc-gamma-glycosylation site. In some embodiments, the disclosure relates to a composition comprising a population of antibodies wherein the ratio of the level of galactosylation of the antibody N-glycans in the population to the level of fucosylation of the antibody N-glycans in the population is between 0.5 and 2.5, between 0.6 and 2.0, between 0.7 and 1.8, between 0.8 and 1.6, or between 1.0 and 1.4. In some embodiments, the disclosure relates to a composition comprising a population of antibodies wherein the ratio of the level of galactosylation of the antibody N-glycans in the population to the level of fucosylation of the antibody N-glycans in the population is between 1.0 and 1.4, for example 1.2.

In some embodiments, the antibodies and populations of antibodies disclosed herein are highly sialylated. In some embodiments, sialylation refers to 2,6 alpha sialylation on the terminal galactose residues of the Fc glycans. In some embodiments, in a population of highly sialylated antibodies at least 50% of the terminal galactose moieties are sialylated. In some embodiments, in a population of highly sialylated antibodies at least 50%, at least 60%, at least 70%, at least 80%, at least 90% and up to 100% of the terminal galactose moieties are sialylated. In some embodiments, the disclosure provides populations of antibodies that are at least 60% galactosylated and in which at least 50%, at least 60%, at least 70%, at least 80%, at least 90% and up to 100% of the terminal galactose moieties are sialylated. In some embodiments, the disclosure provides populations of antibodies that are at least 70% galactosylated and in which at least 50%, at least 60%, at least 70%, at least 80%, at least 90% and up to 100% of the terminal galactose moieties are sialylated. In some embodiments, the disclosure provides populations of antibodies that are at least 80% galactosylated and in which at least 50%, at least 60%, at least 70%, at least 80%, at least 90% and up to 100% of the terminal galactose moieties are sialylated. In some embodiments, the disclosure provides populations of antibodies that are at least 90% galactosylated and in which at least 50%, at least 60%, at least 70%, at least 80%, at least 90% and up to 100% of the terminal galactose moieties are sialylated.

In some embodiments, the population of anti-TNF-alpha antibodies with a high level of galactosylation is produced in mammary epithelial cells of a non-human mammal. In some embodiments, the population of anti-TNF-alpha antibodies is produced in a transgenic non-human mammal. In some embodiments, the non-human mammal is a goat, sheep, bison, camel, cow, pig, rabbit, buffalo, horse, rat, mouse or llama. In some embodiments, the non-human mammal is a goat.

In some embodiments, the population of anti-TNF-alpha antibodies with a high level of galactosylation is produced in cells other than mammary epithelial cells of a non-human mammal. In some embodiments, the population of anti-TNF-alpha antibodies is modified after production in cells other than mammary epithelial cells of a non-human mammal to increase the number of galactose groups in the population of antibodies (e.g., through the action of enzymes such as transferases).

In one aspect, the disclosure provides compositions comprising populations of anti-TNF-alpha antibodies with a high level of galactosylation. In some embodiments, the composition comprising anti-TNF-alpha antibodies with a high level of galactosylation further comprises milk. In some embodiments, the composition comprising anti-TNF-alpha antibodies with a high level of galactosylation further comprises a pharmaceutically-acceptable carrier.

Production of Populations of Antibodies

In one aspect, the disclosure provides compositions comprising populations of anti-TNF-alpha antibodies with high levels of galactosylation (e.g., at least 70%), wherein the population of antibodies is produced in mammary epithelial cells of a non-human mammal, and wherein the population of antibodies has an increased level of galactosylation when compared to the population of antibodies not produced in mammary gland epithelial cells. In some embodiments, the population of antibodies not produced in mammary gland epithelial cells is produced in cell culture. As used herein, antibodies "produced in cell culture" when compared to antibodies produced in mammary epithelial cells, refers to antibodies produced in standard production cell lines (e.g., CHO cells) but excluding mammary epithelial cells. In some embodiments, the level of galactosylation of the antibodies not produced in mammary gland epithelial cells is 90% or lower, 80% or lower, 70% or lower, 60% or lower, 50% or lower, 40% or lower, 30% or lower, 20% or lower, 10% or lower when compared to the level of galactosylation of the antibodies produced in mammary epithelial cells of a non-human mammal. In some embodiments, the level of galactosylation of the antibodies not produced in mammary gland epithelial cells is 50% or lower when compared to the level of galactosylation of the antibodies produced in mammary epithelial cells of a non-human mammal. In some embodiments, the level of galactosylation of the antibodies not produced in mammary gland epithelial cells is 30% or lower when compared to the level of galactosylation of the antibodies produced in mammary epithelial cells of a non-human mammal. In some embodiments, the level of galactosylation of the antibodies not produced in mammary gland epithelial cells is 10% or lower when compared to the level of galactosylation of the antibodies produced in mammary epithelial cells of a non-human mammal.

In one aspect, the disclosure provides compositions comprising populations of anti-TNF-alpha antibodies with high levels of fucosylation (e.g., at least 60%), wherein the population of antibodies is produced in mammary epithelial cells of a non-human mammal, and wherein the population of antibodies has an increased level of fucosylation when compared to the population of antibodies not produced in mammary gland epithelial cells. In some embodiments, the population of antibodies not produced in mammary gland epithelial cells is produced in cell culture. In some embodiments, the level of fucosylation of the antibodies not produced in mammary gland epithelial cells is 90% or lower, 80% or lower, 70% or lower, 60% or lower, 50% or lower, 40% or lower, 30% or lower, 20% or lower, 10% or lower when compared to the level of fucosylation of the antibodies produced in mammary epithelial cells of a non-human mammal. In some embodiments, the level of fucosylation of the antibodies not produced in mammary gland epithelial cells is 50% or lower when compared to the level of fucosylation of the antibodies produced in mammary epithelial cells of a non-human mammal. In some embodiments, the level of fucosylation of the antibodies not produced in mammary gland epithelial cells is 30% or lower when compared to the level of fucosylation of the antibodies produced in mammary epithelial cells of a non-human mammal. In some embodiments, the level of fucosylation of the antibodies not produced in mammary gland epithelial cells is 10% or lower when compared to the level of fucosylation of the antibodies produced in mammary epithelial cells of a non-human mammal.

In one aspect, the disclosure provides compositions comprising populations of anti-TNF-alpha antibodies with high levels of galactosylation and fucosylation, wherein the population of antibodies is produced in mammary epithelial cells of a non-human mammal, and wherein the population of antibodies has an increased level of galactosylation and fucosylation when compared to the population of antibodies not produced in mammary gland epithelial cells.

Antibodies

In some embodiments, the term "antibody" refers to a glycoprotein comprising at least two heavy (H) chains and two light (L) chains. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. In some embodiments, the antigen is TNF-alpha, either in soluble form, in transmembrane form, or both. The constant regions of the antibodies may mediate the binding of the immunoglobulin to host tissues or factors, including various cells of the immune system (e.g., effector cells) and the first component (C1q) of the classical complement system. Formation of a mature functional antibody molecule can be accomplished when two proteins are expressed in stoichiometric quantities and self-assemble with the proper configuration.

The term "antibodies" is also meant to encompass antigen-binding fragments thereof. Methods for making antibodies and antigen-binding fragments are well known in the art (see, e.g., Sambrook et al, "Molecular Cloning: A Laboratory Manual" (2nd Ed.), Cold Spring Harbor Laboratory Press (1989); Lewin, "Genes IV", Oxford University Press, New York, (1990), and Roitt et al., "Immunology" (2nd Ed.), Gower Medical Publishing, London, N.Y. (1989), WO2006/040153, WO2006/122786, and WO2003/002609). As used herein, an "antigen-binding fragment" of an antibody refers to one or more portions of an antibody that retain the ability to specifically bind to an antigen, e.g., TNF-alpha. It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546) which consists of a VH domain; and (vi) an isolated complementarity determining region (CDR). Furthermore, although the two domains of the Fv fragment, V and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional procedures, such as proteolytic fragmentation procedures, as described in J. Goding, Monoclonal Antibodies: Principles and Practice, pp 98-118 (N.Y. Academic Press 1983), which is hereby incorporated by reference as well as by other techniques known to those with skill in the art. The fragments are screened for utility in the same manner as are intact antibodies.

In some embodiments the antibodies are of the isotype IgG, IgA or IgD. In further embodiments, the antibodies are selected from the group consisting of IgG1, IgG2, IgG3, IgG4, IgM, IgA1, IgA2, IgAsec, IgD, IgE or has immunoglobulin constant and/or variable domain of IgG1, IgG2, IgG3, IgG4, IgM, IgA1, IgA2, IgAsec, IgD or IgE. In other embodiments, the antibodies are bispecific or multispecific antibodies. According to an alternative embodiment, the antibodies of the present disclosure can be modified to be in the form of a bispecific antibody, or a multispecific antibody. The term "bispecific antibody" is intended to include any agent, e.g., a protein, peptide, or protein or peptide complex, which has two different binding specificities which bind to, or interact with (a) a cell surface antigen and (b) an Fc receptor on the surface of an effector cell. The term "multispecific antibody" is intended to include any agent, e.g., a protein, peptide, or protein or peptide complex, which has more than two different binding specificities which bind to, or interact with (a) a cell surface antigen, (b) an Fc receptor on the surface of an effector cell, and (c) at least one other component. Accordingly, the disclosure includes, but is not limited to, bispecific, trispecific, tetraspecific, and other multispecific antibodies which are directed to cell surface antigens, and to Fc receptors on effector cells. The term "bispecific antibodies" further includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen-binding sites (see e.g., Holliger, P., et al. (1993) Proc. Natl. Acad. Sci. USA 90:6444-6448; Poijak, R. J., et al. (1994) Structure 2:1121-1123).

The term "antibodies" also encompasses different types of antibodies, e.g., recombinant antibodies, monoclonal antibodies, humanized antibodies or chimeric antibodies, or a mixture of these.

In some embodiments, the antibodies are recombinant antibodies. The term "recombinant antibody", as used herein, is intended to include antibodies that are prepared, expressed, created or isolated by recombinant means, such as antibodies isolated from an animal that is transgenic for another species' immunoglobulin genes, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

In yet other embodiments, the antibodies can be chimeric or humanized antibodies. As used herein, the term "chimeric antibody" refers to an antibody that combines parts of a non-human (e.g., mouse, rat, rabbit) antibody with parts of a human antibody. As used herein, the term "humanized antibody" refers to an antibody that retains only the antigen-binding CDRs from the parent antibody in association with human framework regions (see, Waldmann, 1991, Science 252:1657). Such chimeric or humanized antibodies retaining binding specificity of the murine antibody are expected to have reduced immunogenicity when administered in vivo for diagnostic, prophylactic or therapeutic applications according to the disclosure.

In certain embodiments, the antibodies are human antibodies. The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo). Human antibodies are generated using transgenic mice carrying parts of the human immune system rather than the mouse system. Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals results in the production of fully human antibodies to the antigen of interest. Following immunization of these mice (e.g., XenoMouse (Abgenix), HuMAb mice (Medarex/GenPharm)), monoclonal antibodies are prepared according to standard hybridoma technology. These monoclonal antibodies have human immunoglobulin amino acid sequences and therefore will not provoke human anti-mouse antibody (HAMA) responses when administered to humans. The human antibodies, like any of the antibodies provided herein can be monoclonal antibodies.

In some embodiments, the antibody is a full-length antibody. In some embodiments the full-length antibody comprises a heavy chain and a light chain. In some embodiments, the antibody is an anti-TNF-alpha antibody. In some embodiments, the heavy chain comprises SEQ ID NO: 1 and the light chain comprises SEQ ID NO: 2. In some embodiments, the antibody is adalimumab.

CDC Activity

In one aspect, the compositions comprising populations of anti-TNF-alpha antibodies with high levels of galactosylation (e.g., at least 70%) have high complement dependent cytotoxicity (CDC) activity. In one aspect, the compositions comprising populations of anti-TNF-alpha antibodies with high levels of galactosylation have high antibody-dependent cellular cytotoxicity (ADCC) activity. In some embodiments, the compositions comprising populations of anti-TNF-alpha antibodies with high levels of galactosylation have high complement dependent cytotoxicity (CDC) activity and have high antibody-dependent cellular cytotoxicity (ADCC) activity.

In some embodiments, the population of anti-TNF-alpha antibodies with high levels of galactosylation has an increased level of complement dependent cytotoxicity (CDC) activity when compared to a population of antibodies that have low levels of galactosylation. In some embodiments, the population of antibodies with high levels of galactosylation and the population of antibodies that have low levels of galactosylation are directed to the same antigen epitope. In some embodiments, the population of antibodies that is highly galactosylated and the population of antibodies that have low levels of galactosylation are encoded by the same nucleic acid. In some embodiments, the nucleic acid encodes the antibody adalimumab.

A population of antibodies that has low levels of galactosylation (is "low galactose"), as used herein, refers to a population of antibodies wherein the level of galactosylation of the antibodies in the population is less than 50%, less than 40%, less than 30%, less than 20%, less than 10%, down to 0%.

In some embodiments, the CDC activity of a population of antibodies with high levels of galactosylation is at least 1.1 times higher, at least 1.2 times higher, at least 1.3 times higher, at least 1.4 times higher, at least 1.5 times higher, at least 1.6 times higher, at least 1.7 times higher, at least 1.8 times higher, at least 1.9 times higher, at least 2 times higher, at least 3 times higher, at least 5 times higher, at least 10 times higher, up to at least 100 times higher or more when compared to a population of antibodies that have low levels of galactosylation.

In some embodiments, the population of antibodies that are highly galactosylated are highly fucosylated (have high levels of fucosylation). In some embodiments, the population of antibodies that are highly galactosylated and highly fucosylated has an increased level of complement dependent cytotoxicity (CDC) activity when compared to a population of antibodies that are low galactose and low fucose (have low levels of galactosylation and fucosylation). In some embodiments, the population of antibodies that is highly galactosylated and highly fucosylated and the population of antibodies that is low galactose and low fucose are directed to the same antigen epitope. In some embodiments, the population of antibodies that is highly galactosylated and highly fucosylated and the population of antibodies that is low galactose and low fucose are encoded by the same nucleic acid. In some embodiments, the nucleic acid encodes the antibody adalimumab.

A population of antibodies that are low fucose or that have low levels of fucosylation, as used herein, refers to a population of antibodies wherein the level of fucosylation of the antibodies in the population is less than 50%, less than 40%, less than 30%, less than 20%, less than 10%, down to 0%.

In some embodiments, the CDC activity of a population of antibodies that is highly galactosylated and highly fucosylated is at least 1.1 times higher, at least 1.2 times higher, at least 1.3 times higher, at least 1.4 times higher, at least 1.5 times higher, at least 1.6 times higher, at least 1.7 times higher, at least 1.8 times higher, at least 1.9 times higher, at least 2 times higher, at least 3 times higher, at least 5 times higher, at least 10 times higher, up to at least 100 times higher or more when compared to a population of antibodies that is low galactose and low fucose.

In some embodiments, the population of antibodies that is highly galactosylated and is produced in mammary gland epithelial cells has an increased level of complement dependent cytotoxicity (CDC) activity when compared to a population of antibodies that is not produced in mammary gland epithelial cells. In some embodiments, the population of antibodies not produced in mammary gland epithelial cells is produced in cell culture. In some embodiments, the population of antibodies that is highly galactosylated produced in mammary gland epithelial cells and the population of antibodies that is not produced in mammary gland epithelial cells may be encoded by the same nucleic acid. In some embodiments, the nucleic acid encodes the antibody adalimumab.

In some embodiments, the CDC activity of a population of antibodies that is highly galactosylated and is produced in mammary gland epithelial cells is at least 1.1 times higher, at least 1.2 times higher, at least 1.3 times higher, at least 1.4 times higher, at least 1.5 times higher, at least 1.6 times higher, at least 1.7 times higher, at least 1.8 times higher, at least 1.9 times higher, at least 2 times higher, at least 3 times higher, at least 5 times higher, at least 10 times higher, up to at least 100 times higher or more when compared to a population of antibodies that is not produced in mammary gland epithelial cells.

In one aspect, the compositions of the populations of antibodies disclosed herein have a high (complement dependent cytotoxicity) CDC activity. Antibodies can act as a therapeutic through various mechanisms, one of which is through CDC activity. Some therapeutic antibodies that bind to target cellular receptors can also bind proteins of the complement pathway. Binding of the complement proteins results in a complement cascade (through C1-complex activation) that eventually results in the formation of a "membrane attack complex" causing cell lysis and death of the cell to which the therapeutic antibody is bound (See e.g., Reff M. E. *Blood* 1994, 83: 435).

In some embodiments a population of antibodies that has an increased level of complement dependent cytotoxicity (CDC) activity, is a population of antibodies that induces a larger amount of cell lysis as compared to a population of antibodies that has does not have an increased level of complement dependent cytotoxicity (CDC) activity. Methods for determining the level of CDC are known in the art and are often based on determining the amount of cell lysis. Commercial kits for determining CDC activity can be purchased for instance from Genscript (Piscataway, N.J.).

ADCC Activity In one aspect, the population of anti-TNF-alpha antibodies with high levels of galactosylation (e.g., at least 70%), has an increased level of antibody-dependent cellular cytotoxicity (ADCC) activity when compared to a population of antibodies that have low levels of galactosylation. In some embodiments, the disclosure provides compositions comprising populations of anti-TNF-alpha antibodies with a high level of galactosylation wherein the population of antibodies is produced in mammary epithelial cells of a non-human mammal, and wherein the population of antibodies has an increased level of antibody-dependent cellular cytotoxicity (ADCC) activity when compared to a population of antibodies not produced in mammary gland epithelial cells. In some embodiments, the population of antibodies not produced in mammary gland epithelial cells is produced in cell culture. In some embodiments, the population of anti-TNF-alpha antibodies with high levels of galactosylation (e.g., at least 70%), has an increased level of antibody-dependent cellular cytotoxicity (ADCC) activity when compared to a population of antibodies that is aglycosylated.

In some embodiments, the population of antibodies that are highly galactosylated has an increased level of antibody-dependent cellular cytotoxicity (ADCC) when compared to a population of antibodies that are low galactose. In some embodiments, the ADCC activity of a population of antibodies that is highly galactosylated is at least 1.1 times higher, 1.2 times higher, 1.3 times higher, 1.4 times higher, 1.5 times higher, 1.6 times higher, 1.7 times higher, 1.8 times higher, 1.9 times higher, 2 times higher, 3 times higher, 5 times higher, 10 times higher, 100 times higher or more when compared to a population of antibodies that are low galactose.

In some embodiments, the population of antibodies that are highly galactosylated and is produced in mammary gland epithelial cells has an increased level of antibody-dependent cellular cytotoxicity (ADCC) when compared to a population of antibodies that is not produced in mammary gland epithelial cells. In some embodiments, the ADCC activity of a population of antibodies that is highly galactosylated and produced in mammary gland epithelial cells is at least 1.1 times higher, 1.2 times higher, 1.3 times higher, 1.4 times higher, 1.5 times higher, 1.6 times higher, 1.7 times higher, 1.8 times higher, 1.9 times higher, 2 times higher, 3 times higher, 5 times higher, 10 times higher, 100 times higher or more when compared to a population of antibodies that is not produced in mammary gland epithelial cells.

In some embodiments, the population of antibodies that is highly galactosylated and is produced in mammary gland epithelial cells has an increased level of antibody-dependent cellular cytotoxicity (ADCC) when compared to a population of antibodies that is not produced in mammary gland epithelial cells. In some embodiments, the population of antibodies not produced in mammary gland epithelial cells is produced in cell culture.

In one aspect, the compositions of the populations of antibodies disclosed herein have a high ADCC activity. Antibodies can act as a therapeutic through various mechanisms, one of which is through ADCC activity. Therapeutic antibodies that bind to cellular receptors on a target cell, and that include the Fc glycosylation site can also bind the Fc-receptor resulting in the anchoring of cells expressing the Fc-receptor to the target cell. The affinity of binding of the Fc regions of antibodies generally is dependent on the nature of the glycosylation of the Fc glycosylation site. The Fc receptor is found on a number of immune cells including natural killer cells, macrophages, neutrophils, and mast cells. Binding to the Fc receptor results in the immune cells inducing cytokines (such as IL-2) and phagocytosis to kill the target cell. In some embodiments, a population of antibodies that has an increased level of antibody-dependent cellular cytotoxicity (ADCC) activity is a population of antibodies that shows increased binding to cells expressing CD16 as compared to a population of antibodies that does not have an increased level of antibody-dependent cellular cytotoxicity (ADCC) activity. In some embodiments a population of antibodies that has an increased level of antibody-dependent cellular cytotoxicity (ADCC) activity is a population of antibodies that shows increased induction of IL-2 production (e.g., in natural killer cells) as compared to a population of antibodies that has does not have an increased level of antibody-dependent cellular cytotoxicity (ADCC) activity. Commercial kits for determining ADCC activity can be purchased for instance from Genscript (Piscataway, N.J.) and Promega (Madison, Wis.). In some embodiments, determining ADCC activity is performed by evaluating the ability to bind CD16.

Anti-TNF-alpha Activity

In one aspect, the population of anti-TNF-alpha antibodies with high levels of galactosylation (e.g., at least 70%) has an increased ability to suppress TNF-alpha activity in a subject when compared to a population of antibodies that have low levels of galactosylation. In some embodiments, the disclosure provides compositions comprising populations of anti-TNF-alpha antibodies with high levels of galactosylation, wherein the population of antibodies is produced in mammary epithelial cells of a non-human mammal, and wherein the population of antibodies has an increased ability to suppress TNF-alpha activity in a subject when compared to a population of antibodies not produced in mammary gland epithelial cells.

In one aspect, the disclosure provides compositions comprising populations of anti-TNF-alpha antibodies with high levels of galactosylation, wherein the population of antibodies is produced in mammary epithelial cells of a non-human mammal, and wherein the population of antibodies has an increased ability to bind soluble TNF-alpha when compared to a population of antibodies not produced in mammary gland epithelial cells.

In one aspect, the disclosure provides compositions comprising populations of anti-TNF-alpha antibodies with high levels of galactosylation, wherein the population of antibodies is produced in mammary epithelial cells of a non-human mammal, and wherein the population of antibodies has an increased ability to bind transmembrane TNF-alpha when compared to a population of antibodies not produced in mammary gland epithelial cells.

In some embodiments, the population of antibodies that are highly galactosylated has an increased ability to suppress TNF-alpha activity, bind soluble TNF-alpha and/or bind transmembrane TNF-alpha when compared to a population of antibodies that are low galactose. In some embodiments, the increased ability to suppress TNF-alpha activity, bind soluble TNF-alpha and/or bind transmembrane TNF-alpha of a population of antibodies that is highly galactosylated is at least 1.1 times higher, 1.2 times higher, 1.3 times higher, 1.4 times higher, 1.5 times higher, 1.6 times higher, 1.7 times higher, 1.8 times higher, 1.9 times higher, 2 times higher, 3 times higher, 5 times higher, 10 times higher, 100 times higher or more when compared to a population of antibodies that are low galactose.

In some embodiments, the population of antibodies that are highly galactosylated and is produced in mammary gland epithelial cells has an increased ability to suppress TNF-alpha activity, bind soluble TNF-alpha and/or bind transmembrane TNF-alpha when compared to a population of antibodies that is not produced in mammary gland epithelial cells. In some embodiments, the increased ability to suppress TNF-alpha activity, bind soluble TNF-alpha and/or bind transmembrane TNF-alpha of a population of antibodies that is highly galactosylated and produced in mammary gland epithelial cells is at least 1.1 times higher, 1.2 times higher, 1.3 times higher, 1.4 times higher, 1.5 times higher, 1.6 times higher, 1.7 times higher, 1.8 times higher, 1.9 times higher, 2 times higher, 3 times higher, 5 times higher, 10 times higher, 100 times higher or more when compared to a population of antibodies that is not produced in mammary gland epithelial cells.

In some embodiments, the population of antibodies that is highly galactosylated and is produced in mammary gland epithelial cells has increased ability to suppress TNF-alpha activity, bind soluble TNF-alpha and/or bind transmembrane TNF-alpha when compared to a population of antibodies that is not produced in mammary gland epithelial cells. In some embodiments, the population of antibodies not produced in mammary gland epithelial cells is produced in cell culture.

In some embodiments, the populations of anti-TNF-alpha antibodies produced in mammary gland epithelial cells are superior to non-mammary gland epithelial cells produced antibodies in suppressing TNF-alpha activity in a subject. Determining the level of TNF-alpha activity in a subject can be evaluated for instance, by administering the population of antibodies to a subject suffering from a disease characterized by increased TNF-alpha activity (e.g., rheumatoid arthritis) or an established model for such a disease. (See e.g., Horiuchi et al., Rheumatology et al. 49:1215).

In some embodiments, the populations of anti-TNF-alpha antibodies produced in mammary gland epithelial cells are superior to non-mammary gland epithelial cells produced antibodies in binding soluble TNF-alpha. In some embodiments, the populations of anti-TNF-alpha antibodies produced in mammary gland epithelial cells are superior to non-mammary gland epithelial cells produced antibodies in binding transmembrane TNF-alpha. Assays for determining the level of binding to soluble TNF-alpha or transmembrane TNF-alpha are well-established (See e.g., Horiuchi et al., Rheumatology et al. 49:1215).

Non-human Mammary Gland Epithelial Cells and Transgenic Animals

In one aspect, the disclosure provides mammary gland epithelial cells that produce highly galactosylated anti-TNF-alpha antibodies or populations of anti-TNF-alpha antibodies with a high level of galactosylation.

In one aspect, the disclosure provides a transgenic non-human mammal that produces highly galactosylated anti-TNF-alpha antibody or populations of anti-TNF-alpha antibodies with a high level of galactosylation In one aspect, the disclosure relates to mammalian mammary epithelial cells that produce glycosylated antibodies. Methods are provided herein for producing glycosylated antibodies in mammalian mammary epithelial cells. This can be accomplished in cell culture by culturing mammary epithelial cell (in vitro or ex vivo). This can also be accomplished in a transgenic animal (in vivo).

In some embodiments, the mammalian mammary gland epithelial cells are in a transgenic animal. In some embodiments, the mammalian mammary gland epithelial cells have been engineered to express recombinant antibodies in the milk of a transgenic animal, such as a mouse or goat. To accomplish this, the expression of the gene(s) encoding the recombinant protein can be, for example, under the control of the goat β-casein regulatory elements. Expression of recombinant proteins, e.g., antibodies, in both mice and goat milk has been established previously (see, e.g., US Patent Application US-2008-0118501-A1). In some embodiments, the expression is optimized for individual mammary duct epithelial cells that produce milk proteins.

Transgenic animals capable of producing recombinant antibodies can be generated according to methods known in the art (see, e.g., U.S. Pat. No. 5,945,577 and US Patent Application US-2008-0118501-A1). Animals suitable for transgenic expression, include, but are not limited to goat, sheep, bison, camel, cow, pig, rabbit, buffalo, horse, rat, mouse or llama. Suitable animals also include bovine, caprine, ovine and porcine, which relate to various species of cows, goats, sheep and pigs (or swine), respectively. Suitable animals also include ungulates. As used herein, "ungulate" is of or relating to a hoofed typically herbivorous quadruped mammal, including, without limitation, sheep, swine, goats, cattle and horses. Suitable animals also include dairy animals, such as goats and cattle, or mice. In some embodiments, the animal suitable for transgenic expression is a goat.

In one embodiment, transgenic animals are generated by generation of primary cells comprising a construct of interest followed by nuclear transfer of primary cell nucleus into enucleated oocytes. Primary cells comprising a construct of interest are produced by injecting or transfecting primary cells with a single construct comprising the coding sequence of an antibody of interest, e.g., the heavy and light chains of adalimumab, or by co-transfecting or co-injecting primary cells with separate constructs comprising the coding sequences of the heavy and light chains of an antibody, e.g., adalimumab. These cells are then expanded and characterized to assess transgene copy number, transgene structural integrity and chromosomal integration site. Cells with desired transgene copy number, transgene structural integrity and chromosomal integration site are then used for nuclear transfer to produce transgenic animals. As used herein, "nuclear transfer" refers to a method of cloning wherein the nucleus from a donor cell is transplanted into an enucleated oocyte.

Coding sequences for antibodies to be expressed in mammalian mammary epithelial cells can be obtained by screening libraries of genomic material or reverse-translated messenger RNA derived from the animal of choice (such as humans, cattle or mice), from sequence databases such as NCBI, Genbank, or by obtaining the sequences of antibodies using methods known in the art, e.g. peptide mapping. The sequences can be cloned into an appropriate plasmid vector and amplified in a suitable host organism, like *E. coli*. As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques.

The coding sequence of antibodies or the heavy and light chains of antibodies of interest can be operatively linked to a control sequence which enables the coding sequence to be expressed in the milk of a transgenic non-human mammal. After amplification of the vector, the DNA construct can be excised, purified from the remains of the vector and introduced into expression vectors that can be used to produce transgenic animals. The transgenic animals will have the desired transgenic protein integrated into their genome.

A DNA sequence which is suitable for directing production to the milk of transgenic animals can carry a 5'-promoter region derived from a naturally-derived milk protein. This promoter is consequently under the control of hormonal and tissue-specific factors and is most active in lactating mammary tissue. In some embodiments the promoter used is a milk-specific promoter. As used herein, a "milk-specific promoter" is a promoter that naturally directs expression of a gene in a cell that secretes a protein into milk (e.g., a mammary epithelial cell) and includes, for example, the casein promoters, e.g., α-casein promoter (e.g., alpha S-1 casein promoter and alpha S2-casein promoter), β-casein promoter (e.g., the goat beta casein gene promoter (DiTullio, BIOTECHNOLOGY 10:74-77, 1992), γ-casein promoter, κ-casein promoter, whey acidic protein (WAP) promoter (Gorton et al., BIOTECHNOLOGY 5: 1183-1187, 1987), β-lactoglobulin promoter (Clark et al., BIOTECHNOLOGY 7: 487-492, 1989) and α-lactalbumin promoter (Soulier et al., FEBS LETTS. 297:13, 1992). Also included in this definition are promoters that are specifically activated in mammary tissue, such as, for example, the long terminal repeat (LTR) promoter of the mouse mammary tumor virus (MMTV). In some embodiments the promoter is a caprine beta casein promoter.

The promoter can be operably linked to a DNA sequence directing the production of a protein leader sequence which directs the secretion of the transgenic protein across the mammary epithelium into the milk. As used herein, a coding sequence and regulatory sequences (e.g., a promoter) are said to be "operably joined" or "operably linked" when they are linked in such a way as to place the expression or transcription of the coding sequence under the influence or control of the regulatory sequences. As used herein, a "leader sequence" or "signal sequence" is a nucleic acid sequence that encodes a protein secretory signal, and, when operably linked to a downstream nucleic acid molecule encoding a transgenic protein directs secretion. The leader sequence may be the native human leader sequence, an artificially-derived leader, or may be obtained from the same gene as the promoter used to direct transcription of the transgene coding sequence, or from another protein that is normally secreted from a cell, such as a mammalian mammary epithelial cell. In some embodiments a 3'-sequence, which can be derived from a naturally secreted milk protein, can be added to improve stability of mRNA.

In some embodiments, to produce primary cell lines containing a construct (e.g., encoding an adalimumab antibody) for use in producing transgenic goats by nuclear transfer, the heavy and light chain constructs can be transfected into primary goat skin epithelial cells, which are expanded and fully characterized to assess transgene copy number, transgene structural integrity and chromosomal integration site. As used herein, "nuclear transfer" refers to a method of cloning wherein the nucleus from a donor cell is transplanted into an enucleated oocyte.

Cloning will result in a multiplicity of transgenic animals—each capable of producing an antibody or other gene construct of interest. The production methods include the use of the cloned animals and the offspring of those animals. Cloning also encompasses the nuclear transfer of fetuses, nuclear transfer, tissue and organ transplantation and the creation of chimeric offspring. One step of the cloning process comprises transferring the genome of a cell, e.g., a primary cell that contains the transgene of interest into an enucleated oocyte. As used herein, "transgene" refers to any piece of a nucleic acid molecule that is inserted by artifice into a cell, or an ancestor thereof, and becomes part of the genome of an animal which develops from that cell. Such a transgene may include a gene which is partly or entirely exogenous (i.e., foreign) to the transgenic animal, or may represent a gene having identity to an endogenous gene of the animal. Suitable mammalian sources for oocytes include goats, sheep, cows, pigs, rabbits, guinea pigs, mice, hamsters, rats, non-human primates, etc. Preferably, oocytes are obtained from ungulates, and most preferably goats or cattle. Methods for isolation of oocytes are well known in the art. Essentially, the process comprises isolating oocytes from the ovaries or reproductive tract of a mammal, e.g., a goat. A readily available source of ungulate oocytes is from hormonally-induced female animals. For the successful use of techniques such as genetic engineering, nuclear transfer and cloning, oocytes may preferably be matured in vivo before these cells may be used as recipient cells for nuclear transfer, and before they were fertilized by the sperm cell to develop into an embryo. Metaphase II stage oocytes, which have been matured in vivo, have been successfully used in nuclear transfer techniques. Essentially, mature metaphase II oocytes are collected surgically from either non-super ovulated or super ovulated animals several hours past the onset of estrus or past the injection of human chorionic gonadotropin (hCG) or similar hormone.

In some embodiments, the transgenic animals (e.g., goats) and mammary epithelial cells are generated through microinjection. Microinjection in goats is described for instance in U.S. Pat. No. 7,928,064. Briefly, fertilized goat eggs are collected from the PBS oviductal flushings on a stereomicroscope, and washed in medium containing 10% fetal bovine serum (FBS). In cases where the pronuclei were visible, the embryos can be immediately microinjected. If pronuclei are not visible, the embryos can be placed media for short term culture until the pronuclei became visible (Selgrath, et al., Theriogenology, 1990. p. 1195-1205). One-cell goat embryos are placed in a microdrop of medium under oil on a glass depression slide. Fertilized eggs having two visible pronuclei and can be immobilized on a flame-polished holding micropipet on an upright microscope with a fixed stage. A pronucleus can be microinjected with the appropriate antibody encoding construct in injection buffer using a fine glass microneedle (Selgrath, et al., Theriogenology, 1990. p. 1195-1205). After microinjection, surviving embryos are placed in a culture and incubated until the recipient animals are prepared for embryo transfer (Selgrath, et al., Theriogenology, 1990. p. 1195-1205).

Thus, in one aspect the disclosure provides mammary gland epithelial cells that produce the antibodies or populations of antibodies disclosed herein. In some embodiments, the antibody comprises a nucleic acid comprising SEQ ID NO: 3 and a nucleic acid comprising SEQ ID NO: 4. In some embodiments, the nucleic acid comprising SEQ ID NO: 3 and the nucleic acid comprising SEQ ID NO: 4 are connected. "Connected" is used herein to mean the nucleic acids are physically linked, e.g., within the same vector or within approximately the same genomic location. In some embodiments, the mammary epithelial cells above are in a transgenic non-human mammal. In some embodiments, the transgenic non-human mammal is a goat.

A nucleic acid sequence encoding the heavy chain of adalimumab is provided in SEQ ID NO:3:

ATGGAATTCGGCCTGAGCTGGCTGTTCCTGGTGGCCATCCTGAAGGGCG

TGCAGTGCGAGGTGCAGCTGGTGGAGTCTGGCGGAGGACTGGTGCAGCC

CGGCAGAAGCCTGAGACTGAGCTGCGCCGCCAGCGGCTTCACCTTCGAC

GACTACGCCATGCACTGGGTCCGCCAGGCCCCTGGAAAGGGCCTGGAAT

GGGTGTCCGCCATCACCTGGAACAGCGGCCACATCGACTACGCCGACAG

CGTGGAGGGCAGGTTCACCATCAGCAGGGACAACGCCAAGAACAGCCTG

TACCTGCAGATGAACAGCCTGAGGGCCGAGGACACCGCCGTGTACTACT

GCGCCAAGGTGTCCTACCTGAGCACCGCCAGCAGCCTGGATTACTGGGG

-continued

CCAGGGCACCCTGGTGACCGTGTCCAGCGCCAGCACCAAGGGCCCTAGC

GTGTTCCCTCTGGCCCCCAGCAGCAAGTCTACCTCTGGCGGCACAGCCG

CTCTGGGCTGCCTGGTGAAGGACTACTTCCCCGAGCCCGTGACAGTGTC

CTGGAACTCTGGCGCCCTGACCAGCGGCGTGCACACATTCCCTGCCGTG

CTGCAGAGCAGCGGCCTGTACAGCCTGAGCAGCGTGGTGACAGTGCCTA

GCAGCTCTCTGGGCACCCAGACCTACATCTGCAACGTGAACCACAAGCC

CAGCAACACCAAGGTGGACAAGAAGGTGGAGCCCAAGAGCTGCGACAAG

ACCCACACCTGTCCCCCTTGTCCTGCCCCTGAGCTGCTGGGCGGACCCA

GCGTGTTCCTGTTCCCCCCAAAGCCCAAGGACACCCTGATGATCAGCAG

GACCCCCGAAGTGACCTGCGTGGTGGTGGACGTGTCCCACGAGGACCCT

GAAGTGAAGTTCAATTGGTACGTGGACGGCGTGGAGGTGCACAATGCCA

AGACCAAGCCCAGAGAGGAACAGTACAACAGCACCTACAGGGTGGTGTC

CGTGCTGACCGTGCTGCACCAGGACTGGCTGAACGGCAAAGAGTACAAG

TGCAAGGTCTCCAACAAGGCCCTGCCTGCCCCCATCGAGAAAACCATCA

GCAAGGCCAAGGGCCAGCCCAGAGAACCCCAGGTGTACACCCTGCCCCC

TAGCAGGGACGAGCTGACCAAGAACCAGGTGTCCCTGACCTGTCTGGTG

AAGGGCTTCTACCCCAGCGATATCGCCGTGGAGTGGGAGTCTAACGGCC

AGCCTGAGAACAACTACAAGACCACCCCCCCTGTGCTGGACAGCGACGG

CAGCTTCTTCCTGTACTCCAAACTGACCGTGGACAAGAGCAGATGGCAG

CAGGGCAACGTGTTCAGCTGCAGCGTGATGCACGAGGCCCTGCACAACC

ACTACACCCAGAAGTCCCTGAGCCTGAGCCCCGGCAAGTAATGA

A nucleic acid sequence encoding the light chain of adalimumab is provided in SEQ ID NO:4:

ATGGACATGAGAGTGCCCGCTCAGCTGCTGGGACTGCTGCTGCTGTGGC

TGAGAGGCGCCAGATGCGACATCCAGATGACCCAGAGCCCTTCTAGCCT

GAGCGCCAGCGTGGGCGACAGAGTGACCATCACCTGTAGGGCCAGCCAG

GGCATCAGGAACTACCTGGCCTGGTATCAGCAGAAGCCCGGCAAGGCCC

CCAAGCTGCTGATCTACGCCGCCAGCACCCTGCAGAGCGGCGTGCCCAG

CAGATTCAGCGGCAGCGGCTCCGGCACCGACTTCACCCTGACCATCAGC

AGCCTGCAGCCTGAGGACGTGGCCACCTACTACTGCCAGAGGTACAACA

GGGCCCCCTACACCTTCGGACAGGGCACCAAGGTGGAGATCAAGAGGAC

CGTGGCCGCTCCCAGCGTGTTCATCTTCCCACCCAGCGACGAGCAGCTG

AAGTCTGGCACCGCCTCCGTGGTCTGCCTGCTGAACAACTTCTACCCCC

GCGAGGCCAAGGTGCAGTGGAAGGTGGACAACGCCCTGCAGTCCGGCAA

CAGCCAGGAAAGCGTCACCGAGCAGGACAGCAAGGACTCCACCTACTCC

CTGTCCAGCACCCTGACCCTGAGCAAGGCCGACTACGAGAAGCACAAGG

TGTACGCCTGCGAAGTGACCCACCAGGGCCTGAGCAGCCCTGTGACCAA

GAGCTTCAACAGGGGCGAGTGCTAATGA

In another aspect the disclosure provides a method for the production of a transgenic antibody, and populations thereof, the process comprising expressing in the milk of a transgenic non-human mammal a transgenic antibody encoded by a nucleic acid construct. In some embodiments, the method for producing the antibodies of the disclosure comprises:

(a) transfecting non-human mammalian cells with a transgene DNA construct encoding an anti-TNF-alpha antibody;

(b) selecting cells in which said anti-TNF-alpha transgene DNA construct has been inserted into the genome of the cells; and (c) performing a first nuclear transfer procedure to generate a non-human transgenic mammal heterozygous for the anti-TNF-alpha antibody and that can express it in its milk.

In some embodiments, the anti-TNF-alpha antibody is adalimumab.

In some embodiments, the transgene DNA construct comprises SEQ ID NO:3 and/or SEQ ID NO:4. In some embodiments, the non-human transgenic mammal is a goat. In another aspect, the disclosure provides a method of:

(a) providing a non-human transgenic mammal engineered to express an anti-TNF-alpha antibody, (b) expressing the anti-TNF-alpha antibody in the milk of the non-human transgenic mammal; and (c) isolating the anti-TNF-alpha antibody expressed in the milk.

In some embodiments, the anti-TNF-alpha antibody comprises a heavy chain comprising SEQ ID NO:1 and a light chain comprising SEQ ID NO:2. In some embodiments, the anti-TNF-alpha antibody is adalimumab.

One of the tools used to predict the quantity and quality of the recombinant protein expressed in the mammary gland is through the induction of lactation (Ebert K M, 1994). Induced lactation allows for the expression and analysis of protein from the early stage of transgenic production rather than from the first natural lactation resulting from pregnancy, which is at least a year later. Induction of lactation can be done either hormonally or manually.

In some embodiments, the compositions of glycosylated antibodies provided herein further comprise milk. In some embodiments, the methods provided herein include a step of isolating a population of antibodies from the milk of a transgenic animal. Methods for isolating antibodies from the milk of transgenic animal are known in the art and are described for instance in Pollock et al., Journal of Immunological Methods, Volume 231, Issues 1-2, 10 Dec. 1999, Pages 147-157. In some embodiments, the methods provided herein include a step of purifying glycosylated antibodies with a desired amount of galactosylation.

Methods of Treatment, Pharmaceutical Compositions, Dosage, and Administration

In one aspect, the disclosure provides methods comprising administering highly galactosylated antibodies, compositions of highly galactosylated antibodies, populations of antibodies with a high level of galactosylated antibodies or compositions comprising populations of antibodies with a high level of galactosylated antibodies, to a subject in need thereof. In some embodiment, the subject has an inflammatory disorder or autoimmune disorder. In some embodiment, the inflammatory disorder or autoimmune disorder is rheumatoid arthritis, psoriasis, Crohn's disease, juvenile idiopathic arthritis, ankylozing spondylitis, ulcerative colitis, chronic inflammation, hepatitis, Behcet's disease, Wegener's granulomatosis, or sarcoidosis.

In one aspect, the disclosure provides methods for administering any one of antibodies or compositions described herein to a subject in need thereof. In some embodiments, the subject has an immune disorder or disorder associated with inflammation. Immune disorders and disorders associated with inflammation include but are not limited, to adult respiratory distress syndrome, arteriosclerosis, asthma, atherosclerosis, cholecystitis, cirrhosis, Crohn's disease, diabetes mellitus, emphysema, hypereosinophilia, inflammation, irritable bowel syndrome, multiple sclerosis, myasthenia gravis, myocardial or pericardial inflammation, osteoarthritis, osteoporosis, pancreatitis, rheumatoid arthritis, scleroderma, colitis, systemic lupus erythematosus, lupus nephritis, diabetes mellitus, inflammatory bowel disease, celiac disease, an autoimmune thyroid disease, Addison's disease, Sjogren's syndrome, Sydenham's chorea, Takayasu's arteritis, Wegener's granulomatosis, autoimmune gastritis, autoimmune hepatitis, cutaneous autoimmune diseases, autoimmune dilated cardiomyopathy, multiple sclerosis, myocarditis, myasthenia gravis, pernicious anemia, polymyalgia, psoriasis, rapidly progressive glomerulonephritis, rheumatoid arthritis, ulcerative colitis, vasculitis, autoimmune diseases of the muscle, autoimmune diseases of the testis, autoimmune diseases of the ovary and autoimmune diseases of the eye, acne vulgari, asthma, autoimmune diseases, celiac disease, chronic prostatitis, glomerulonephritis, hypersensitivities, inflammatory bowel diseases, pelvic inflammatory disease, peperfusion injury, rheumatoid arthritis, sarcoidosis, transplant rejection, vasculitis, and interstitial cystitis.

In one aspect, the disclosure provides methods for administering any one of antibodies or compositions described herein to a subject in need thereof. In some embodiments, a subject in need of treatments is a subject with a disease characterized by a dysregulation of TNF levels. Disease characterized by a dysregulation of TNF levels, in addition to the inflammatory and immune disorders discussed above, include Alzheimer, cancer and depression.

In one aspect, the disclosure provides pharmaceutical compositions which comprise an amount of an antibody or population of antibodies and a pharmaceutically acceptable vehicle, diluent or carrier. In some embodiments, the compositions comprise milk.

In one aspect, the disclosure provides a method of treating a subject, comprising administering to a subject a composition provided in an amount effective to treat a disease the subject has or is at risk of having is provided. In one embodiment the subject is a human. In another embodiment the subject is a non-human animal, e.g., a dog, cat, horse, cow, pig, sheep, goat or primate.

According to embodiments that involve administering to a subject in need of treatment a therapeutically effective amount of the antibodies as provided herein, "therapeutically effective" or "an amount effective to treat" denotes the amount of antibody or of a composition needed to inhibit or reverse a disease condition (e.g., to treat the inflammation). Determining a therapeutically effective amount specifically depends on such factors as toxicity and efficacy of the medicament. These factors will differ depending on other factors such as potency, relative bioavailability, patient body weight, severity of adverse side-effects and preferred mode of administration. Toxicity may be determined using methods well known in the art. Efficacy may be determined utilizing the same guidance. Efficacy, for example, can be measured by a decrease in inflammation. A pharmaceutically effective amount, therefore, is an amount that is deemed by the clinician to be toxicologically tolerable, yet efficacious.

Dosage may be adjusted appropriately to achieve desired drug (e.g., anti-TNF-alpha antibodies) levels, local or systemic, depending upon the mode of administration. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of antibodies. Appropriate systemic levels can be determined by, for example, measurement of the patient's peak or sustained plasma level of the drug. "Dose" and "dosage" are used interchangeably herein.

In some embodiments, the amount of antibody or pharmaceutical composition administered to a subject is 50 to 500 mg/kg, 100 to 400 mg/kg, or 200 to 300 mg/kg per week. In one embodiment the amount of antibody or pharmaceutical composition administered to a subject is 250 mg/kg per week. In some embodiments, an initial dose of 400 mg/kg is administered a subject the first week, followed by administration of 250 mg/kg to the subject in subsequent weeks. In some embodiments the administration rate is less than 10 mg/min. In some embodiments, administration of the antibody or pharmaceutical composition to a subject occurs at least one hour prior to treatment with another therapeutic agent. In some embodiments, a pre-treatment is administered prior to administration of the antibody or pharmaceutical composition.

In some embodiments the compositions provided are employed for in vivo applications. Depending on the intended mode of administration in vivo the compositions used may be in the dosage form of solid, semi-solid or liquid such as, e.g., tablets, pills, powders, capsules, gels, ointments, liquids, suspensions, or the like. Preferably, the compositions are administered in unit dosage forms suitable for single administration of precise dosage amounts. The compositions may also include, depending on the formulation desired, pharmaceutically acceptable carriers or diluents, which are defined as aqueous-based vehicles commonly used to formulate pharmaceutical compositions for animal or human administration. The diluent is selected so as not to affect the biological activity of the human recombinant protein of interest. Examples of such diluents are distilled water, physiological saline, Ringer's solution, dextrose solution, and Hank's solution. The same diluents may be used to reconstitute a lyophilized recombinant protein of interest. In addition, the pharmaceutical composition may also include other medicinal agents, pharmaceutical agents, carriers, adjuvants, nontoxic, non-therapeutic, non-immunogenic stabilizers, etc. Effective amounts of such diluent or carrier are amounts which are effective to obtain a pharmaceutically acceptable formulation in terms of solubility of components, biological activity, etc. In some embodiments the compositions provided herein are sterile.

Administration during in vivo treatment may be by any number of routes, including oral, parenteral, intramuscular, intranasal, sublingual, intratracheal, inhalation, ocular, vaginal, and rectal. Intracapsular, intravenous, and intraperitoneal routes of administration may also be employed. The skilled artisan recognizes that the route of administration varies depending on the disorder to be treated. For example, the compositions or antibodies herein may be administered to a subject via oral, parenteral or topical administration. In one embodiment, the compositions or antibodies herein are administered by intravenous infusion.

The compositions, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compositions in water soluble form. Additionally, suspensions of the active compositions may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compositions to allow for the preparation of highly concentrated solutions. Alternatively, the active compositions may be in powder form for constitution with a suitable vehicle, e.g., sterile pyrogen-free water, before use.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. The component or components may be chemically modified so that oral delivery of the antibodies is efficacious. Generally, the chemical modification contemplated is the attachment of at least one molecule to the antibodies, where said molecule permits (a) inhibition of proteolysis; and (b) uptake into the blood stream from the stomach or intestine. Also desired is the increase in overall stability of the antibodies and increase in circulation time in the body. Examples of such molecules include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol molecules. For oral compositions, the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the antibody or by release of the biologically active material beyond the stomach environment, such as in the intestine.

For buccal administration, the compositions may take the form of tablets or lozenges formulated in conventional manner.

For administration by inhalation, the compositions for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compositions and a suitable powder base such as lactose or starch.

Also contemplated herein is pulmonary delivery. The compositions can be delivered to the lungs of a mammal while inhaling and traverses across the lung epithelial lining to the blood stream. Contemplated for use in the practice of this disclosure are a wide range of mechanical devices designed for pulmonary delivery of therapeutic products, including but not limited to nebulizers, metered dose inhalers, and powder inhalers, all of which are familiar to those skilled in the art.

Nasal delivery of a pharmaceutical composition disclosed herein is also contemplated. Nasal delivery allows the passage of a pharmaceutical composition of the present disclosure to the blood stream directly after administering the therapeutic product to the nose, without the necessity for deposition of the product in the lung. Formulations for nasal delivery include those with dextran or cyclodextran.

The compositions may also be formulated in rectal or vaginal compositions such as suppositories or retention enemas, e.g., containing conventional suppository bases such as cocoa butter or other glycerides.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compositions, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249:1527-1533, 1990, which is incorporated herein by reference.

The antibodies and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the disclosure contain an effective amount of the antibodies and optionally therapeutic agents included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compositions of the present disclosure, and with each other, in a manner such that there is no interaction which would substantially impair the desired pharmaceutical efficiency.

The therapeutic agent(s), including specifically but not limited to the antibodies, may be provided in particles. Particles as used herein means nano or microparticles (or in some instances larger) which can consist in whole or in part of the antibody or other therapeutic agents administered with the antibody. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the antibody in a solution or in a semi-solid state. The particles may be of virtually any shape.

Methods of Production of Antibodies

In one aspect, the disclosure provides methods for production of highly galactosylated anti-TNF-alpha antibodies and populations with high levels of galactosylated antibodies.

In one aspect, the disclosure provides a method for producing a population of antibodies, comprising: expressing the population of antibodies in mammary gland epithelial cells of a non-human mammal such that a population of antibodies is produced, wherein the antibody is an anti-TNF-alpha antibody, and wherein the level of galactosylation of the antibodies in the population is at least 70%. In some embodiments, the anti-TNF-alpha antibody is adalimumab. In some embodiments, the mammary gland epithelial cells are in culture and are transfected with a nucleic acid that comprises a sequence that encodes the antibody. In some embodiments, the nucleic acid comprise SEQ ID NO:3 and SEQ ID NO:4. In some embodiments, the mammary gland epithelial cells are in a non-human mammal engineered to express a nucleic acid that comprises a sequence that encodes the antibody in its mammary gland. In some embodiments, the mammary gland epithelial cells are goat, sheep, bison, camel, cow, pig, rabbit, buffalo, horse, rat, mouse or llama mammary gland epithelial cells. In some embodiments, the mammary gland epithelial cells are goat mammary gland epithelial cells.

In one aspect the disclosure provides mammary gland epithelial cells that express the highly galactosylated anti-TNF-alpha antibodies or populations with high levels of galactosylated antibodies disclosed herein.

In one aspect the disclosure provides a transgenic non-human mammal comprising mammary gland epithelial cells that express the highly galactosylated anti-TNF-alpha antibodies or populations with high levels of galactosylated antibodies disclosed herein.

In one aspect the disclosure provides a method for the production of a glycosylated antibody or population of glycosylated antibodies, the process comprising expressing in the milk of a transgenic non-human mammal a glycosylated antibody encoded by a nucleic acid construct. In one embodiment the mammalian mammary epithelial cells are of a non-human mammal engineered to express the antibody in its milk. In yet another embodiment the mammalian mammary epithelial cells are mammalian mammary epithelial cells in culture.

In another embodiment the method comprises:
(a) providing a non-human transgenic mammal engineered to express an antibody,
(b) expressing the antibody in the milk of the non-human transgenic mammal;
(c) isolating the antibodies expressed in the milk; and
(d) detecting the presence galactose on the isolated antibodies.

In yet another embodiment the method, comprises: producing a population of glycosylated antibodies in mammary gland epithelial cells such that the population of glycosylated antibodies produced comprises a specific percentage of galactosylation (e.g., at least 70%, at least 80%, at least 90%, or higher). In some embodiment, the antibody is an anti-TNF-alpha antibody. In some embodiments, the glycosylated antibodies comprise a heavy chain comprising SEQ ID NO:1 and a light chain comprising SEQ ID NO:2. In some embodiments, this method is performed in vitro. In other embodiments, this method is performed in vivo, e.g., in the mammary gland of a transgenic goat.

In some embodiments the methods above further comprise steps for inducing lactation. In still other embodiments the methods further comprise additional isolation and/or purification steps. In yet other embodiments the methods further comprise steps for comparing the glycosylation pattern of the antibodies obtained with antibodies produced in cell culture, e.g. non-mammary cell culture. In further embodiments, the methods further comprise steps for comparing the glycosylation pattern of the antibodies obtained to antibodies produced by non-mammary epithelial cells. Such cells can be cells of a cell culture. In some embodiments, the glycosylation pattern is the amount of galactose present on an antibody or population of antibodies. In some embodiments, the method further comprises comparing the percentage of galactosylation present in the population of glycosylated antibodies to the percentage of galactosylation present in a population of glycosylated antibodies produced in cell culture, e.g. non-mammary cell culture. Experimental techniques for assessing the glycosylation pattern of the antibodies can be any of those known to those of ordinary skill in the art or as provided herein, such as below in the Examples. Such methods include, e.g., liquid chromatography mass spectrometry, tandem mass spectrometry, and Western blot analysis.

The antibodies can be obtained, in some embodiments, by collecting the antibodies from the milk of a transgenic animal produced as provided herein or from an offspring of said transgenic animal. In some embodiments the antibodies produced by the transgenic mammal is produced at a level of at least 1 gram per liter of milk produced. Advantageously, the method according to the invention allows the production of more than 4 grams per liter of milk produced, advantageously more than 5, 10, 15, 20, 25, 30, 35, grams per liter, advantageously up to 70 grams per liter.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The methods and techniques of the present disclosure are generally performed according to conventional methods well-known in the art. Generally, nomenclatures used in connection with, and techniques of biochemistry, enzymology, molecular and cellular biology, microbiology, genetics and protein and nucleic acid chemistry and hybridization described herein are those well-known and commonly used in the art. The methods and techniques of the present disclosure are generally performed according to conventional methods well known in the art and as described in various general and more specific references that are cited and discussed throughout the present specification unless otherwise indicated.

The present invention is further illustrated by the following Examples, which in no way should be construed as further limiting. The entire contents of all of the references (including literature references, issued patents, published patent applications, and co pending patent applications) cited throughout this application are hereby expressly incorporated by reference.

EXAMPLES

Materials and Methods
Generation of Transgenic Goats that Produce Adalimumab

Transgenic goats were generated that include the nucleic acid sequence encoding the adalimumab antibody in their genome. The goats producing adalimumab were generated using traditional micoinjection techniques (See e.g., U.S. Pat. No. 7,928,064). The cDNA encoding the heavy and light chain (SEQ ID NO:3 and SEQ ID NO:4) was synthesized based on the published amino acid sequence (U.S. Pat. No. 6,090,382). These DNA sequences were ligated with the beta casein expression vector to yield constructs BC2601 HC and BC2602 LC. In these plasmids, the nucleic acid sequence encoding adalimumab is under the control of a promoter facilitating the expression of adalimumab in the mammary gland of the goats. The prokaryotic sequences were removed and the DNA microinjected into pre-implantation embryos of the goat. These embryos were then transferred to pseudo pregnant females. The progeny that resulted were screened for the presence of the transgenes. Those that carried both chains were identified as transgenic founders.

When age appropriate, the founder animals were bred. Following pregnancy and parturition they were milked. The time course was in days starting lactation after parturation (e.g., day 3, day 7, day 11). The adalimumab antibody was purified from the milk at each time point and characterized as described herein.

Figure 10:
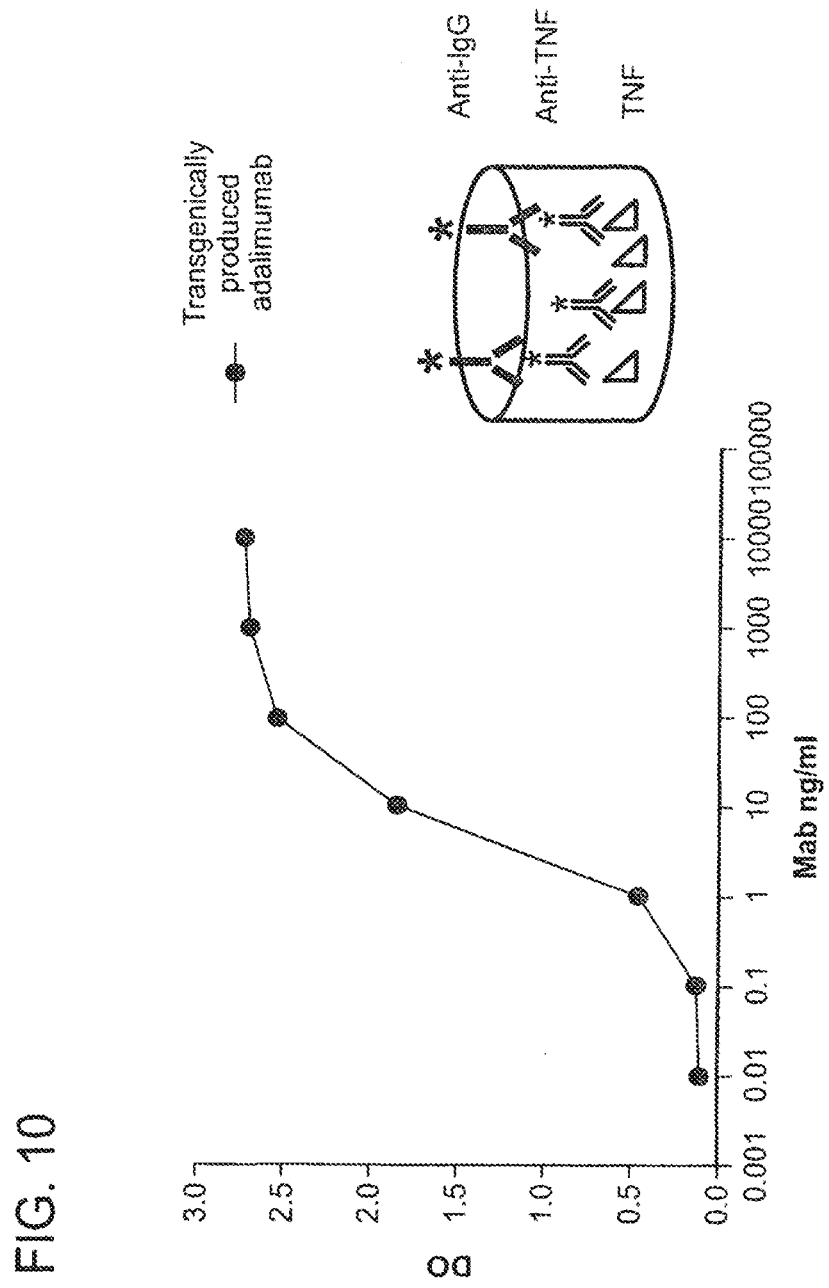
FIG. 10 shows that a transgenically produced adalimumab antibody binds soluble TNF-alpha.

Measuring the Binding of Transgenically Produced Adalimumab by ELISA:

5 µg/ml of TNF-α was coated overnight at 4° C. in a 96 well plate in 100 µl of PBS per well. After blocking of nonspecific sites (incubation with 200 µl PBS/1% BSA, 1 h RT), transgenically produced adalimumab or deglycosylated adalimumab was added at various concentrations (0 to 10 µg/ml) for 20 min in PBS/1% BSA. After washing, the binding of transgenically produced adalimumab to coated TNF-α was evaluated by the addition of a goat anti-human IgG (H+L) coupled to peroxidase, followed by substrate ($H_2O_2$ and tetramethylbenzidine). After 20 min of incubation, the reaction was stopped with 50 µl of diluted $H_2SO_4$ and the OD was read at 450 nm. The results for transgenically produced adalimumab are shown in FIG. 10.

Binding to CD16, Competition of 3G8 Antibody

To evaluate the binding of transgenically produced adalimumab to CD16, a displacement study with the anti-CD16 binding antibody 3G8, (Santa Cruz Biotech) was performed. The displacement test allowed for the determination of the binding of the transgenically produced adalimumab to the CD16 receptor expressed at NK surface membrane.

Figure 11:
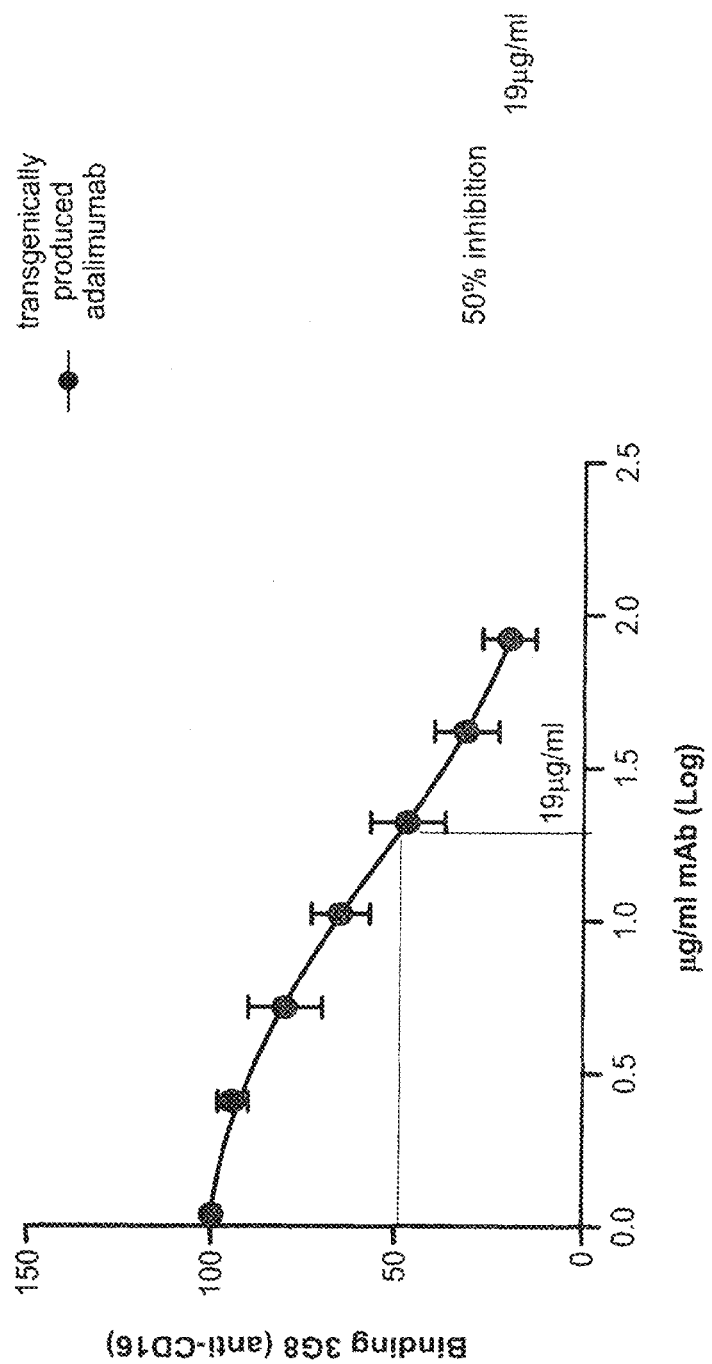
FIG. 11 shows that a transgenically produced adalimumab antibody binds to CD16 expressed on NK cells as shown by a competition assay with the anti-CD16 antibody 3G8.

Natural killer cells (NK cells) were purified by negative depletion (Miltenyi) from the peripheral blood of healthy donors. The NK cells were then incubated with variable concentrations (0 to 83 µg/ml) of transgenically produced adalimumab and the anti-CD16 antibody 3G8 conjugated to a fluorochrome (3G8-PE), at a fixed concentration. After washing, the binding of 3G8-PE to the CD16 receptor on the NK cells was evaluated by flow cytometry. The mean fluorescence values (MFI) observed were expressed as the percent binding, where a value of 100% corresponds the value observed without the tested transgenically produced adalimumab that thus corresponds to maximum 3G8 binding. A value of 0% corresponds to the MFI in the absence of the antibody 3G8. $IC_{50}$, the antibody concentration required to induce inhibition of 3G8 binding by 50% of Imax, were calculated using PRISM software. The results are shown in FIG. 11.

Figure 12:
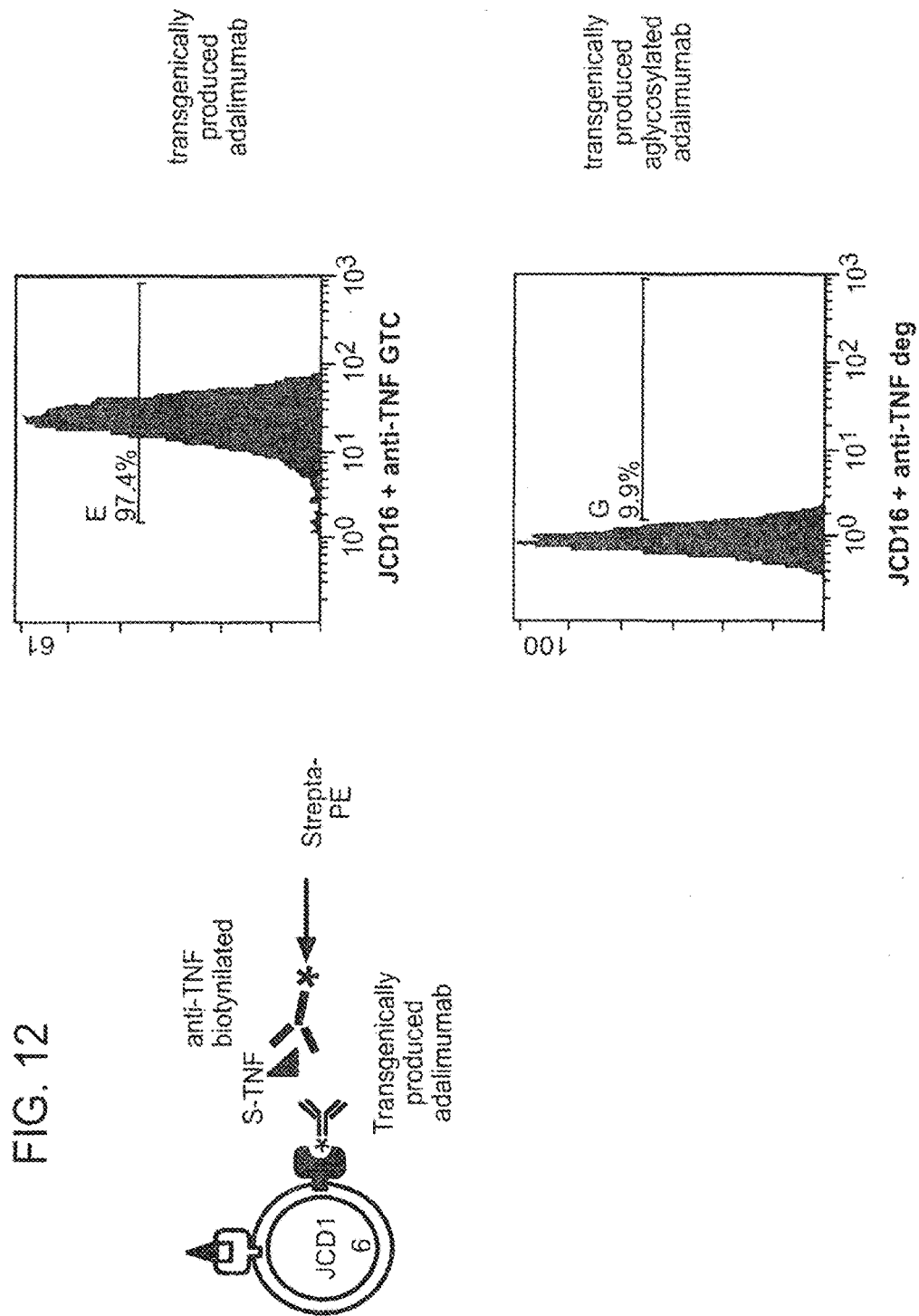
FIG. 12 shows that a transgenically produced adalimumab antibody binds both soluble TNF-alpha and Jurkat expressing CD16 cells while an aglycosylated version of the transgenically produced adalimumab antibody does not.

Binding of Soluble TNF-α with Transgenically Produced Adalimumab on CD16 Expressed by Jurkat Cells Via the Fc Fragment of Transgenically Produced Adalimumab Jurkat-CD16 cells were incubated with 10 µg/ml of transgenically produced adalimumab or the deglycosylated version thereof for 20 min at 4° C. After washing, 100 µl of TNF-α was added to the cell pellet at a final concentration of 1 µg/ml, 20 min at 4° C. After subsequent washing, the cells were incubated with 5 µg/ml of a biotinylated goat anti-human TNF-α antibody, 20 min at 4° C. After another round of washing, the binding of TNF-α was visualized by the addition of streptavidin coupled to PE-fluorochrome for 20 min at 4° C. Samples were analyzed by flux cytometry. The results are shown in FIG. 12.

Example 1

Transgenically Produced Adalimumab

The glycosylation pattern of the adalimumab antibodies produced in the milk of transgenic goats was determined by releasing the N-glycans from antibody and running the released oligosaccharides on a column ("oligosaccharide signature").

Figure 6:
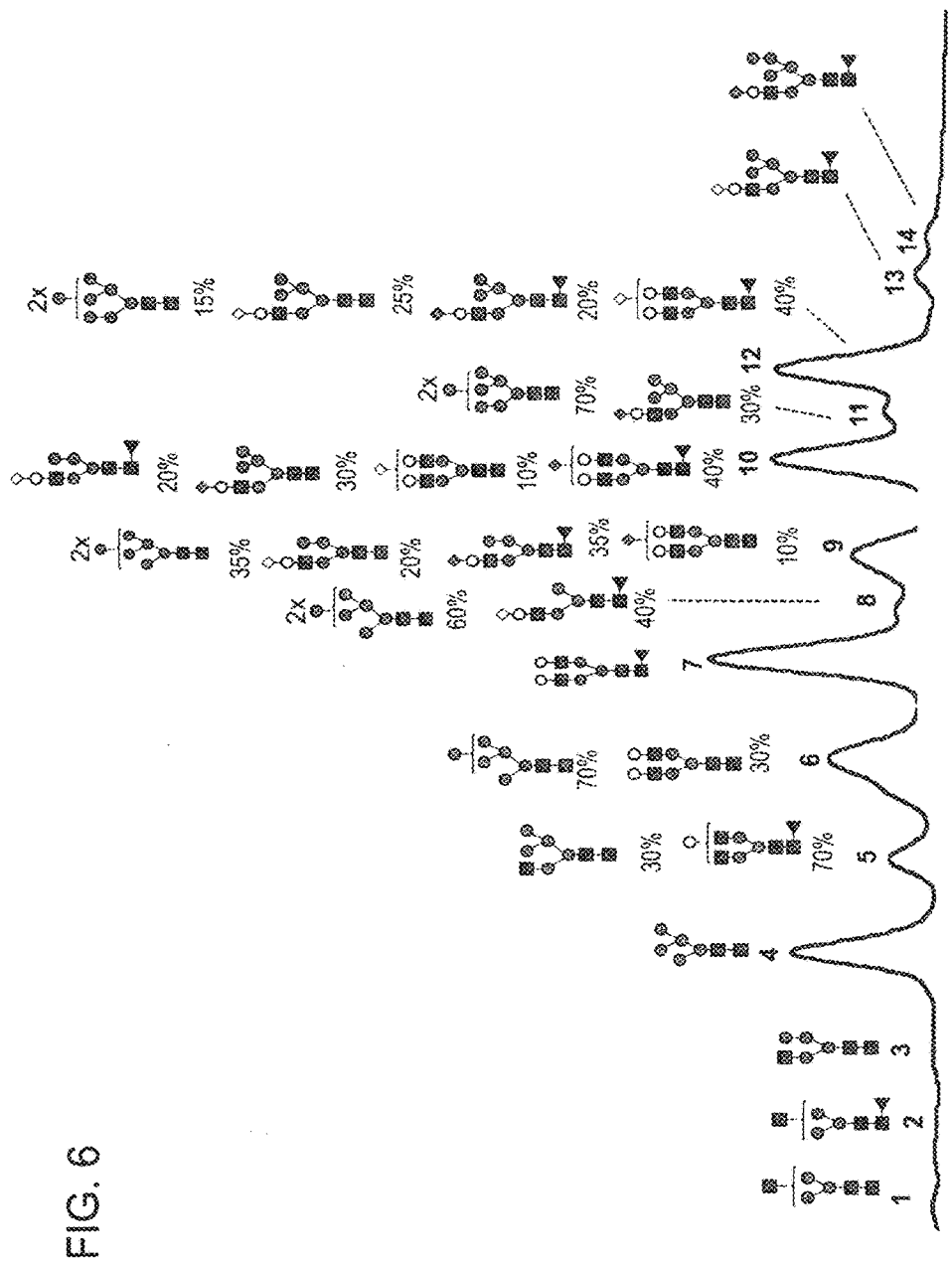
FIG. 6 shows an oligosaccharide signature of N-glycans of a population of highly galactosylated adalimumab antibodies from goat #2 at day 3 of hormone induced lactation.
Figure 7:
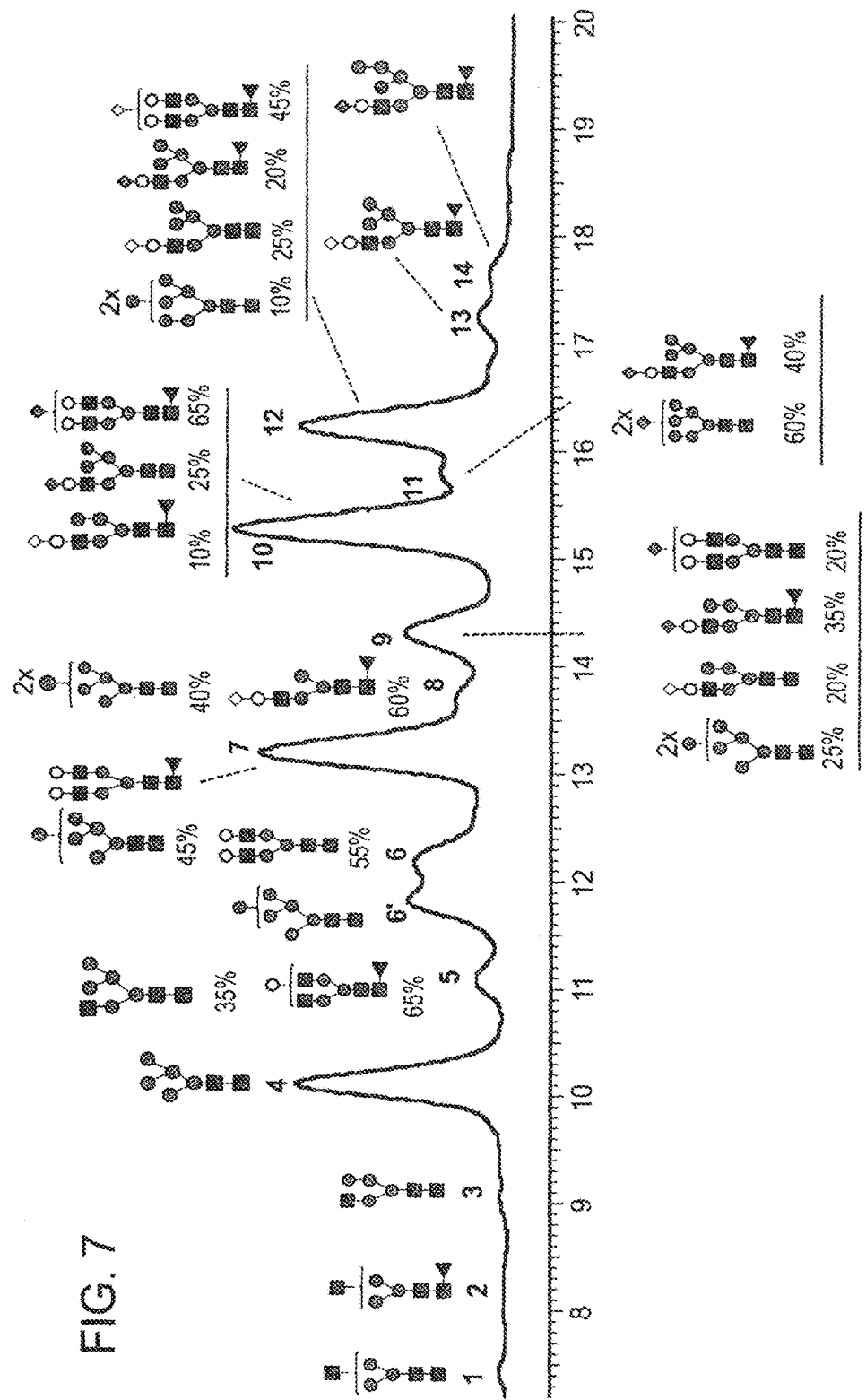
FIG. 7 shows an oligosaccharide signature of N-glycans of a population of highly galactosylated adalimumab antibodies from goat #2 at day 11 of hormone induced lactation.
Figure 8:
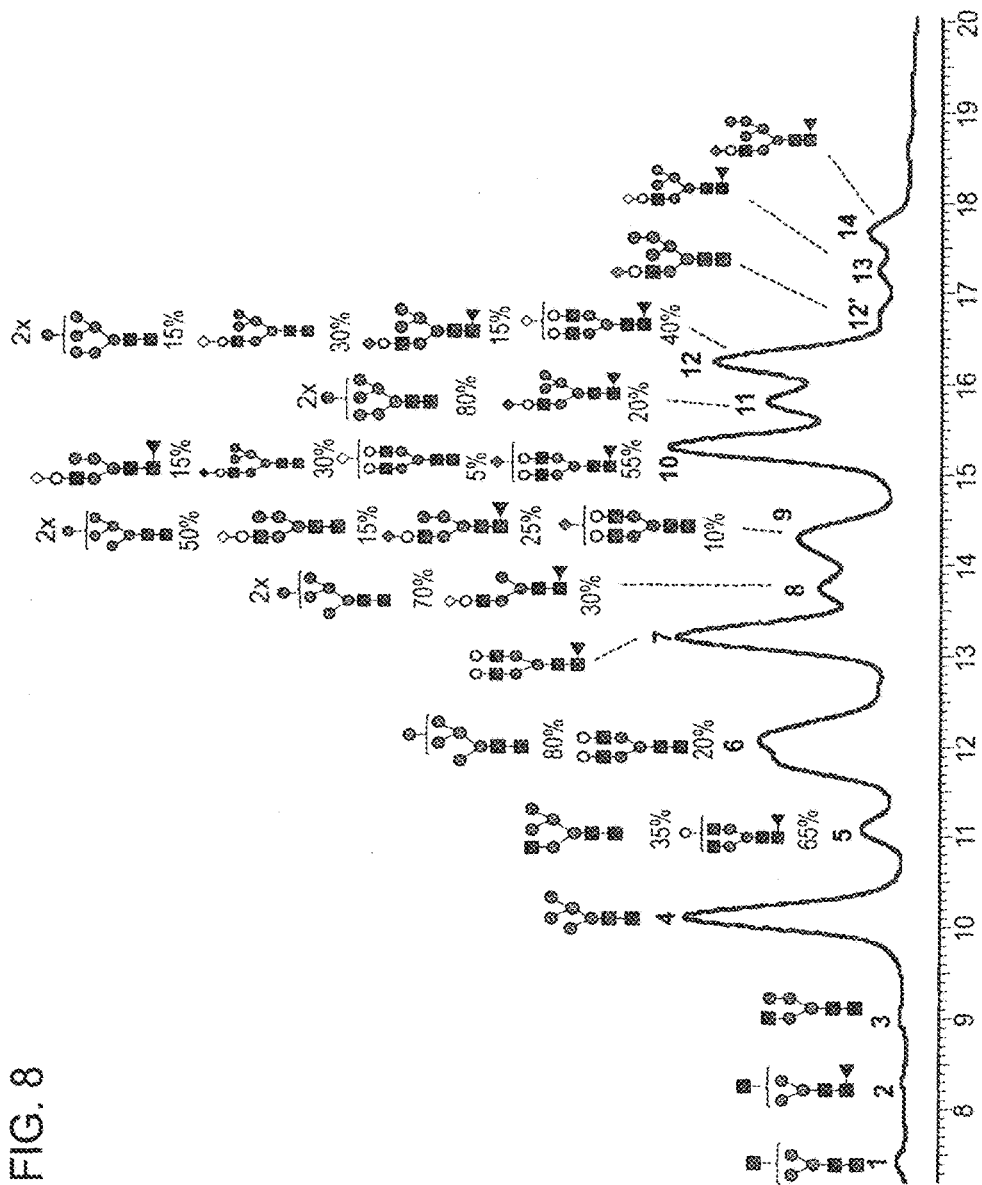
FIG. 8 shows an oligosaccharide signature of N-glycans of a population of highly galactosylated adalimumab antibodies from goat #2 at day 21 of hormone induced lactation.

FIGS. 1-4 and 6-8 show the N-glycan oligosaccharides released from the transgenically produced adalimumab antibody from goat #1 (FIGS. 1-4) and goat #2 (FIGS. 6-8). The monosaccharide groups are depicted as follows:
  Black square: N-AcetylGlucosamine (GlcNac)
  Triangle: Fucose
  Grey Circle: Mannose
  White Circle: Galactose
  Grey Diamond: N-GlycolylNeuraminic Acid (NGNA): a sialic acid
  White Diamond: N-AcetylNeuraminic Acid (NANA): a sialic acid FIG. 1 shows a representative chromatogram of N-glycan oligosaccharides released from the transgenic adalimumab antibody produced in the milk of goat #1. The chromatogram shows that of the fourteen major N-glycan oligosaccharides produced, twelve have at least one galactose in the N-glycan chain, with four oligosaccharides having two galactoses. Only two of the oligosaccharides are purely oligomannose (See peak 1 and peak 3). FIG. 1 also shows that of the fourteen major oligosaccharides produced, nine are fucosylated All of the fucosylated oligosaccharides are also galactosylated.

Figure 2:
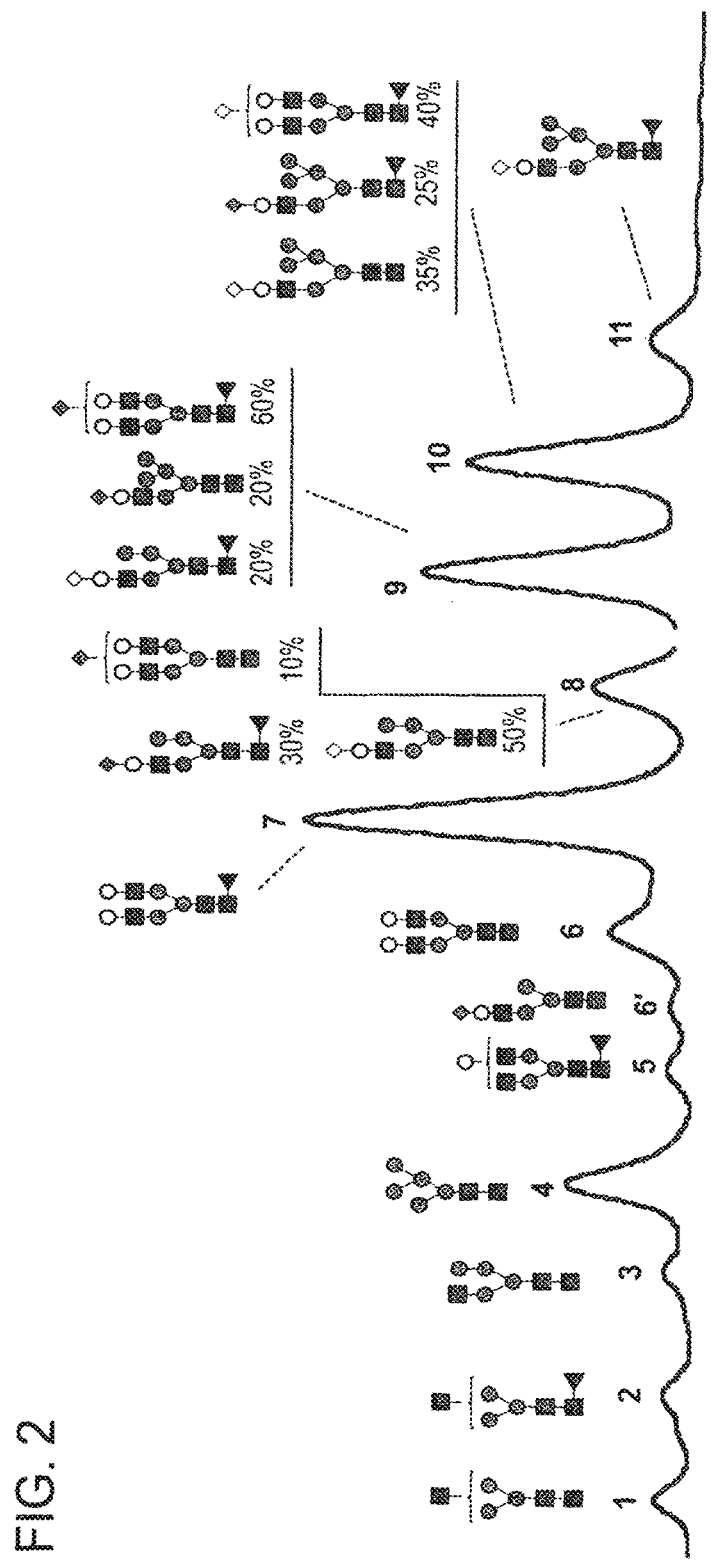
FIG. 2 shows an oligosaccharide signature of N-glycans of a population of highly galactosylated adalimumab antibodies from goat #1 at day 7 of lactation.
Figure 3:
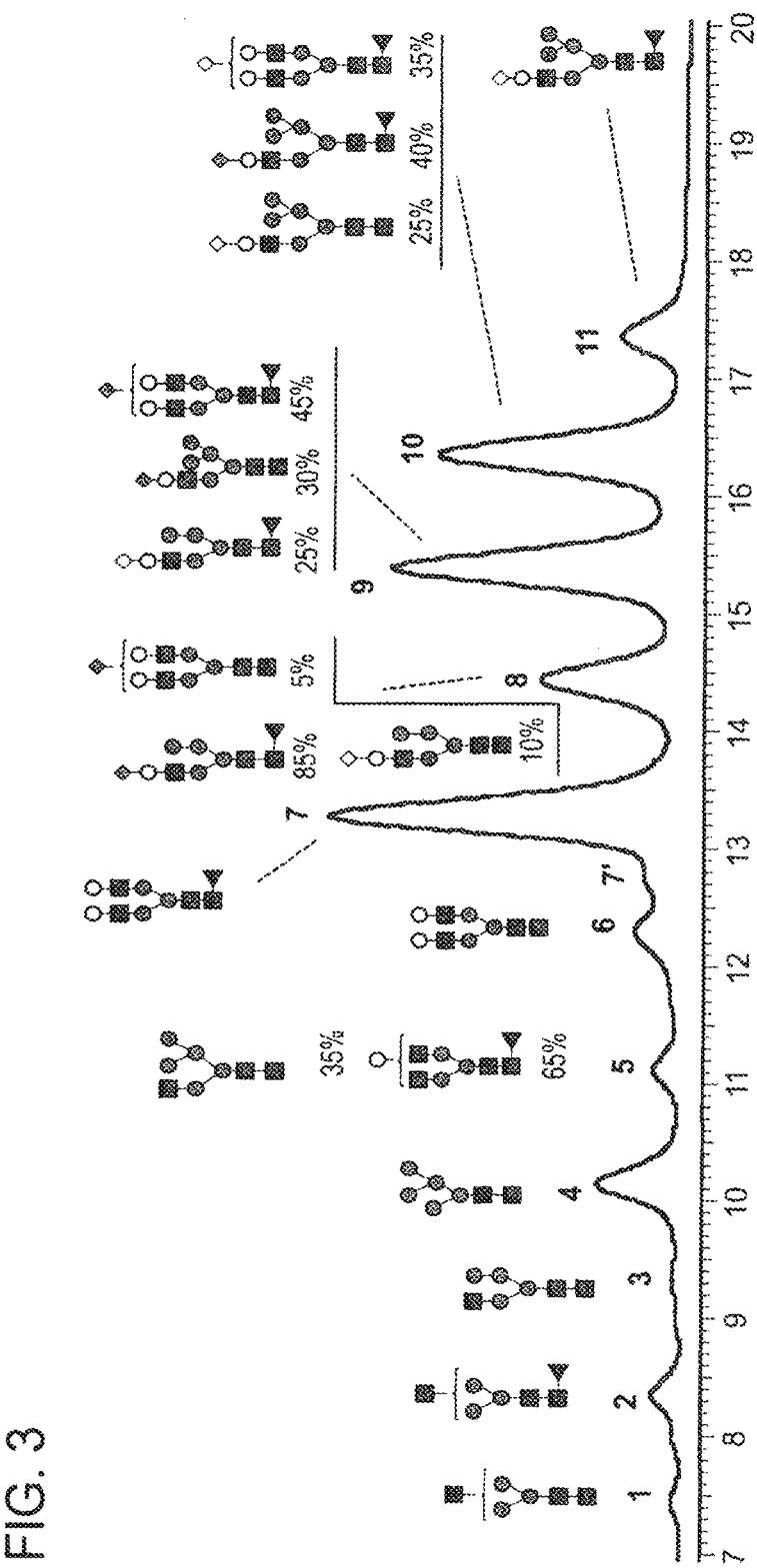
FIG. 3 shows an oligosaccharide signature of N-glycans of a population of highly galactosylated adalimumab antibodies from goat #1 at day 17 of lactation.
Figure 4:
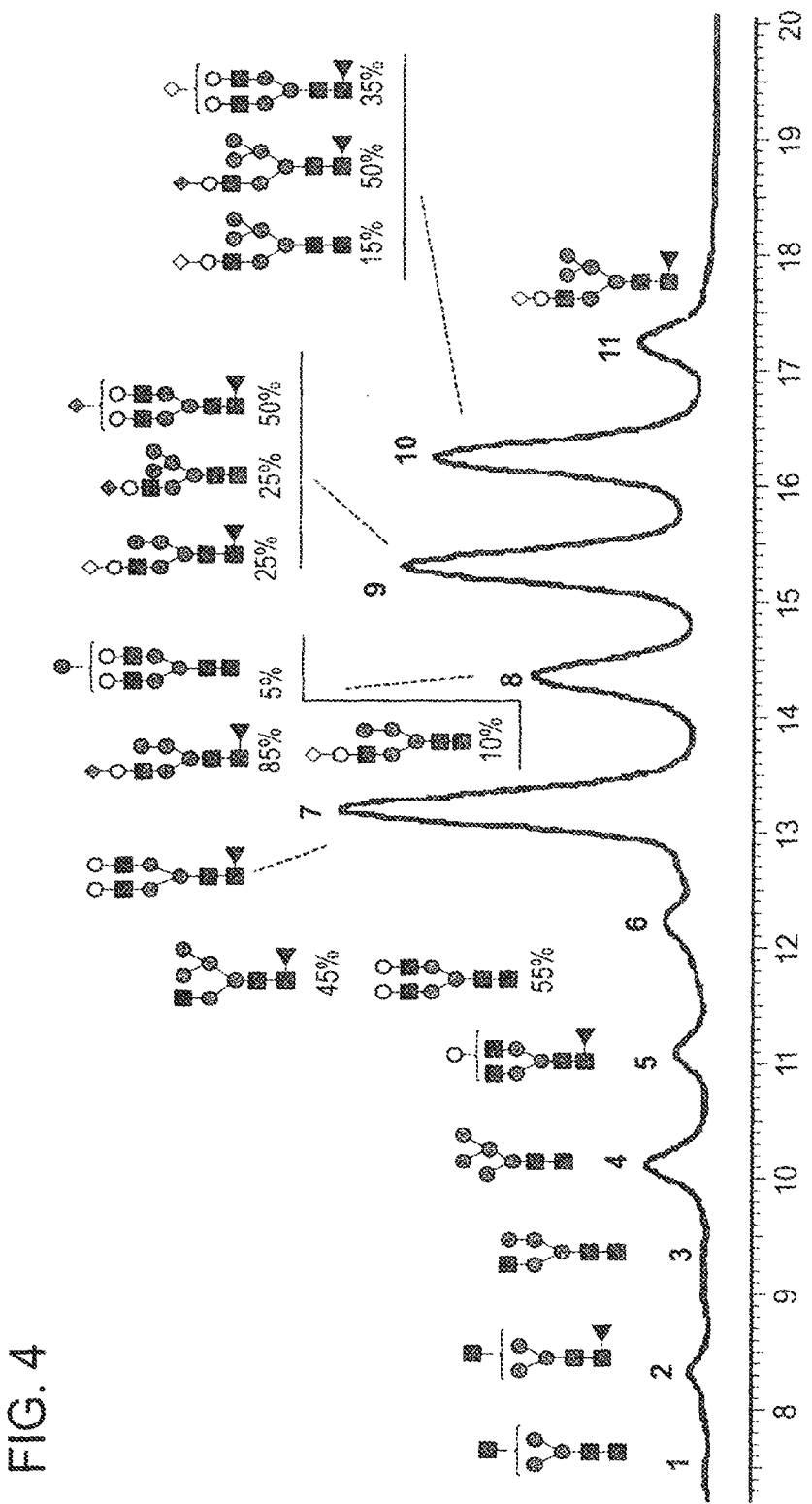
FIG. 4 shows an oligosaccharide signature of N-glycans of a population of highly galactosylated adalimumab antibodies from goat #1 at day 32 of lactation.

FIGS. 2-4 show chromatograms of N-glycan oligosaccharides released from the transgenic adalimumab antibody produced in the milk of goat #1 as harvested after 7 days of lactation (FIG. 2), 17 days of lactation (FIG. 3), and 32 days of lactation (FIG. 4).

The relative percentages of all N-glycan oligosaccharides isolated from the adalimumab antibody produced in the milk of goat #1 are depicted in FIG. 5. FIG. 5 also shows a tabulation of the overall percentage of mono-galactosylation, percentage of bi-galactosylation, percentage of total galactosylation (mono-galactosylation+bi-galactosylation), percentage of galactosylation as calculated according to the formula provided above, percentage of fucosylation as calculated according to the formula provided above, the ratio of galactosylation to fucosylation and the percentage of glycan structures with at least one sialic acid (% sialylation). The results are also summarized in Table 1 below:

TABLE 1

N-glycan oligosaccharides isolated from adalimumab antibodies from goat #1

|  | day 7 | day 17 | day 32 | average |
|---|---|---|---|---|
| mono-Gal (%): | 30.8 | 42.9 | 44.1 | 39.2 |
| bi-Gal (%): | 53.1 | 46.0 | 47.0 | 48.7 |
| mono-Gal + bi-Gal (%) | 83.9 | 88.9 | 91.1 | 88.0 |
| Gal* (%) | 82.9 | 88.2 | 89.8 | 87.0 |
| Fuc* (%) | 63.5 | 74.9 | 81.9 | 73.4 |
| Ratio Gal/Fuc | 1.30 | 1.17 | 1.10 | 1.18 |
| Silaylation (%) | 50.4 | 59.3 | 62.7 | 57.5 |

*calculated according to formulas in specification

FIGS. 6-8 show chromatograms of N-glycan oligosaccharides released from the transgenically produced adalimumab antibody in the milk of goat #2 as harvested after 3 days of lactation (FIG. 6), 11 days of lactation (FIG. 7), and 21 days of hormone induced lactation (FIG. 8).

Figures 2, 9:
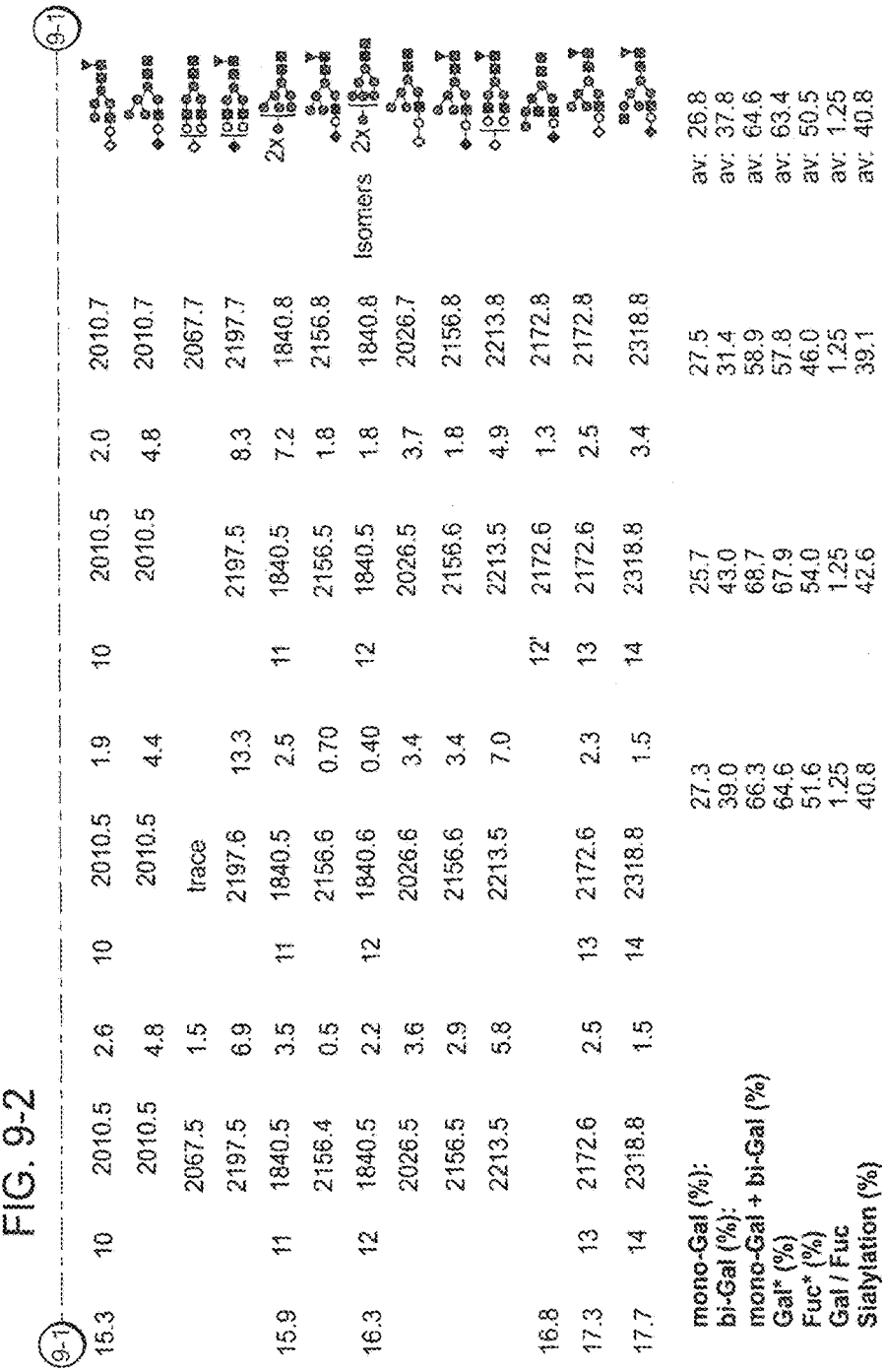
FIG. 9 shows a summary of the percentages of N-glycan oligosaccharides of populations of a highly galactosylated adalimumab antibodies from goat #2 at various days of hormone induced lactation.

The relative percentages of all N-glycan oligosaccharides isolated from the adalimumab antibody produced in the milk of goat #2 are depicted in FIG. 9. FIG. 9 also shows a tabulation of the overall percentage of mono-galactosylation, percentage of bi-galactosylation, percentage of total galactosylation (mono-galactosylation+bi-galactosylation), percentage of galactosylation as calculated according to the formula provided above, percentage of fucosylation as calculated according to the formula provided above, the ratio of galactosylation to fucosylation and the percentage of glycan structures with at least one sialic acid (% sialylation). The results are also summarized below:

TABLE 2

N-glycan oligosaccharides isolated from
adalimumab antibodies from goat #2

|  | day 3 | day 11 | day 21 | average |
|---|---|---|---|---|
| mono-Gal (%): | 27.3 | 25.7 | 27.5 | 26.8 |
| bi-Gal (%): | 39.0 | 43.0 | 31.4 | 37.8 |
| mono-Gal + bi-Gal (%) | 66.3 | 68.7 | 58.9 | 64.6 |
| Gal* (%) | 64.6 | 67.9 | 57.8 | 63.4 |
| Fuc* (%) | 51.6 | 54.0 | 46.0 | 50.5 |
| Gal/Fuc | 1.25 | 1.25 | 1.25 | 1.25 |
| Sialylation (%) | 40.8 | 42.6 | 39.1 | 40.8 |

*calculated according to formulas in specification

Example 2

Binding Studies of Transgenically Produced Adalimumab

FIG. 10 shows that transgenically produced adalimumab can bind soluble TNF-alpha coated in 96-well plates. Transgencially produced adalimumab that was aglycosylated was able to bind soluble TNF-alpha as well (data not shown).

FIG. 11 shows that transgenically produced adalimumab binds CD16 expressed by natural killer (NK) cells. The binding was shown in a competition experiment with the anti-CD16 binding antibody 3G8. The binding of a transgenically produced adalimumab to CD16 is stronger than the binding of a poorly galactosylated antibody to CD16 (data not shown). The transgenically produced adalimumab is therefore expected to have a higher ADCC activity.

FIG. 12 shows that a transgenically produced adalimumab antibody binds both soluble TNF-alpha and Jurkat expressing CD16 cells while an aglycosylated version of the transgenically produced adalimumab antibody does not. The transgenically produced adalimumab antibody therefore is expected to show ADCC activity while the aglycosylated antibody does not.

Example 3

Glycosylation Analysis of Transgenically Produced Adalimumab in Additional Animals

TABLE 3

Summary of adalimumab production data

| Goat | #Days Lactation | Average Milk Volume (mL) | Est. mg/mL in WM | % Agg | Total #mg Purified |
|---|---|---|---|---|---|
| 1 | 32 | 245 | 29 | 20 | 400 (more TBD) |
| 8 | 36 | 350 | 14* | 20 | 1496 |
| 9 | 36 | 382 | 35** | 25 | 3929 |
| 3 | 36*** | 634 | 5 | 14 | 502 |
| 4 | 29*** | 1458 | 4 | 12 | 390 |
| 5 | 29*** | 1663 | 4 | 8 | 341 |
| 6 | 36*** | 1899 | 4 | 12 | 374 |
| 7 | 29*** | 1676 | 5 | 8 | 395 |
| 2 | 36 | 260 | 34** | 3 | 3719 |

*Concentration started at 20 mg/mL and dropped to 10 mg/mL.
**Values could be higher if protein A column was overloaded.
***Lactation volume was still high when dried off.

Figures 3, 13:
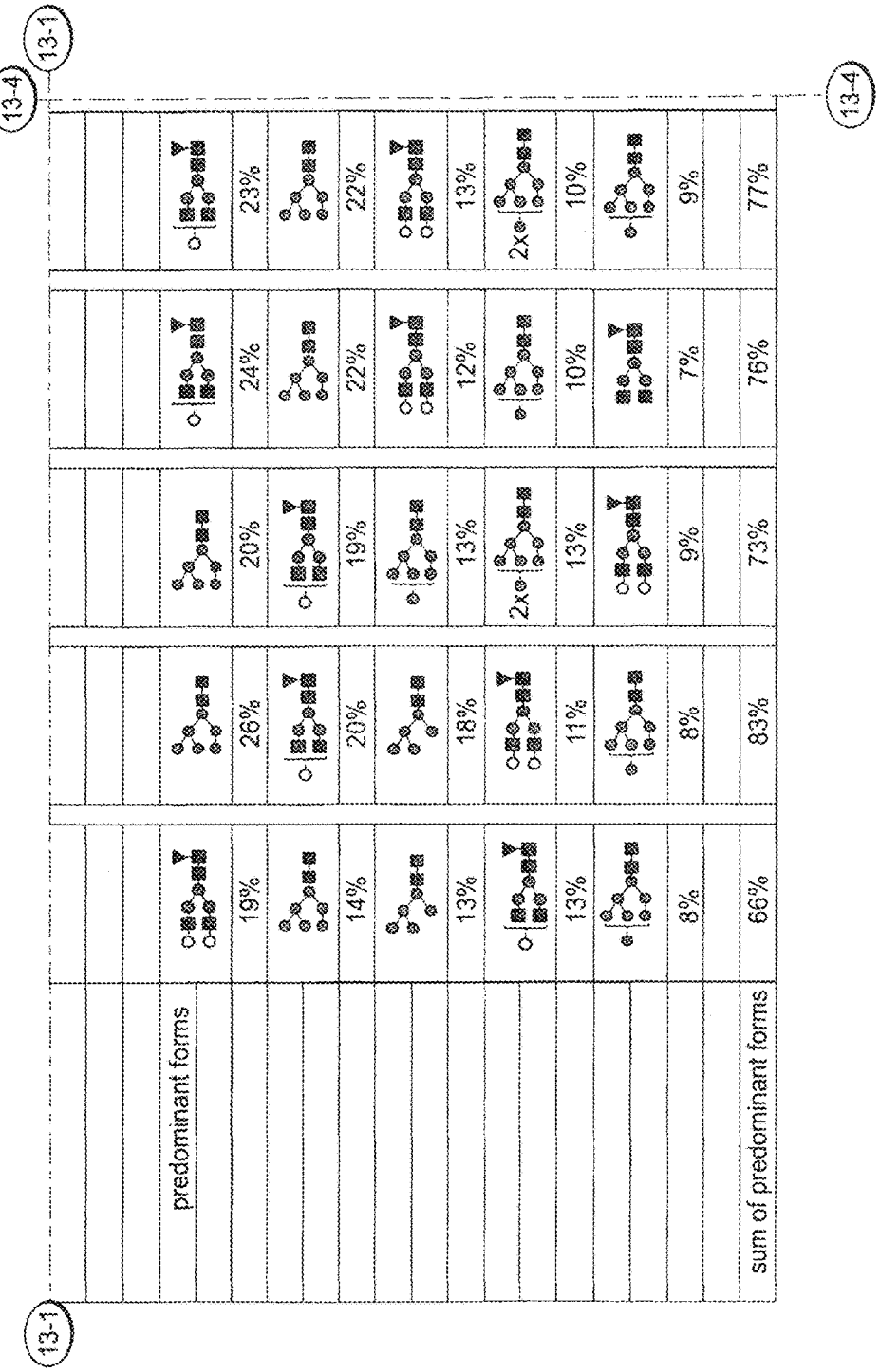
FIG. 13 shows a summary of predominant glycan forms present in populations of transgenically produced adalimumab antibodies from nine different goats #1-9.
Figures 4, 13:
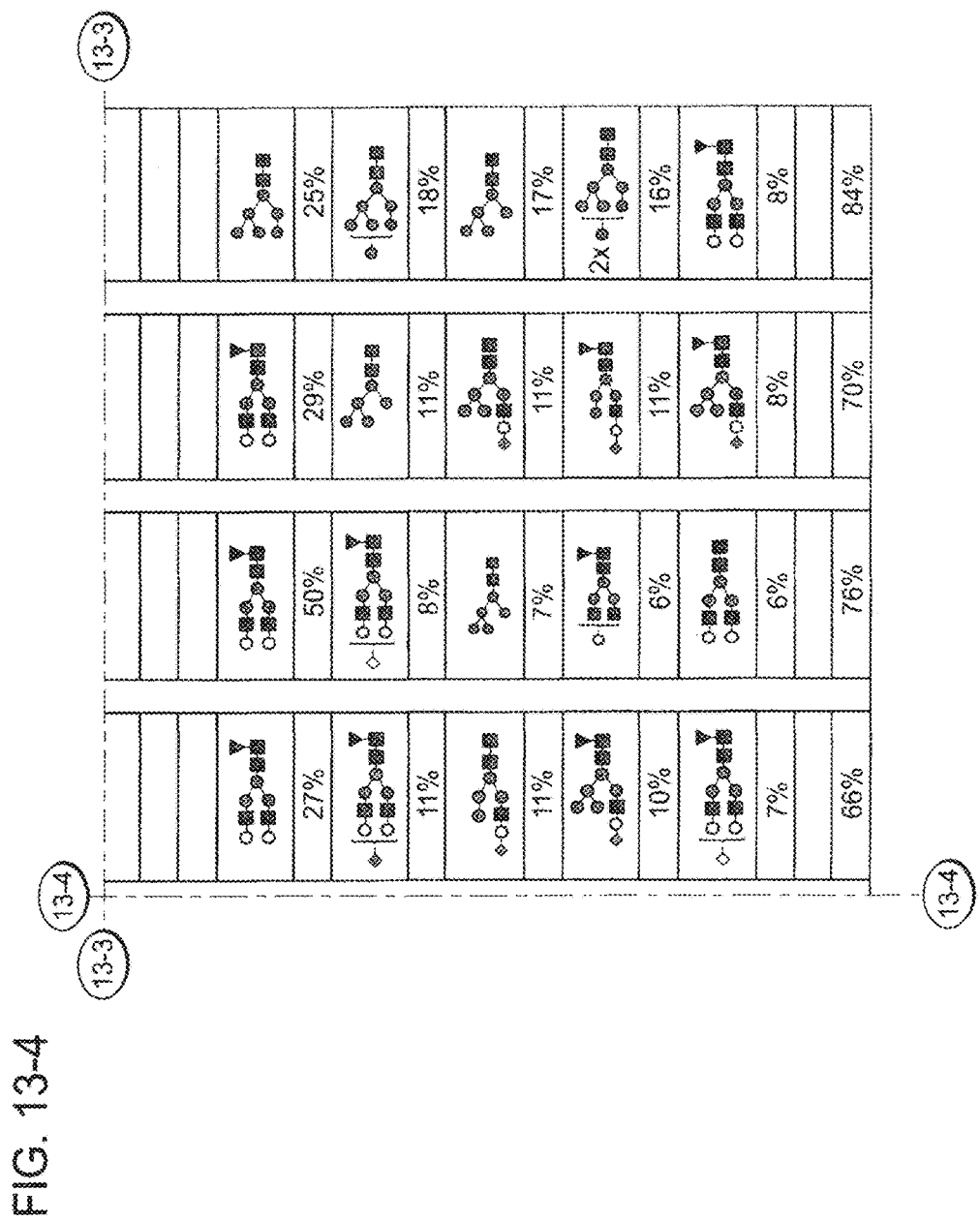

Adalimumab was transgenically produced in multiple different goats during natural lactation. The glycan profiles for transgenically produced adalimumab were examined. FIG. 13 provides a summary of percentages of different glycan forms present in populations of transgenically produced adalimumab antibody from the nine different goats listed in Table 3.

Figures 1, 2, 14:
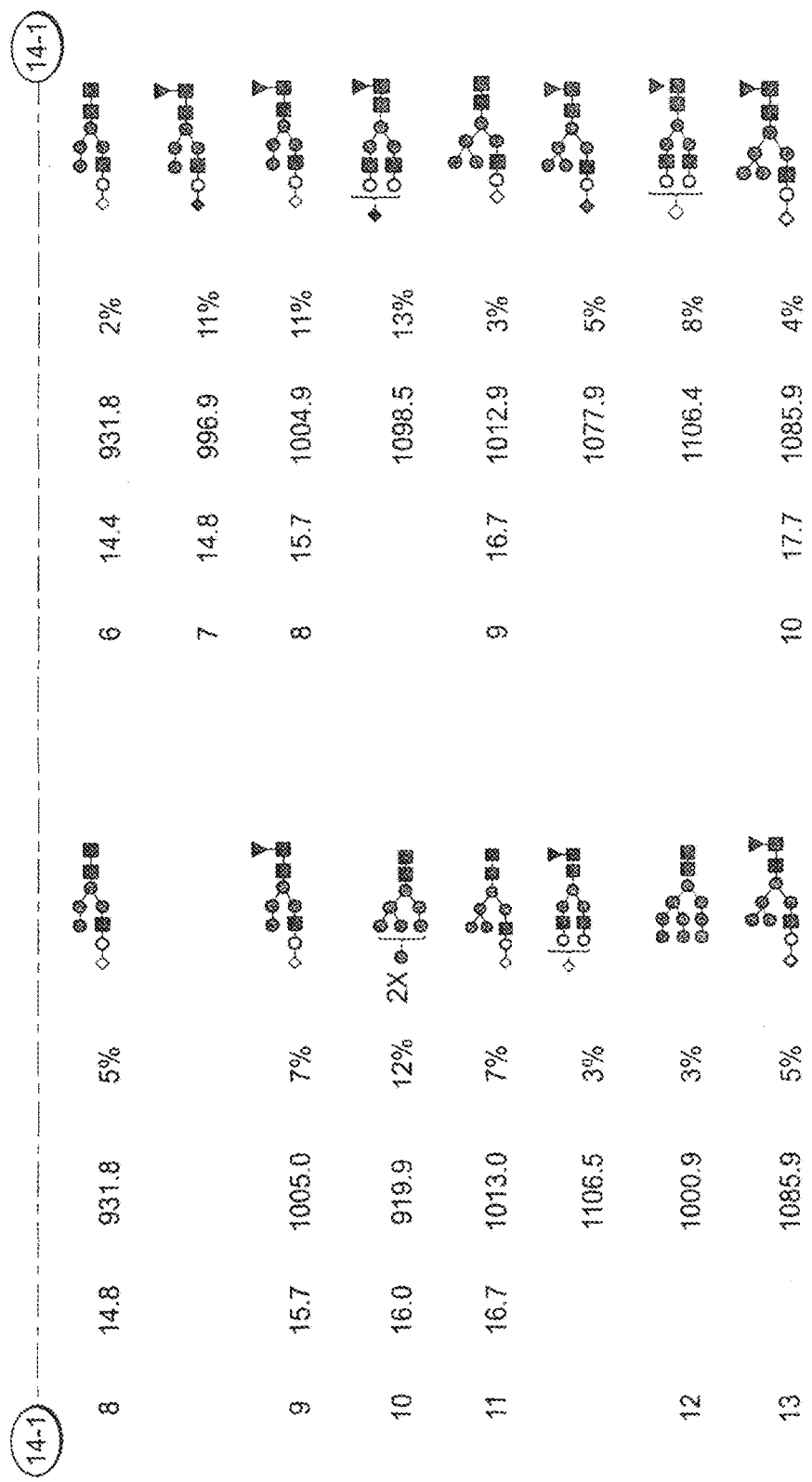
FIG. 14 shows a summary of the percentages of N-glycan oligosaccharides of populations of transgenically produced adalimumab antibodies from goat #10 and goat #1 during hormone induced lactation.

FIG. 14 shows a summary of the percentages of N-glycan oligosaccharides of populations of transgenically produced adalimumab antibodies from goat #10 and goat #1 during hormone induced lactation.

FIG. 15 shows a summary of N-glycan oligosaccharides of populations of transgenically produced adalimumab antibodies from eight different goats, goats #2-9. The data presented in FIG. 15 is summarized in Tables 4-11.

TABLE 4

N-glycan oligosaccharides isolated from adalimumab antibodies from goat # 2

|  | day 29 |
|---|---|
| mono-Gal (%) | 6.9 |
| bi-Gal (%) | 11.9 |
| mono-Gal + bi-Gal (%) | 18.8 |
| Gal* (%) | 16.9 |
| Fuc* (%) | 13.2 |
| Ratio Gal/Fuc | 1.28 |

TABLE 5

N-glycan oligosaccharides isolated from adalimumab antibodies from goat # 4

|  | day 29 |
|---|---|
| mono-Gal (%) | 23.2 |
| bi-Gal (%) | 11.3 |
| mono-Gal + bi-Gal (%) | 34.5 |
| Gal* (%) | 24.1 |
| Fuc* (%) | 30.4 |
| Ratio Gal/Fuc | 0.79 |

TABLE 6

N-glycan oligosaccharides isolated from adalimumab antibodies from goat # 7

|  | day 29 |
|---|---|
| mono-Gal (%) | 28.1 |
| bi-Gal (%) | 14.3 |
| mono-Gal + bi-Gal (%) | 42.4 |
| Gal* (%) | 30.7 |
| Fuc* (%) | 47 |
| Ratio Gal/Fuc | 0.65 |

TABLE 7

N-glycan oligosaccharides isolated from adalimumab antibodies from goat # 6

|  | day 29 |
|---|---|
| mono-Gal (%) | 31.9 |
| bi-Gal (%) | 14.3 |
| mono-Gal + bi-Gal (%) | 47 |
| Gal* (%) | 34.2 |
| Fuc* (%) | 49.6 |
| Ratio Gal/Fuc | 0.69 |

TABLE 8

N-glycan oligosaccharides isolated from adalimumab antibodies from goat # 3

|  | day 29 |
|---|---|
| mono-Gal (%) | 29.4 |
| bi-Gal (%) | 23.6 |
| mono-Gal + bi-Gal (%) | 53 |
| Gal* (%) | 46.1 |
| Fuc* (%) | 52.8 |
| Ratio Gal/Fuc | 0.87 |

TABLE 9

N-glycan oligosaccharides isolated from adalimumab antibodies from goat #9

|  | day 29 |
|---|---|
| mono-Gal (%) | 37.7 |
| bi-Gal (%) | 44 |
| mono-Gal + bi-Gal (%) | 81.7 |
| Gal* (%) | 81.7 |
| Fuc* (%) | 78.2 |
| Ratio Gal/Fuc | 1.04 |

TABLE 10

N-glycan oligosaccharides isolated from adalimumab antibodies from goat #5

|  | day 29 |
|---|---|
| mono-Gal (%) | 26.2 |
| bi-Gal (%) | 11.8 |
| mono-Gal + bi-Gal (%) | 38.0 |
| Gal* (%) | 27.6 |
| Fuc* (%) | 39.4 |
| Ratio Gal/Fuc | 0.70 |

TABLE 11

N-glycan oligosaccharides isolated from adalimumab antibodies from goat # 8

|  | day 29 |
|---|---|
| mono-Gal (%) | 18.6 |
| bi-Gal (%) | 65.4 |
| mono-Gal + bi-Gal (%) | 84 |
| Gal* (%) | 80.4 |
| Fuc* (%) | 74.0 |
| Ratio Gal/Fuc | 1.09 |

Example 4

Characterization of Transgenically Produced Adalimumab

Biological features of transgenically produced adalimumab from goat milk were compared to Adalimumab (Humira). Relative Kd, CD16-binding and FcRn binding were investigated. Furthermore, Complement Dependent Cytotoxicity (CDC) and neutralisation of TNF-α, mediated cellular cytotoxicity were evaluated on membrane TNF-α, transfected Jurkat cells.

Arbitrary Kd (concentration giving 50% of the plateau value) obtained by flux cytometry showed no difference (p=0.54) between Humira (0.09 µg/ml) and transgenically produced adalimumab (0.11 µg/ml). Transgenically produced adalimumab bound to CD16 receptor with an IC50 value of 25.7 µg/ml versus 56.67 µg/ml for Humira. Thus, binding of transgenically produced adalimumab to CD16 was 2.2 fold higher than that of Humira.

Transgenically produced adalimumab binding to FcRn was higher than that of Humira, despite having the same Fc portion. CDC activity showed an advantage with transgenically produced adalimumab compared to Humira antibody (196 vs 399 ng/ml). Transgenically produced adalimumab and Humira both neutralized similarly TNF-α induced L929 apoptosis (EC50=110 ng/ml and 98 ng/ml respectively).

Materials and Methods
 Reagents
  Anti TNF-α reagent:
   Antibody:
    Transgenically produced adalimumab
    Humira (Adalimumab, Abbott)
  Anti CD160: purification n° 829 10 049, used as negative control
  baby rabbit serum (Cederlane)
  Actinomycin D (Sigma)
  Human TNF-α (Miltenyi Biotec)
  Cell titer 96® aqueous One solution Cell Proliferation Assay (Promega)
 Cells
  Membrane TNF-α transfected Jurkat cells clone 2B3 were obtained by cloning (used for Relative Kd assay and CDC)
  Murine fibroblast L929 cells
Binding to Membrane TNF-α and Relative Kd Determination $2 \times 10^5$ TNF-α transfected Jurkat cells were incubated with 100 µl of anti-TNF Alexa-488 coupled antibodies at different concentrations (0 to 100 µl/ml, final concentration) at 4° C. for 30 minutes. After washing, a goat anti-human Fc gamma coupled to phycoerythrin (100 µl of a dilution of 1:100) was added at 4° C. for 30 minutes. The cells were washed and mean of fluorescence intensity (MFI) studied by flow cytometry. Arbitrary Kd was calculated using PRISM software.

Binding to CD16

Binding to CD16 was studied by a competitive assay using the mouse phycoerythrin-labelled anti-CD16 3G8 (3G8-PE) and NK cells. Briefly, NK cells were isolated from peripheral blood mononuclear cells (PBMC) using the NK Cell Isolation Kit from Myltenyi then incubated with variable concentrations (0 to 83 µg/ml) of the tested antibodies simultaneously with the mouse anti-CD16 mAb 3G8-PE used at a fixed concentration. After washing, the binding of 3G8-PE to CD16 expressed by NK cell was evaluated by flow cytometry. The mean fluorescence values (MFI) observed are expressed in percent, 100% being the value obtained with the 3G8-PE alone and 0% the value in the absence of the 3G8-PE. IC50 values (antibody concentration required to induce 50% inhibition of 3G8 binding) were calculated using PRISM software.

Binding to FcRn

Binding to FcRn was studied by a competitive assay using the anti-CD20 Rituxan labeled by Alexa 488 (RTX-Alexa) and transfected FcRn Jurkat cells. Briefly, transfected FcRn Jurkat cells were incubated with variable concentrations (0 to 1000 µg/ml) of the tested mAbs simultaneously with a fixed concentration RTX-Alexa (50 µg/ml) at pH=6. After washing at pH=6, binding of RTX-Alexa to FcRn expressed by transfected FcRn Jurkat cells was evaluated by flow cytometry. The mean fluorescence values (MFI) observed are expressed in percent, 100% being the value obtained with the RTX-Alexa alone and 0% the value in the absence of the RTX-Alexa. IC50 values (antibody concentration required to induce 50% of inhibition of RTX-Alexa binding) were calculated using PRISM software.

CDC

Membrane TNF-α transfected Jurkat cells (mbTNF-α Jurkat) were incubated with increasing concentrations of anti-TNF antibodies (0 to 5000 ng/ml) in the presence of baby rabbit serum as a source of complement (dilution to ⅒). After 2 hours of incubation at 37° C., the quantity of LDH released in the supernatant by the lysed target cells was measured (Roche Applied Sciences Cytotoxicity Detection Kit). The percent lysis corresponding to the complement-dependent cytotoxicity (CDC) mediated by the studied antibodies was calculated according to the following formula: % lysis=(ER−SA), where ER=effective response (LDH release), SA=spontaneous activity obtained when target cell were incubated in the presence of complement but without antibody. Percent lysis is expressed as a function of antibody concentrations. Emax (percentage of maximum lysis) and EC50 (quantity of antibody that induces 50% of maximum lysis) were calculated using PRISM software.

Neutralization of sTNF-α

Neutralization of human TNF was assessed in the murine fibroblast L929 bioassay using a range of concentrations of the anti-TNFs and a fixed concentration of TNF (100 pg/mL). Briefly, TNF-α (20 ng/ml) pretreated with serial dilutions of tested antibodies (0-1000 ng/ml) was incubated for 18 h with L929 cells in the presence of actinomycin D (2 µg/ml) at 37° C. for 16 h. Then 20 µl/well of Cell titer 96® aqueous One solution Cell Proliferation Assay (MTS) was added for a further 1 h to determine the number of surviving cells by colorimetric assay. The plates were read at 490 nm and results (OD) were expressed as a function of antibody concentrations. The neutralizing titer expressed as the reciprocal of the antibody concentration that neutralizes 50% of TNF-α activity was calculated using PRISM software.

Abbreviations

TNF-α: Tumor Necrosis Factor alpha
CDC: Complement Dependent Cytotoxicity
LDH: Lactate dehydrogenase
MFI: Mean of Fluorescence Intensity
SA: Spontaneous Activity
SR: Spontaneous release Results Antigen-binding on Cell and Relative Kd Determination The mean of three assays is presented in FIG. 16 and the corresponding data are presented in Table 13. Binding of anti-TNF antibodies to membrane TNF-α transfected Jurkat cells clone 2B3 is expressed as the mean of fluorescence intensity (MFI) for each antibody concentration tested (0-10 µg/ml). Arbitrary Kd as described below does not represent the real affinity value (nM), but gives an order of comparable magnitude for the affinity of the studied antibodies.

Results in Table 12a show that the Bmax values (plateau) and arbitrary Kd (concentration giving 50% of the plateau value) are similar for transgenically produced adalimumab (Bmax: MFI=12.46; Kd=0.11 µg/ml) and Humira (Bmax: MFI=10.72; Kd=0.09 µg/ml) as shown with the statistical analysis (p=0.54) performed with individual EC50 values (Table 12b).

TABLE 12a

Figure 16:
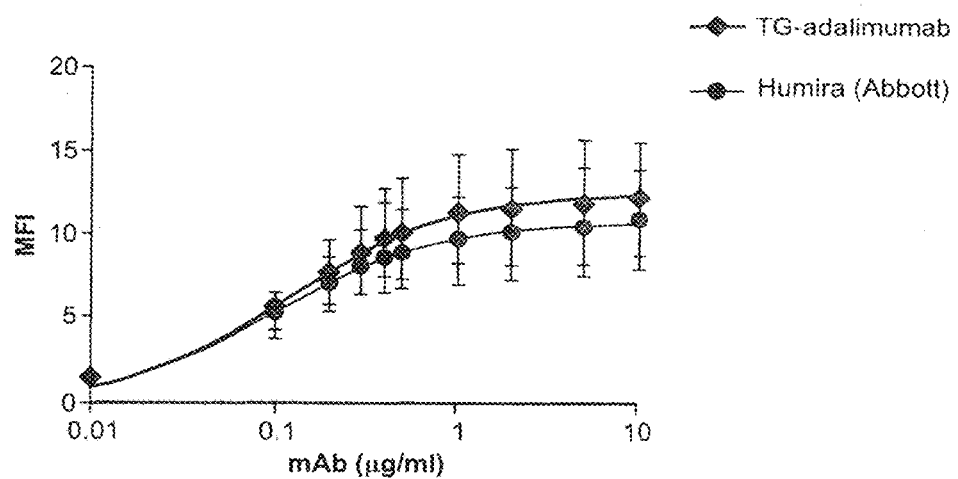
FIG. 16 shows antigenic recognition of transgenically produced adalimumab ("TG-adalimumab") and Humira antibodies on membrane TNF-α transfected Jurkat cells clone 2B3. The results shown are expressed as MFI and derived from an average of 3 experiments. Mean+/−SEM.

Bmax, relative Kd values and original data corresponding to FIG. 16

|  | Transgenically produced adalimumab | Humira (Abbott) | Anti CD160 |
|---|---|---|---|
| Bmax (MFI) | 12.46 | 10.72 | na |
| Kd (µg/ml) | 0.1194 | 0.09874 | na |

TABLE 12b

Individual EC50 values and P value (student test)

|  | Transgenically produced adalimumab | Humira (Abbott) |
|---|---|---|
| EC50-1 | 1 | 5.57142857 |
| EC50-2 | 1 | 0.09640719 |
| EC50-3 | 1 | 0.81034483 |
| p student |  | 0.536862306 |

TABLE 13

Data corresponding to FIG. 16

| m Ab (µg/ml) | Transgenically produced adalimumab | | | Humira (Abbott) | | |
|---|---|---|---|---|---|---|
| 0 | 0.502 | 1.36 | 0.816 | 0.502 | 1.36 | 0.816 |
| 0.01 | 0.81 | 1.81 | 1.69 | 0.87 | 1.69 | 1.63 |
| 0.1 | 2.50 | 5.80 | 6.99 | 3.34 | 5.66 | 6.57 |
| 0.2 | 3.33 | 9.45 | 9.86 | 4.30 | 8.74 | 8.41 |
| 0.3 | 3.84 | 12.90 | 10.30 | 4.66 | 11.50 | 8.76 |
| 0.4 | 5.23 | 14.50 | 10.60 | 4.65 | 11.80 | 9.19 |
| 0.5 | 5.14 | 15.50 | 10.40 | 4.86 | 13.10 | 9.15 |
| 1 | 6.05 | 17.20 | 11.20 | 5.10 | 14.10 | 9.32 |
| 2 | 5.80 | 17.80 | 11.30 | 5.40 | 15.00 | 9.76 |
| 5 | 5.56 | 18.40 | 11.60 | 5.78 | 15.70 | 9.85 |
| 10 | 6.30 | 18.00 | 12.10 | 6.33 | 16.60 | 9.89 |

Binding to CD16, Competition of 3G8 Antibody

IC50 values, indicated in Table 14, represent the antibody concentration required to induce 50% of inhibition of 3G8 binding on CD16 receptor expressed by NK cells. Transgenically produced adalimumab ("TG-Humira"), and Humira antibody bind to CD16 receptor with an IC50 value of 25.7 µg/ml and 56.7 µg/ml respectively. Thus, binding of transgenically produced adalimumab to CD16 is almost 2 fold higher than that of Humira.

TABLE 14

Figure 17:
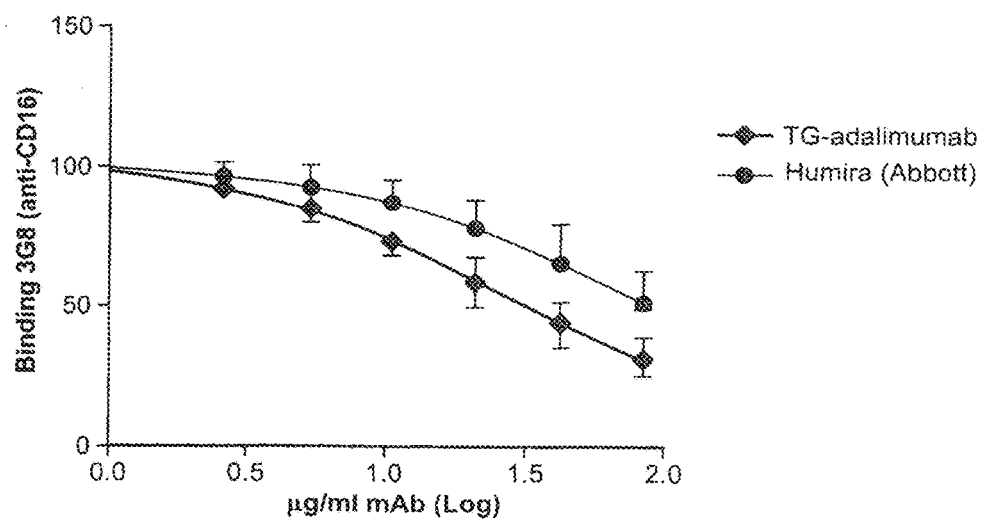
FIG. 17 shows binding of anti-TNF-α antibodies on CD16 expressed by NK cells in a competition assay. The mean fluorescence values (MFI) observed are expressed as the percent binding, where 100% is an arbitrary value corresponding to maximum 3G8 binding observed without the tested antibodies and 0% corresponds to the MFI in the absence of the antibody 3G8. Mean of 3 experiments+/−SEM.

IC50 (antibody concentration required to induce 50% of inhibition of 3G8 binding), corresponding to FIG. 17, after modeling of the curve by the PRISM software.

|  | Humira (Abbott) | Transgenically produced adalimumab |
|---|---|---|
| IC50 (µg/ml) | 57 | 26 |

TABLE 15

Data corresponding to FIG. 17

| Log C µg/ml | Humira (Abbott) | | | Transgenically produced adalimumab | | |
|---|---|---|---|---|---|---|
| 0.01 | 100 | 100 | 100 | 100 | 100 | 100 |
| 0.11 | 96.95 | 89.81 | 96.44 | 96.06 | 95.59 | 101.36 |
| 0.41 | 99.24 | 89.81 | 102.59 | 94.49 | 88.97 | 98.98 |
| 0.72 | 97.71 | 85.35 | 102.27 | 88.19 | 75.74 | 93.54 |
| 1.02 | 90.08 | 71.34 | 99.68 | 78.35 | 57.06 | 82.65 |
| 1.32 | 83.21 | 55.92 | 91.91 | 62.76 | 41.03 | 71.43 |
| 1.62 | 71.3 | 39.94 | 83.5 | 45.67 | 28.31 | 56.12 |
| 1.92 | 56.95 | 28.22 | 67.96 | 34.65 | 19.34 | 42.52 |

Binding to FcRn

Binding of anti-TNF-α antibodies to FcRn expressed by FcRn-transfected Jurkat cells was tested in a competition assay with Alexa 488 coupled-Rituximab antibody. Results showed in FIG. 18 (corresponding data Table 17) indicate that all the tested antibodies bound to the FcRn receptor. Binding of transgenically produced adalimumab to FcRn appeared higher than that of Humira.

TABLE 16

Figure 18:
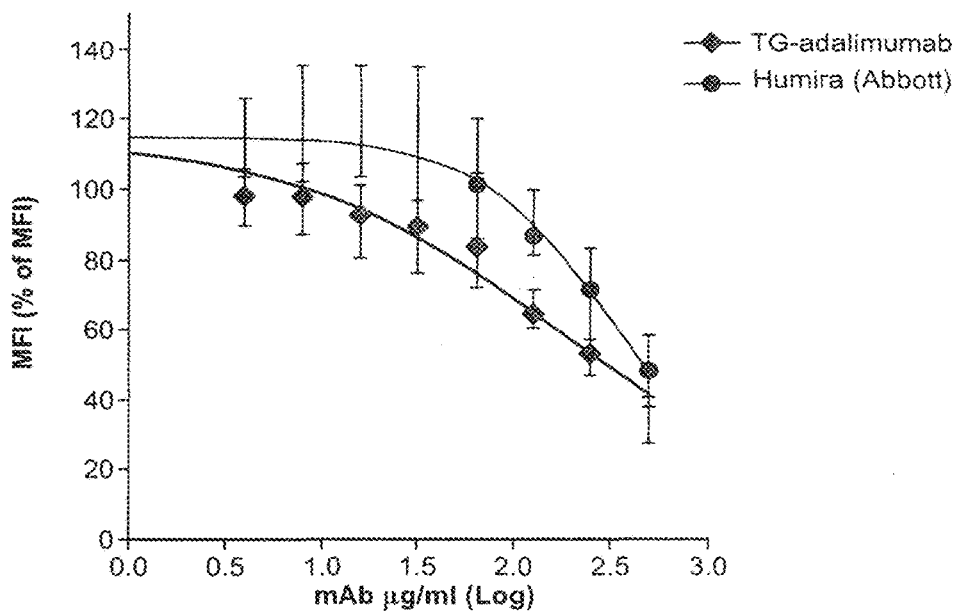
FIG. 18 shows binding of anti-TNF-α antibodies on FcRn expressed by FcRn-transfected Jurkat cells in a competition assay with Alexa 488 coupled-Rituximab antibody. The mean fluorescence values (MFI) observed are expressed as the percent binding (100% is an arbitrary value corresponding to maximum Rituximab-A488 binding alone), as a function of attested antibody concentration. Mean of 3 experiments+/−SEM.

$IC_{50}$ (antibody concentration required to induce 50% of inhibition of Rituximab binding), corresponding to FIG. 18, after modeling of the curve by the PRISM software.

| | RITUXAN | Transgenically produced adalimumab | Humira (Abbott) |
|---|---|---|---|
| IC50 (µg/ml) | 233 | 195 | 366 |

TABLE 17

Data corresponding to FIG. 18

| Ac ng/ml (Log) | Transgenically produced adalimumab | | | Humira (Abbott) | | |
|---|---|---|---|---|---|---|
| −1 | 96.6 | 93.75 | 92.4 | 107.4 | 101.25 | 114 |
| 0.602 | 112.7 | 84.75 | 96 | 118.3 | 86.25 | 132 |
| 0.903 | 117.8 | 81 | 94.7 | 135.5 | 85.5 | 138.2 |
| 1.204 | 113.2 | 73.65 | 90.2 | 125.4 | 85.5 | 144 |
| 1.505 | 111.1 | 66.675 | 89.5 | 123.6 | 78.75 | 144.3 |
| 1.806 | 99.9 | 64.125 | 83.7 | 114.1 | 65.625 | 125.3 |
| 2.097 | 94.3 | 51.825 | 72.8 | 95 | 58.425 | 104 |
| 2.398 | 67.4 | 33.9 | 53.1 | 75 | 45.525 | 89.2 |
| 2.699 | 39.8 | 22.875 | 35.4 | 50.6 | 32.925 | 64.1 |

CDC Activity

Figure 19:
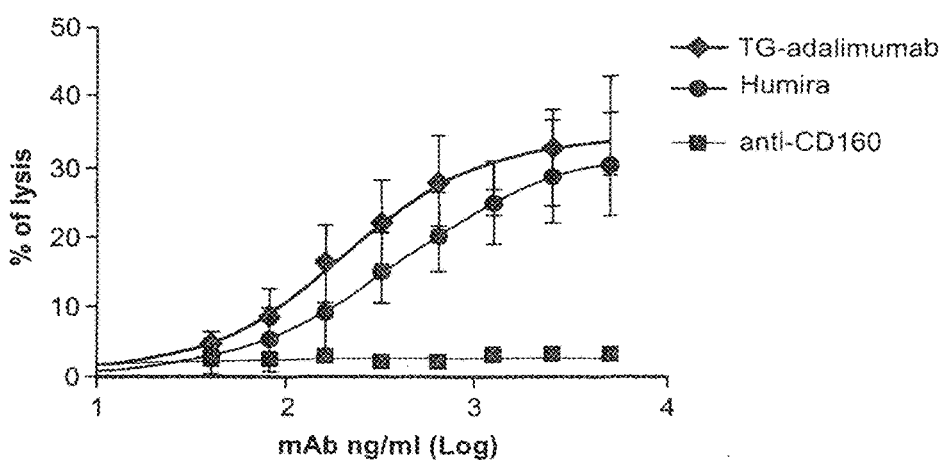
FIG. 19 shows CDC activity of the anti TNF-α antibodies on membrane TNF-α transfected Jurkat cells clone 2B3 (mean of 4 assays). Results are expressed as percent of lysis of mbTNF-α Jurkat cells as a function of antibody concentration. Mean+/−SEM.

The mean of two assays is presented in FIG. 19 and the corresponding data are shown in Table 18. The CDC activity is expressed as the percent of lysis for each antibody concentration tested (0-5000 ng/ml). FIG. 19 shows that transgenically produced adalimumab (TG-Humira; maximal lysis: 34%) and Humira (maximal lysis: 33%) antibodies induce a comparable lysis of mbTNF-α Jurkat by CDC activity). Analysis of EC50 values in this system (Table 19) showed a small advantage of transgenically produced adalimumab compared to benchmark Humira antibody (195.8 vs 399.3 ng/ml)

TABLE 18

Original data from each of the three experiments performed with the antibodies tested and used for designing FIG. 19 with PRISM software.

| Ac ng/ml (Log) | Transgenically produced adalimumab | | | | Humira Abbott) | | | |
|---|---|---|---|---|---|---|---|---|
| −1 | 0 | 0 | 0 | 0 | 0 | 0 | 0 | 0 |
| 1.6 | 0 | 6 | 0 | 10 | 0 | 2 | 0 | 10 |
| 1.9 | 0 | 10 | 0 | 21 | 0 | 2 | 0 | 19 |
| 2.2 | 6 | 20 | 9 | 30 | 1 | 10 | 3 | 23 |
| 2.5 | 11 | 30 | 13 | 35 | 6 | 23 | 8 | 24 |
| 2.8 | 18 | 43 | 16 | 35 | 13 | 25 | 11 | 31 |
| 3.1 | 19 | 37 | 20 | 38 | 14 | 30 | 16 | 39 |
| 3.4 | 23 | 42 | 17 | 44 | 13 | 38 | 21 | 45 |
| 3.7 | 25 | 48 | 23 | 48 | 16 | 36 | 22 | 48 |

TABLE 19

Emax (maximal lysis) and EC50 (antibody concentration required to induce 50% of maximal lysis), corresponding to FIG. 19, after sigmoid modeling of the curve by the PRISM software.

| | Transgenically produced adalimumab | Humira (Abbott) | anti-CD160 |
|---|---|---|---|
| Emax (% of lysis) | 34.31 | 33.14 | 2.839 |
| EC50 (ng/ml) | 195.8 | 399.3 | na |

Neutralization Activity of Anti-TNF Antibodies

Figure 20:
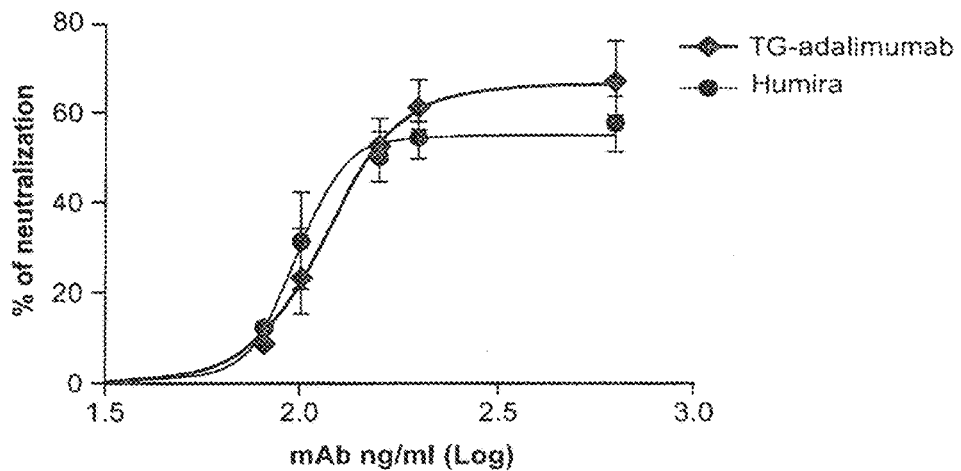
FIG. 20 shows neutralization of TNF-α-mediated cytotoxicity in L929 cells by anti-TNF-α, antibodies. Results are expressed as percent of neutralization as a function of antibody concentration. Mean of 4 assays+/−SEM.

As shown in FIG. 20, TNF-α-mediated cytotoxicity in L929 cells treated with 20 ng/ml of human TNF-α was effectively neutralized by both transgenically produced adalimumab (TG-humira) and Humira mAbs in a comparable dose dependent manner. The 50% values, corresponding to the antibody concentration required to achieve 50% of the Humira plateau value, were 97.7 ng/ml for Humira and 109.7 ng/ml for transgenically produced adalimumab.

TABLE 20

Maximal neutralization and 50% value (antibody concentration required to achieve 50% of the Humira plateau value), corresponding to FIG. 20, after sigmoid modeling of the curve by the PRISM software.

| | Transgenically produced adalimumab | Humira (Abbott) |
|---|---|---|
| % neutralization max | 66.2 | 54.6 |
| 50% of Humira neutralization (ng/ml) | 109.65 | 97.72 |

TABLE 21

Original data from each of the three experiments performed with the antibodies tested and used for designing FIG. 20 with PRISM software.
% TNF neutralization

| Ac ng/ml (Log) | Transgenically produced adalimumab | | | | Humira (Abbott) | | | |
|---|---|---|---|---|---|---|---|---|
| 1 | 0 | 2.17 | 2.58 | 0 | 0 | 1.24 | 0.47 | 0 |
| 1.4 | 0 | 0.71 | 1.84 | 0 | 0.25 | 0.73 | 0.7 | 0 |
| 1.7 | 0 | 1.56 | 2.01 | 0 | 0.17 | 0.45 | 1.22 | 5.71 |
| 1.9 | 0.17 | 7.08 | 5.87 | 19.93 | 0.88 | 5.7 | 11.69 | 19.25 |
| 2 | 4.35 | 32.77 | 13.15 | 47.85 | 6.98 | 21.39 | 42.07 | 55.18 |
| 2.2 | 31.78 | 63.85 | 54.7 | 56.47 | 42.01 | 58.88 | 40.68 | 59.71 |
| 2.3 | 49.64 | 76.17 | 63.88 | 55.87 | 52.04 | 59.01 | 43.6 | 60.98 |
| 2.8 | 54.62 | 88.3 | 46.78 | 75.94 | 60.47 | 68.4 | 39.53 | 60.68 |

Discussion

Neutralisation of TNF induced L929 apoptosis was comparable between transgenically produced adalimumab and Humira (Abott). CDC activity, binding to CD16 and FcRn was improved and increased CDC and CD16 binding were observed for transgenically produced adalimumab.

Example 5

ADCC Activity of Transgenically Produced Adalimumab

Figure 21:
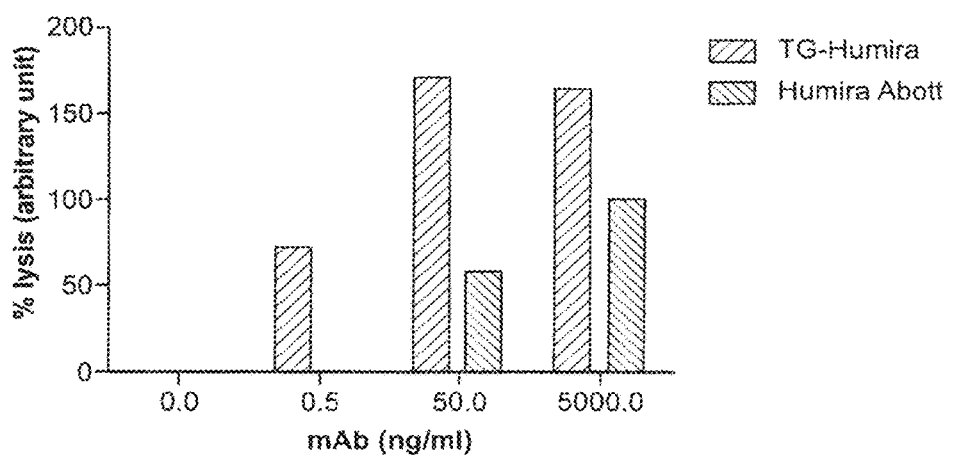
FIG. 21 shows percent lysis (in arbitrary units) mediated by transgenically produced adalimumab compared to Humira.

ADCC activity of transgenically produced adalimumab was compared to ADCC activity of Humira. FIG. 21 shows that transgenically produced adalimumab demonstrated higher ADCC activity than Humira at three different concentrations: 0.5 ng/ml, 50 ng/ml and 5000 ng/ml.

Antibodies:
 Humira (Abbott)
 Transgenically produced adalimumab
Cells:
 mTNF-transfected Jurkat cells (clone 2F8)
 NK effector cells isolated from a healthy donors NK effector cells were isolated from the peripheral blood samples from healthy donors using a negative depletion kit (Miltenyi Biotec). Jurkat cells transfected with mTNF were plated in 96 well plates and incubated at 4° C. with increasing concentrations of anti-TNF antibodies (0.5; 50 and 5000 ng/ml). After 2 hours, the isolated NK cells were added and incubated for another 4 hours at 37° C. Lysis of target cells induced by the tested anti-TNF antibodies was measured chromogenically by quantifying the intracellular enzyme lactate dehydrogenase (LDH) released into the supernatant by the lysed target cells (Roche). The percent lysis was calculated according to the following formula:

% lysis=[(ER−SR)/(100−SR)]−[(NC−SR)/(100−SR)]

Where ER and SR represent experimental and spontaneous LDH release, respectively, and NC represents natural cytotoxicity. Final results are expressed in arbitrary units with 100% as the value obtained with Humira (Abbott) at a concentration of 5000 ng/ml. As presented in FIG. 21 transgenically produced adalimumab induced more ADCC than Humira (Abbott).

Example 6

Figure 22:
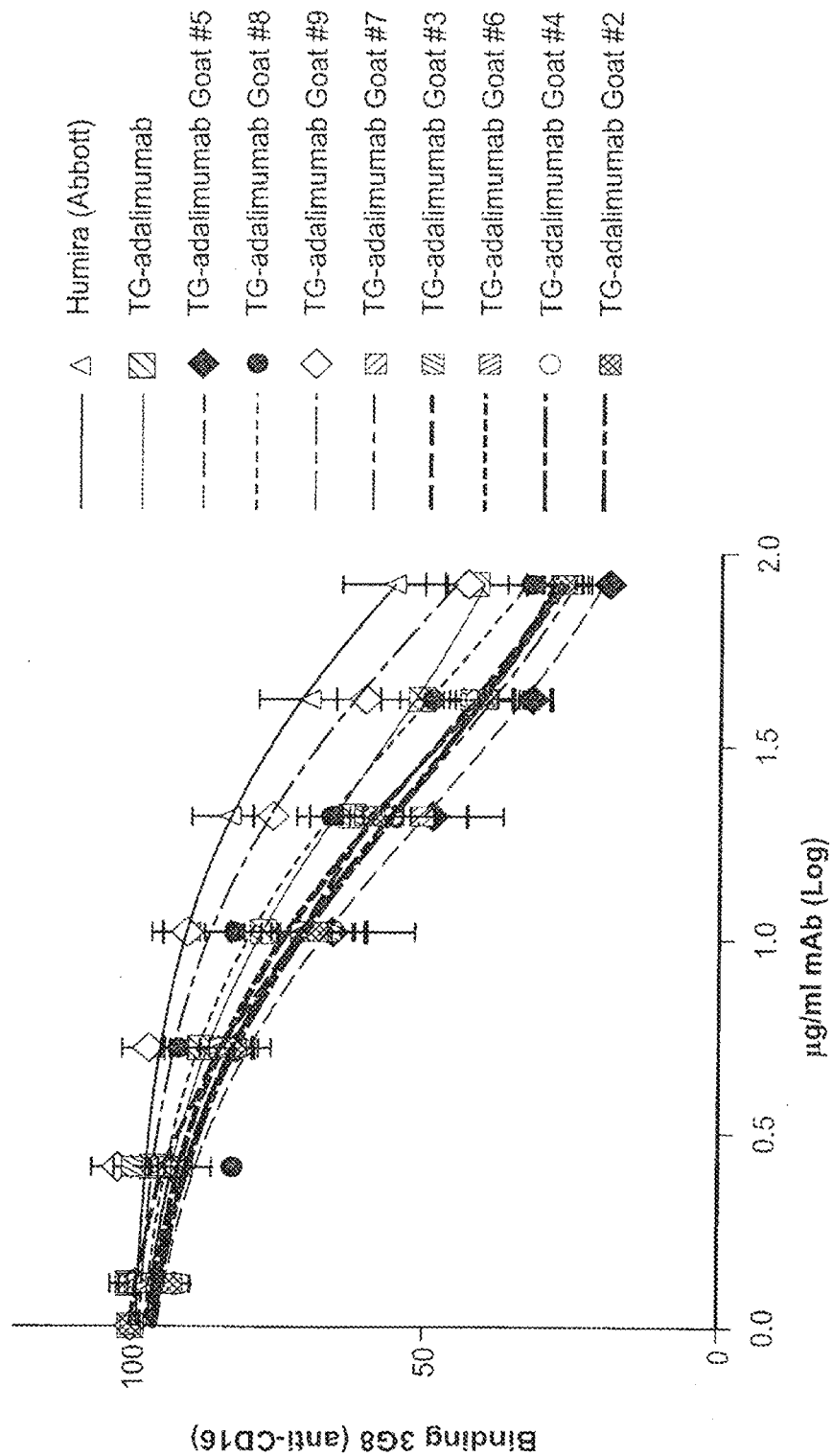
FIG. 22 presents an inhibition curve showing CD16 binding activity of transgenically produced adalimumab from nine different goats compared to Humira.
Figure 23:
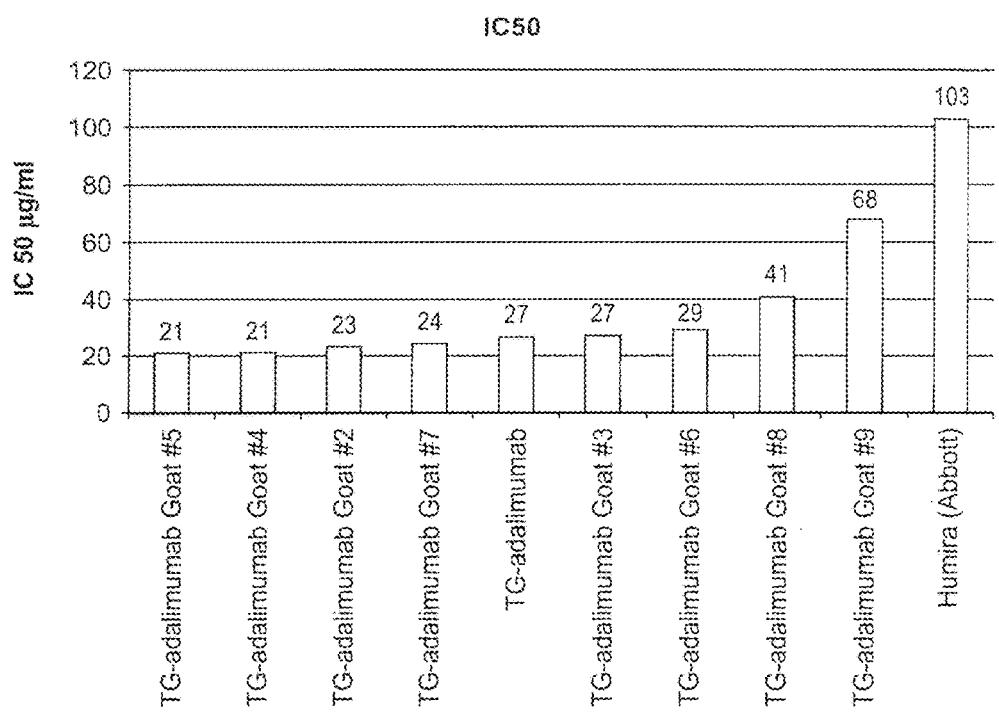
FIG. 23 presents IC50 values associated with CD16 binding activity of transgenically produced adalimumab from nine different goats and Humira as assessed by a competitive assay using NK cells.

Assessment of CD16-binding and CDC Activity of Transgenically Produced Adalimumab CD16 binding activity of transgenically produced adalimumab was measured by a competitive assay using NK cells and compared to Humira. FIG. 22 presents an inhibition curve showing that transgenically produced adalimumab from nine different goats all bound to CD16 to a greater extent than Humira in NK cells. FIG. 23 presents IC50 values from CD16 competitive binding assays. IC50 values were 1.5-5×lower for transgenically produced adalimumab than for Humira.

Figure 24:
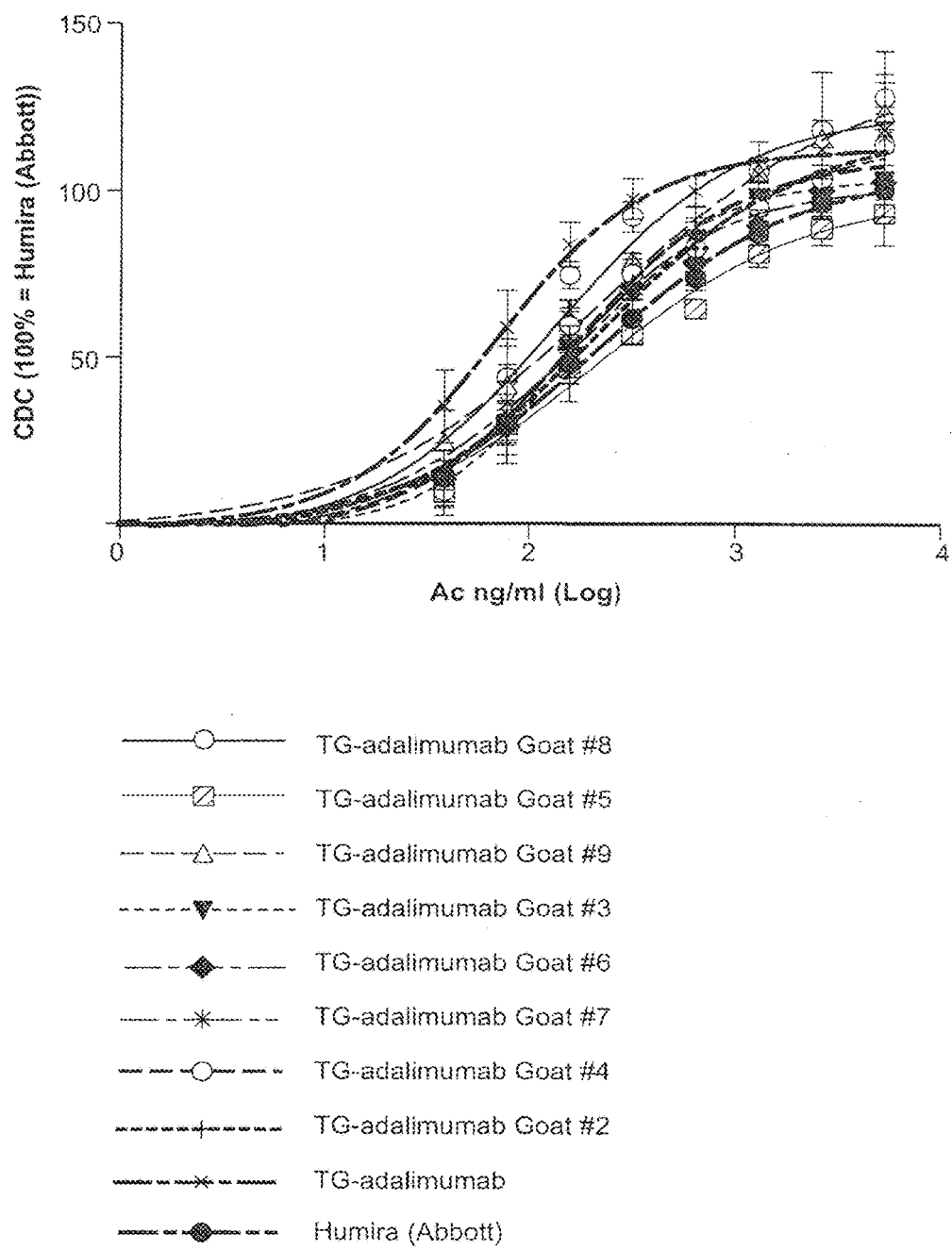
FIG. 24 shows CDC activity of transgenically produced adalimumab from nine different goats compared to Humira.
Figure 25:
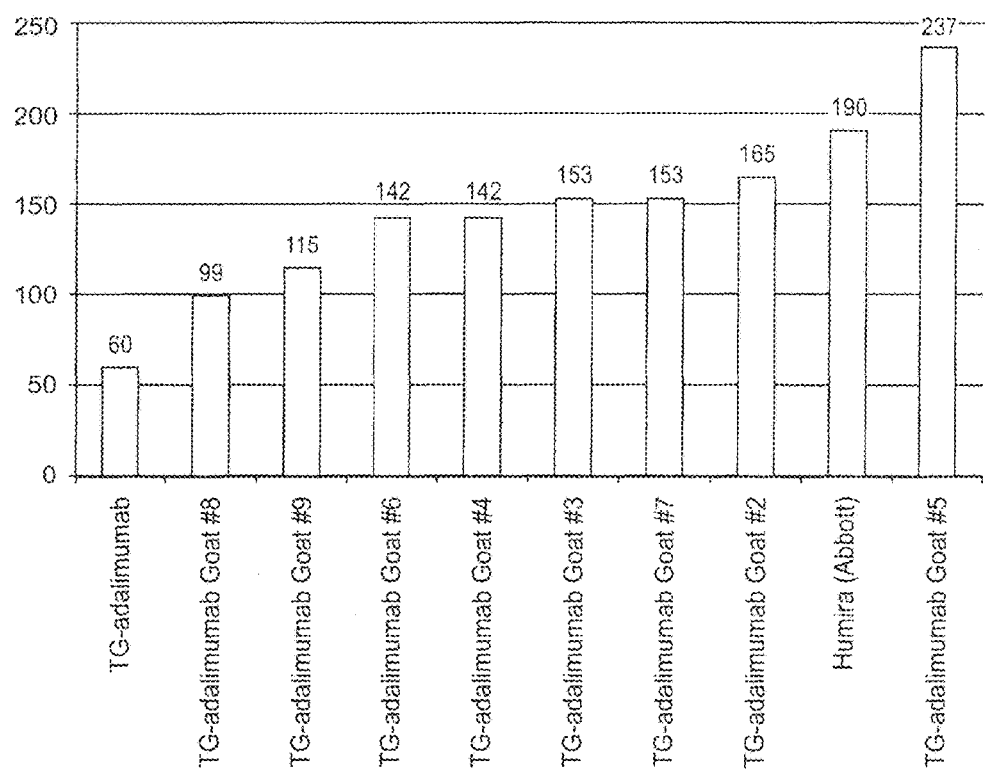
FIG. 25 shows EC50 values (ng/ml) associated with CDC activity of transgenically produced adalimumab from nine different goats compared to Humira.

CDC activity of transgenically produced adalimumab was compared to that of Humira. FIG. 24 presents a dose response curve showing that transgenically produced adalimumab from eight out of nine goats tested had greater CDC activity than Humira. FIG. 25 presents the EC50 values in ng/ml for the CDC activity assay.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A composition, comprising:
a population of antibodies,
wherein the antibodies in the population of antibodies are anti-TNF-alpha antibodies produced in mammary gland epithelial cells of a transgenic non-human mammal;
wherein the level of galactosylation of the antibodies in the population of antibodies comprises at least 5% mono-galactosylated N-glycans or at least 10% bi-galactosylated N-glycans;
wherein the level of fucosylation of the antibodies in the population of antibodies is at least 30%; and
wherein the antibodies in the population of antibodies comprise a heavy chain comprising SEQ ID NO: 1 and a light chain comprising SEQ ID NO: 2.

2. The composition of claim 1, wherein at least 25% of the antibodies in the population comprise mono-galactosylated N-glycans and at least 35% of the antibodies in the population comprise bi-galactosylated N-glycans.

3. The composition of any one of claim 1, wherein the level of fucosylation of the antibodies in the population is at least 40%.

4. The composition of claim 1 wherein the level of fucosylation of the antibodies in the population is 30.4%-78.2%.

5. The composition of claim 1, wherein the level of fucosylation of the antibodies in the population is at least 50%.

6. The composition of claim 1, wherein the level of fucosylation of the antibodies in the population is at least 60%.

7. The composition of claim 1, wherein the level of fucosylation of the antibodies in the population is at least 70%.

8. The composition of claim 1, wherein the level of fucosylation of the antibodies in the population is at least 80%.

9. The composition of claim 1, wherein the level of fucosylation of the antibodies in the population is at least 90%.

10. The composition of any one of claim 1, wherein the ratio of the level of galactosylation of the antibodies in the population to the level of fucosylation of the antibodies in the population is between 1.0 and 1.4.

11. The composition of any one of claim 1, wherein the population of antibodies has an increased level of complement dependent cytotoxicity (CDC) activity when compared to a population of antibodies not produced in mammary gland epithelial cells.

12. The composition of any one of claim 1, wherein the population of antibodies has an increased level of antibody-dependent cellular cytotoxicity (ADCC) activity when compared to a population of antibodies not produced in mammary gland epithelial cells.

13. The composition of claim 1, wherein the transgenic non-human mammal is a goat, sheep, camel, cow, pig, rabbit, rat, mouse or llama.

14. The composition of claim 13, wherein the transgenic non-human mammal is a goat.

15. A composition, comprising:
a population of antibodies,
wherein the antibodies in the population of antibodies are anti-TNF-alpha antibodies produced in mammary gland epithelial cells of a transgenic non-human mammal;
wherein at least 30% of the antibodies in the population of antibodies contain at least one oligomannose;
wherein the level of fucosylation of the antibodies in the population of antibodies is at least 30%; and
wherein the antibodies in the population of antibodies comprise a heavy chain comprising SEQ ID NO: 1 and a light chain comprising SEQ ID NO: 2.

16. The composition of claim 15, wherein the antibodies in the population of antibodies exhibit a high mannose glycosylation pattern.

17. The composition of claim 16, wherein at least one chain of the antibodies in the population of antibodies contains an oligomannose and is non-fucosylated.

18. The composition of claim 15, wherein the major carbohydrate of the antibodies in the population of antibodies is non-fucosylated.

19. The composition of claim 15, wherein the transgenic non-human mammal is a goat, sheep, camel, cow, pig, rabbit, rat, mouse or llama.

20. The composition of claim 19, wherein the transgenic non-human mammal is a goat.

* * * * *

UNITED STATES PATENT AND TRADEMARK OFFICE
CERTIFICATE OF CORRECTION

PATENT NO. : 10,174,110 B2
APPLICATION NO. : 14/767117
DATED : January 8, 2019
INVENTOR(S) : Harry M. Meade et al.

Page 1 of 1

It is certified that error appears in the above-identified patent and that said Letters Patent is hereby corrected as shown below:

In the Claims

Claim 3, Column 55, Line 21 should read:
"The composition of claim 1,"

Claim 4, Column 55, Line 24 should read:
"The composition of claim 1,"

Claim 10, Column 55, Line 42 should read:
"The composition of claim 1,"

Claim 11, Column 56, Line 1 should read:
"The composition of claim 1,"

Claim 12, Column 56, Line 6 should read:
"The composition of claim 1,"

Signed and Sealed this
Nineteenth Day of March, 2019

Andrei Iancu
*Director of the United States Patent and Trademark Office*

SEQUENCE LISTING

```
<160> NUMBER OF SEQ ID NOS: 4

<210> SEQ ID NO 1
<211> LENGTH: 470
<212> TYPE: PRT
<213> ORGANISM: Homo sapiens
```

<400> SEQUENCE: 1

```
Met Glu Phe Gly Leu Ser Trp Leu Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
65                  70                  75                  80

Asp Ser Val Glu Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Lys Val Ser Tyr Leu Ser Thr Ala Ser Ser Leu Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415
```

Thr Pro Pro Val Leu Asp Ser Asp Gly Ser Phe Phe Leu Tyr Ser Lys
          420             425                 430

Leu Thr Val Asp Lys Ser Arg Trp Gln Gln Gly Asn Val Phe Ser Cys
              435                 440                 445

Ser Val Met His Glu Ala Leu His Asn His Tyr Thr Gln Lys Ser Leu
    450                 455                 460

Ser Leu Ser Pro Gly Lys
465             470

<210> SEQ ID NO 2
<211> LENGTH: 236
<212> TYPE: PRT
<213> ORGANISM: homo sapiens

<400> SEQUENCE: 2

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Tyr Leu Ala Trp Tyr Gln Gln Lys Pro Gly Lys
    50                  55                  60

Ala Pro Lys Leu Leu Ile Tyr Ala Ala Ser Thr Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Val Ala Thr Tyr Tyr Cys Gln Arg
            100                 105                 110

Tyr Asn Arg Ala Pro Tyr Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 3
<211> LENGTH: 1416
<212> TYPE: DNA
<213> ORGANISM: homo sapiens

<400> SEQUENCE: 3
atggaattcg gcctgagctg gctgttcctg gtggccatcc tgaagggcgt gcagtgcgag      60
gtgcagctgg tggagtctgg cggaggactg gtgcagcccg gcagaagcct gagactgagc     120
tgcgccgcca gcggcttcac cttcgacgac tacgccatgc actgggtccg ccaggcccct     180

```
ggaaagggcc tggaatgggt gtccgccatc acctggaaca gcggccacat cgactacgcc      240
gacagcgtgg agggcaggtt caccatcagc agggacaacg ccaagaacag cctgtacctg      300
cagatgaaca gcctgagggc cgaggacacc gccgtgtact actgcgccaa ggtgtcctac      360
ctgagcaccg ccagcagcct ggattactgg ggccagggca ccctggtgac cgtgtccagc      420
gccagcacca agggcctag cgtgttccct ctggccccca gcagcaagtc tacctctggc       480
ggcacagccg ctctgggctg cctggtgaag gactacttcc ccgagcccgt gacagtgtcc      540
tggaactctg gcgccctgac cagcggcgtg cacacattcc ctgccgtgct gcagagcagc      600
ggcctgtaca gcctgagcag cgtggtgaca gtgcctagca gctctctggg cacccagacc      660
tacatctgca acgtgaacca caagcccagc aacaccaagg tggacaagaa ggtggagccc      720
aagagctgcg acaagaccca cacctgtccc ccttgtcctg cccctgagct gctgggcgga      780
cccagcgtgt tcctgttccc cccaaagccc aaggacaccc tgatgatcag caggaccccc      840
gaagtgacct gcgtggtggt ggacgtgtcc cacgaggacc ctgaagtgaa gttcaattgg      900
tacgtggacg gcgtggaggt gcacaatgcc aagaccaagc ccagagagga acagtacaac      960
agcacctaca gggtggtgtc cgtgctgacc gtgctgcacc aggactggct gaacggcaaa     1020
gagtacaagt gcaaggtctc caacaaggcc ctgcctgccc catcgagaa aaccatcagc      1080 aaggccaagg ccagcccag agaacccag gtgtacaccc tgcccctag cagggacgag        1140 ctgaccaaga accaggtgtc cctgacctgt ctggtgaagg gcttctaccc cagcgatatc     1200
gccgtggagt gggagtctaa cggccagcct gagaacaact acaagaccac cccccctgtg     1260
ctggacagcg acggcagctt cttcctgtac tccaaactga ccgtggacaa gagcagatgg     1320
cagcagggca acgtgttcag ctgcagcgtg atgcacgagg ccctgcacaa ccactacacc     1380
cagaagtccc tgagcctgag ccccggcaag taatga                               1416

<210> SEQ ID NO 4
<211> LENGTH: 714
<212> TYPE: DNA
<213> ORGANISM: homo sapiens

<400> SEQUENCE: 4
atggacatga gagtgcccgc tcagctgctg ggactgctgc tgctgtggct gagaggcgcc       60
agatgcgaca tccagatgac ccagagccct tctagcctga gcgccagcgt gggcgacaga      120
gtgaccatca cctgtagggc cagccagggc atcaggaact acctggcctg gtatcagcag      180
aagcccggca aggcccccaa gctgctgatc tacgccgcca gcaccctgca gagcggcgtg      240
cccagcagat tcagcggcag cggctccggc accgacttca ccctgaccat cagcagcctg      300
cagcctgagg acgtggccac ctactactgc cagaggtaca caggggcccc ctacaccttc      360
ggacagggca ccaaggtgga gatcaagagg accgtggccg ctcccagcgt gttcatcttc      420
ccacccagcg acgagcagct gaagtctggc accgcctccg tggtctgcct gctgaacaac      480
ttctaccccc gcgaggccaa ggtgcagtgg aaggtggaca acgccctgca gtccggcaac      540
agccaggaaa gcgtcaccga gcaggacagc aaggactcca cctactccct gtccagcacc      600
ctgaccctga gcaaggccga ctacgagaag cacaaggtgt acgcctgcga agtgacccac      660
cagggcctga gcagccctgt gaccaagagc ttcaacaggg gcgagtgcta atga            714
```